US008524927B2

(12) United States Patent
Mazanec et al.

(10) Patent No.: US 8,524,927 B2
(45) Date of Patent: Sep. 3, 2013

(54) PROCESS FOR MAKING ETHYLENE OXIDE USING MICROCHANNEL PROCESS TECHNOLOGY

(75) Inventors: Terry Mazanec, Solon, OH (US); Soumitra Desmukh, Dublin, OH (US); Laura J. Silva, Dublin, OH (US); Torsten Maurer, Lambsheim (DE); Radwan Abdallah, Ludwigshafen (DE); Frank Rosowski, Mannheim (DE)

(73) Assignee: Velocys, Inc., Plain City, OH (US)

( * ) Notice: Subject to any disclaimer, the term of this patent is extended or adjusted under 35 U.S.C. 154(b) by 729 days.

(21) Appl. No.: 12/501,505

(22) Filed: Jul. 13, 2009

(65) Prior Publication Data
US 2011/0009653 A1    Jan. 13, 2011

(51) Int. Cl.
*C07D 301/10* (2006.01)
*C07D 301/03* (2006.01)
*C07C 31/18* (2006.01)

(52) U.S. Cl.
USPC ............ 549/536; 549/534; 549/523; 568/852

(58) Field of Classification Search
USPC ................. 549/538, 541, 542, 536, 534, 523; 568/852
See application file for complete search history.

(56) References Cited

U.S. PATENT DOCUMENTS

| 3,882,049 | A | 5/1975 | Bertolacini et al. | |
|---|---|---|---|---|
| 3,972,837 | A | 8/1976 | Acres et al. | |
| 4,089,810 | A | 5/1978 | Diwell et al. | |
| 4,096,095 | A | 6/1978 | Cairns | |
| 4,289,652 | A | 9/1981 | Hunter et al. | |
| 4,524,236 | A | 6/1985 | McCain | 585/658 |
| 4,908,343 | A | 3/1990 | Bhasin | 502/218 |
| 5,145,824 | A | 9/1992 | Buffum et al. | 502/216 |
| 5,248,251 | A | 9/1993 | Dalla Betta et al. | |
| 5,504,053 | A | 4/1996 | Chou et al. | 502/348 |
| 5,597,773 | A | 1/1997 | Evans et al. | 502/348 |
| 5,703,253 | A | 12/1997 | Evans et al. | 549/536 |
| 5,705,661 | A | 1/1998 | Iwakura et al. | 549/536 |
| 6,040,266 | A | 3/2000 | Fay, III et al. | |
| 6,153,556 | A | 11/2000 | Shima et al. | 502/348 |
| 6,409,072 | B1 | 6/2002 | Breuer et al. | 228/111.5 |
| 6,440,895 | B1 | 8/2002 | Tonkovich et al. | |
| 6,713,036 | B1 | 3/2004 | Vanden Bussche et al. | 423/584 |
| 6,762,311 | B2 | 7/2004 | Rizkalla et al. | 549/534 |
| 7,294,734 | B2 | 11/2007 | Brophy et al. | 558/317 |

(Continued)

FOREIGN PATENT DOCUMENTS

BE    896248    9/1983
CA    2247662   9/1998

(Continued)

OTHER PUBLICATIONS

Kursawe et al.; "Selective Reactions in Microchannel Reactors"; Microreaction Technology: 3$^{rd}$ International Conference on Microreaction Technology, Proceedings of IMRET 3, 1999, pp. 213-223, XP008056307.

(Continued)

*Primary Examiner* — Taylor Victor Oh
(74) *Attorney, Agent, or Firm* — Renner, Otto, Boisselle & Sklar, LLP

(57) ABSTRACT

This invention relates to a process comprising reacting ethylene and oxygen or a source of oxygen in a process microchannel in the presence of a catalyst to form a product comprising ethylene oxide.

70 Claims, 15 Drawing Sheets

(56) References Cited

U.S. PATENT DOCUMENTS

| | | | |
|---|---|---|---|
| 2002/0028164 A1 | 3/2002 | Schutte et al. | 422/198 |
| 2002/0192118 A1 | 12/2002 | Zech et al. | 422/99 |
| 2003/0007904 A1 | 1/2003 | Tonkovich et al. | 422/180 |
| 2004/0034111 A1 | 2/2004 | Tonkovich et al. | 518/726 |
| 2004/0188326 A1 | 9/2004 | Tonkovich et al. | 208/139 |
| 2004/0229752 A1 | 11/2004 | Long et al. | 502/303 |
| 2005/0163701 A1 | 7/2005 | Tonkovich et al. | 423/584 |
| 2005/0165121 A1 | 7/2005 | Wang et al. | 518/726 |
| 2005/0176832 A1 | 8/2005 | Tonkovich et al. | 518/726 |
| 2006/0036106 A1 | 2/2006 | Mazanec et al. | 549/533 |
| 2007/0197801 A1 | 8/2007 | Bolk et al. | 549/229 |
| 2007/0197808 A1 | 8/2007 | Bolk et al. | 549/536 |
| 2008/0081920 A1 | 4/2008 | Gueckel | 549/533 |

FOREIGN PATENT DOCUMENTS

| | | |
|---|---|---|
| CA | 2571986 | 6/2007 |
| DE | 246257 | 6/1987 |
| DE | 3926466 | 2/1991 |
| EP | 0327356 | 9/1989 |
| EP | 0357292 | 7/1990 |
| EP | 0425020 | 10/1990 |
| EP | 0 266 015 B1 | 12/1991 |
| EP | 0 532 325 A1 | 3/1993 |
| EP | 0 496 470 B1 | 9/1994 |
| EP | 0625370 | 11/1994 |
| EP | 0716884 | 12/1995 |
| EP | 1002575 | 5/2000 |
| EP | 1 312 411 A2 | 5/2003 |
| EP | 1 292 587 B1 | 10/2006 |
| EP | 1102628 | 11/2006 |
| EP | 1927398 | 6/2008 |
| FR | 2 895 278 | 12/2006 |
| GB | 1531134 | 11/1978 |
| GB | 2077136 | 12/1981 |
| GB | 2 433 501 A | 6/2007 |
| GB | 2 433 503 A | 6/2007 |
| WO | 9421372 | 9/1994 |
| WO | 9623585 | 8/1996 |
| WO | 9700442 | 1/1997 |
| WO | 9828073 | 7/1998 |
| WO | 98/37457 | 8/1998 |
| WO | 9838147 | 9/1998 |
| WO | 9916542 | 4/1999 |
| WO | 0006301 | 2/2000 |
| WO | 0183105 | 11/2001 |
| WO | 01/96324 A2 | 12/2001 |
| WO | 02/18042 A1 | 3/2002 |
| WO | 03006149 | 1/2003 |
| WO | 03/044003 A1 | 5/2003 |
| WO | 03072246 | 9/2003 |
| WO | 03/106386 A2 | 12/2003 |
| WO | 2004/002971 A1 | 1/2004 |
| WO | 2004/030813 A1 | 4/2004 |
| WO | 2004030813 | 4/2004 |
| WO | 2004/037418 A2 | 5/2004 |
| WO | 2004/091771 A1 | 10/2004 |
| WO | 2004/099113 A1 | 11/2004 |
| WO | 2004/101141 A1 | 11/2004 |
| WO | 2004/103549 A2 | 12/2004 |
| WO | 2005/003025 A2 | 1/2005 |
| WO | 2006/020709 A1 | 2/2006 |
| WO | 2006/055609 A1 | 5/2006 |
| WO | 2006133183 | 12/2006 |
| WO | 2007/071737 A1 | 6/2007 |
| WO | 2007/071741 A1 | 6/2007 |
| WO | 2007/071744 A1 | 6/2007 |
| WO | 2007/076390 A2 | 7/2007 |
| WO | 2007/076392 A2 | 7/2007 |
| WO | 2007/076393 A2 | 7/2007 |
| WO | 2007/076394 A2 | 7/2007 |
| WO | 2007/076395 A2 | 7/2007 |
| WO | 2007/076397 A2 | 7/2007 |
| WO | 2007/076400 A2 | 7/2007 |
| WO | 2007/076402 A2 | 7/2007 |
| WO | 2007/076404 A2 | 7/2007 |
| WO | 2007/076406 A2 | 7/2007 |
| WO | 2007/111997 A2 | 10/2007 |
| WO | 2007/112866 A1 | 10/2007 |
| WO | 2007/122090 A2 | 11/2007 |
| WO | 2007123932 | 11/2007 |
| WO | 2008032797 | 3/2008 |
| ZA | 855317 | 7/1985 |

OTHER PUBLICATIONS

Cybulski et al.; "Monoliths in Heterogeneous Catalysis"; Catal. Rev.—Sci. Eng., 36(2), 179-270 (1994).

Bennett et al.; "Microchannel cooled heatsinks for high average power laser diode arrays"; SPIE, vol. 1865; 1993; pp. 144-153.

International Preliminary Report on Patentability, Application No. PCT/US2009/050342, mailed Jan. 14, 2011.

International Preliminary Report on Patentability and Written Opinion of the International Searching Authority; Application No. PCT/EP2009/058883, issued Jan. 18, 2011.

International Search Report and Written Opinion, Application No. PCT/US2009/050342, mailed Feb. 25, 2010.

Invitation to Pay Additional Fees and Partial International Search Report, Application No. PCT/US2009/050342, mailed Nov. 12, 2009.

Kestenbaum et al.; "Silver-Catalyzed Oxidation of Ethylene to Ethylene Oxide in a Microreaction System"; *Ind. Eng. Chem. Res.*; 2002, 41; pp. 710-719.

Iglesia; "Design, synthesis, and use of cobalt-based Fischer-Tropsch synthesis catalysts"; Applied Catalysis A: General 161 (1997); pp. 59-78.

Chinese Office Action, Application No. 200980127637.4, issued Oct. 10, 2012.

Chinese Office Action, Application No. 200980127637.4, issued Jun. 5, 2013.

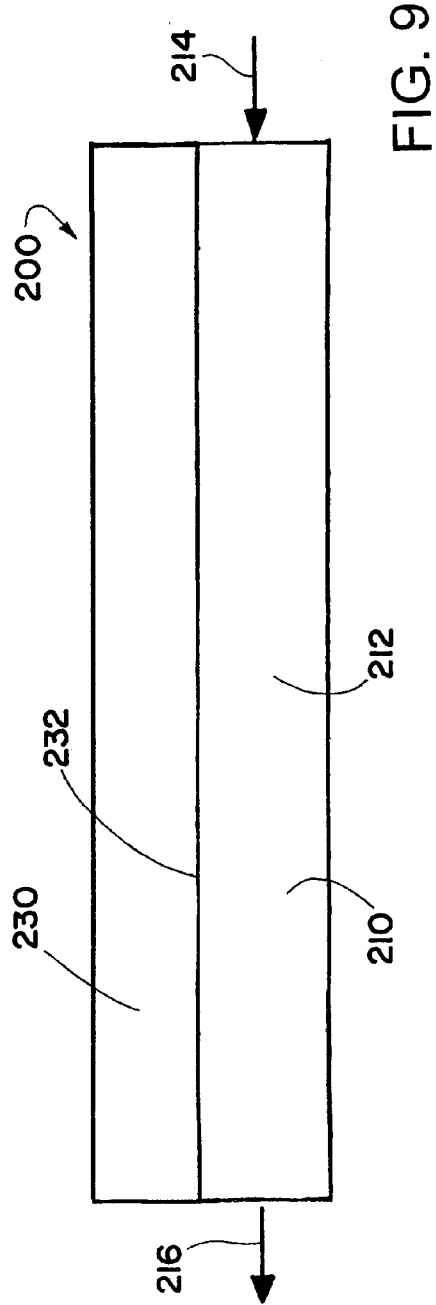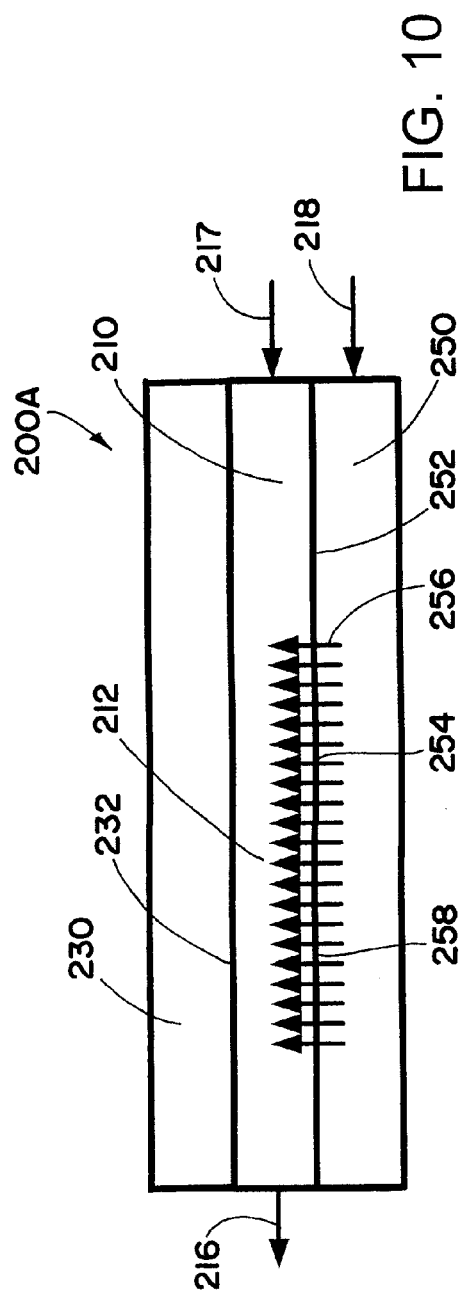

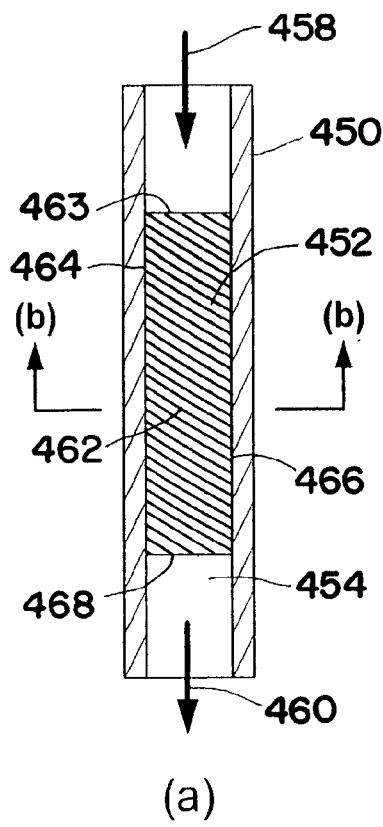
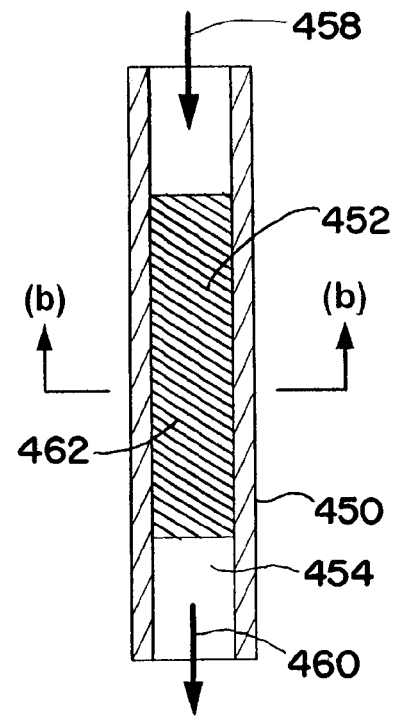
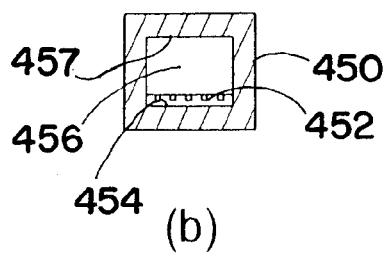
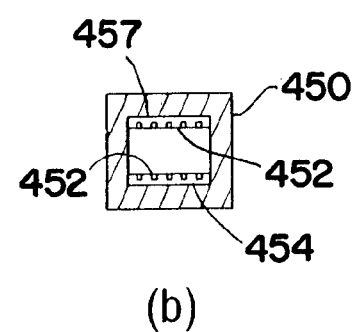
FIG. 23   FIG. 24

PROCESS FOR MAKING ETHYLENE OXIDE USING MICROCHANNEL PROCESS TECHNOLOGY

This application claims priority to U.S. Provisional Application Ser. No. 60/080,347, filed Jul. 14, 2008. The disclosure in this prior application is incorporated herein by reference.

TECHNICAL FIELD

This invention relates to a process for making ethylene oxide using microchannel technology.

BACKGROUND

Ethylene oxide is typically produced by the oxidation of ethylene with oxygen in the presence of a catalyst. The reaction is exothermic.

SUMMARY

A problem with ethylene oxide production relates to the fact that as a production run progresses, the catalyst gradually deactivates. This may be compensated for by allowing the catalyst temperature to increase. This will prolong the production run, but at some point an end of the run (EOR) temperature for the production run will occur. This will occur when the rate of production of ethylene oxide declines to a point at which the run is no longer economical. This will require a shut down of the process to change the catalyst. These shut downs are time consuming and costly. This invention provides a solution to this problem. With the present invention it is possible to achieve higher work rates for a catalyst and/or a longer catalytic life. Both of these contribute to higher levels of productivity. For example, it is estimated that the catalyst life for the ethylene oxide process conducted in a conventional, that is, a non-microchannel, reactor using certain catalysts, may be up to about 7000 hours, while with the inventive process employing a microchannel reactor and the same catalysts, the catalyst life may be about 25,000 hours or longer.

This invention relates to a process, comprising: reacting ethylene and oxygen or a source of oxygen in the presence of a catalyst in a process microchannel to form a product comprising ethylene oxide during a production run, the production run continuing until at least about 0.5 kilotons of ethylene oxide are produced per cubic meter of catalyst; and replacing and/or regenerating the catalyst at the end of the production run.

This invention also relates to a process, comprising: reacting ethylene and oxygen or a source of oxygen in the presence of a catalyst in a process microchannel to form a product comprising ethylene oxide at rate of at least about 350 kilograms of ethylene oxide per cubic meter of catalyst per hour.

This invention also relates to a process, comprising: reacting ethylene and oxygen or a source of oxygen in the presence of a catalyst in a process microchannel to form a product comprising ethylene oxide at a rate of at least about 250 kilograms of ethylene oxide per cubic meter of catalyst per hour, the selectivity to ethylene oxide being at least about 80%, the catalyst being in a reaction zone in the process microchannel; and maintaining an average temperature in the reaction zone below about 220° C.

This invention also relates to a process, comprising: reacting ethylene and oxygen or a source of oxygen in the presence of a catalyst in a process microchannel to form a product comprising ethylene oxide at a rate of at least about 250 kilograms of ethylene oxide per cubic meter of catalyst per hour, the selectivity of ethylene oxide being at least about 80%, the catalyst being in a reaction zone in the process microchannel; and maintaining an average temperature in the reaction zone above about 265° C.

This invention also relates to a process, comprising: reacting ethylene and oxygen or a source of oxygen in the presence of a catalyst in a process microchannel to form a product comprising ethylene oxide, the catalyst being in a reaction zone in the process microchannel, the ethylene oxide being produced during a production run, the average temperature in the reaction zone at the start of the production run being at least about 150° C.; increasing the temperature in the reaction zone during the production run at a sufficient rate to maintain an average production rate of at least about 250 kilograms of ethylene oxide per cubic meter of catalyst per hour; and replacing and/or regenerating the catalyst at the end of the production run.

The ethylene may be formed upstream of the microchannel reactor or it may be formed in the microchannel reactor. Part of the microchannel reactor may be used for ethylene formation and part of the microchannel reactor may be used for ethylene oxide formation. The ethylene may be formed in the microchannel reactor using catalytic oxidative dehydrogenation, catalytic dehydrogenation and/or thermal cracking.

The ethylene oxide may be converted into ethylene glycol. The ethylene glycol may be formed downstream of the microchannel reactor. The ethylene glycol may be formed in the microchannel reactor. Part of the microchannel reactor may be used for ethylene oxide formation and part of the microchannel reactor may be used for ethylene glycol formation.

The process may include the step of quenching the product. The product may be quenched downstream of the microchannel reactor. The product may be quenched in the microchannel reactor.

BRIEF DESCRIPTION OF THE DRAWINGS

In the annexed drawings, like parts and features have like designations. A number of the drawings provided herein are schematic illustrations which may not be is drawn to scale or proportioned accurately.

In FIG. 6A, the ethylene oxide reacts with water in a glycol forming reactor downstream of the ethylene oxide forming reactor. The glycol forming reaction may be conducted in a conventional reactor or in a microchannel reactor. The glycol forming reaction is exothermic. A heat exchange fluid is used to control temperature. In FIG. 6B, the ethylene oxide reacts with the water to form ethylene glycol in the same microchannel reactor used to form the ethylene oxide.

FIGS. 9-14 are schematic illustrations of repeating units that may be used in the microchannel reactor used with the inventive process.

FIGS. 17-25 are schematic illustrations of catalysts or catalyst support structures that may be used in the microchannel reactor used with the inventive process. FIG. 23(b) is a cross sectional view of FIG. 23(a) taken along line (b)-(b) in FIG. 23(a). FIG. 24(b) is a cross sectional view of FIG. 24(a) taken along line (b)-(b) in FIG. 24(a).

DETAILED DESCRIPTION

All ranges and ratio limits disclosed in the specification and claims may be combined in any manner. It is to be understood that unless specifically stated otherwise, references to "a," "an," and/or "the" may include one or more than one, and that reference to an item in the singular may also include the item in the plural. All combinations specified in the claims may be combined in any manner.

Figure 1:
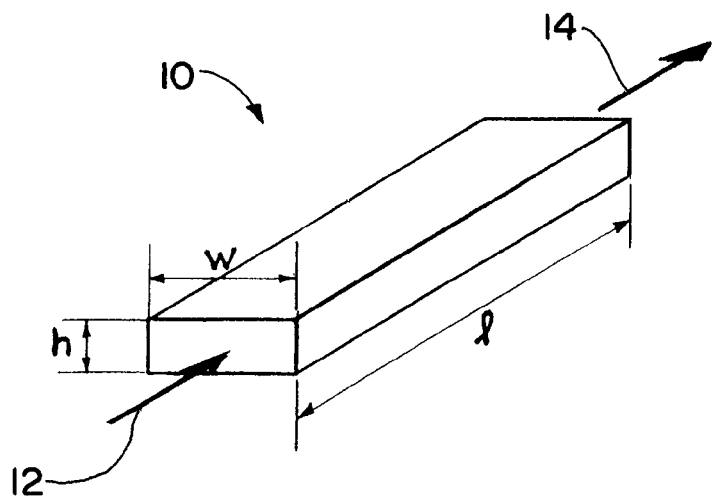
FIG. 1 is a schematic illustration of a microchannel that may be used with the inventive process.

The term "microchannel" refers to a channel having at least one internal dimension of height or width of up to about 10 millimeters (mm), and in one embodiment up to about 5 mm, and in one embodiment up to about 2 mm. An example of a microchannel that may be used with the inventive process is illustrated in FIG. 1. Referring to FIG. 1, microchannel 10 has a height (h), width (w) and length (l). Fluid flows through the microchannel 10 in the direction indicated by arrows 12 and 14. Both the height (h) and width (w) are perpendicular to the flow of fluid in the microchannel 10. The microchannel may comprise at least one inlet and at least one outlet wherein the at least one inlet is distinct from the at least one outlet. The microchannel may not be merely an orifice. The microchannel may not be merely a channel through a zeolite or a mesoporous material. The length of the microchannel may be at least about two times the height or width, and in one embodiment at least about five times the height or width, and in one embodiment at least about ten times the height or width. The height or width may be referred to as the gap between opposed internal walls of the microchannel. The internal height or width of the microchannel may be in the range of about 0.05 to about 10 mm, and in one embodiment from about 0.05 to about 5 mm, and in one embodiment from about 0.05 to about 2 mm, and in one embodiment from about 0.05 to about 1.5 mm, and in one embodiment from about 0.05 to about 1 mm, and in one embodiment from about 0.05 to about 0.75 mm, and in one embodiment from about 0.05 to about 0.5 mm. The other internal dimension of height or width may be of any dimension, for example, up to about 3 meters, and in one embodiment about 0.01 to about 3 meters, and in one embodiment about 0.1 to about 3 meters. The length of the microchannel may be of any dimension, for example, up to about 10 meters, and in one embodiment from about 0.1 to about 10 meters, and in one embodiment from about 0.2 to about 10 meters, and in one embodiment from about 0.2 to about 6 meters, and in one embodiment from 0.2 to about 3 meters. The microchannel may have a cross section having any shape, for example, a square, rectangle, circle, semicircle, trapezoid, etc. The shape and/or size of the cross section of the microchannel may vary over its length. For example, the height or width may taper from a relatively large dimension to a relatively small dimension, or vice versa, over the length of the microchannel.

The term "process microchannel" refers to a microchannel wherein a process is conducted. The process may relate to the formation of ethylene oxide, ethylene and/or ethylene glycol.

The term "microchannel reactor" refers to an apparatus comprising one or more process microchannels wherein a reaction process is conducted. The process may be an ethylene oxide, ethylene and/or ethylene glycol forming reaction process. When two or more process microchannels are used, the process microchannels may be operated in parallel. The microchannel reactor may include a header or manifold assembly for providing for the flow of fluid into the one or more process microchannels, and a footer or manifold assembly providing for the flow of fluid out of the one or more process microchannels. The microchannel reactor may further comprise one or more heat exchange channels adjacent to and/or in thermal contact with the one or more process microchannels. The heat exchange channels may provide heating and/or cooling for the fluids in the process microchannels. The heat exchange channels may be microchannels. The microchannel reactor may include a header or manifold assembly for providing for the flow of heat exchange fluid into the heat exchange channels, and a footer or manifold assembly providing for the flow of heat exchange fluid out of the heat exchange channels.

The term "conventional reactor" refers to a reactor that is not a microchannel reactor.

The term "volume" with respect to volume within a process microchannel includes all volume in the process microchannel a process fluid may flow through or flow by. This volume may include volume within surface features that may be positioned in the process microchannel and adapted for the flow of fluid in a flow-through manner or in a flow-by manner.

The term "adjacent" when referring to the position of one channel relative to the position of another channel means directly adjacent such that a wall or walls separate the two channels. In one embodiment, the two channels may have a common wall. The common wall may vary in thickness. However, "adjacent" channels may not be separated by an intervening channel that may interfere with heat transfer between the channels. One channel may be adjacent to another channel over only part of the dimension of the another channel. For example, a process microchannel may be longer than and extend beyond one or more adjacent heat exchange channels.

The term "thermal contact" refers to two bodies, for example, two channels, that may or may not be in physical contact with each other or adjacent to each other but still exchange heat with each other. One body in thermal contact with another body may heat or cool the other body.

The term "fluid" refers to a gas, a liquid, a mixture of a gas and a liquid, or a gas or a liquid containing dispersed solids, liquid droplets and/or gaseous bubbles. The droplets and/or bubbles may be irregularly or regularly shaped and may be of similar or different sizes.

The terms "gas" and "vapor" have the same meaning and are sometimes used interchangeably.

The term "residence time" or "average residence time" refers to the internal volume of a space within a channel occupied by a fluid flowing in the space divided by the average volumetric flow rate for the fluid flowing in the space at the temperature and pressure being used.

The terms "upstream" and "downstream" refer to positions within a channel (e.g., a process microchannel) or in a process or process flow sheet that is relative to the direction of flow of a fluid in the channel or process or process flow sheet. For example, a position within a channel or a process or process flow sheet not yet reached by a portion of a fluid stream flowing toward that position would be downstream of that portion of the fluid stream. A position within the channel or a process or process flow sheet already passed by a portion of a fluid stream flowing to away from that position would be upstream of that portion of the fluid stream. The terms "upstream" and "downstream" do not necessarily refer to a vertical position since the channels used herein may be oriented horizontally, vertically or at an inclined angle.

The term "shim" refers to a planar or substantially planar sheet or plate. The thickness of the shim may be the smallest dimension of the shim and may be up to about 4 mm, and in one embodiment in the range from about 0.05 to about 2 mm, and in one embodiment in the range of about 0.05 to about 1 mm, and in one embodiment in the range from about 0.05 to about 0.5 mm. The shim may have any length and width.

Figure 15:
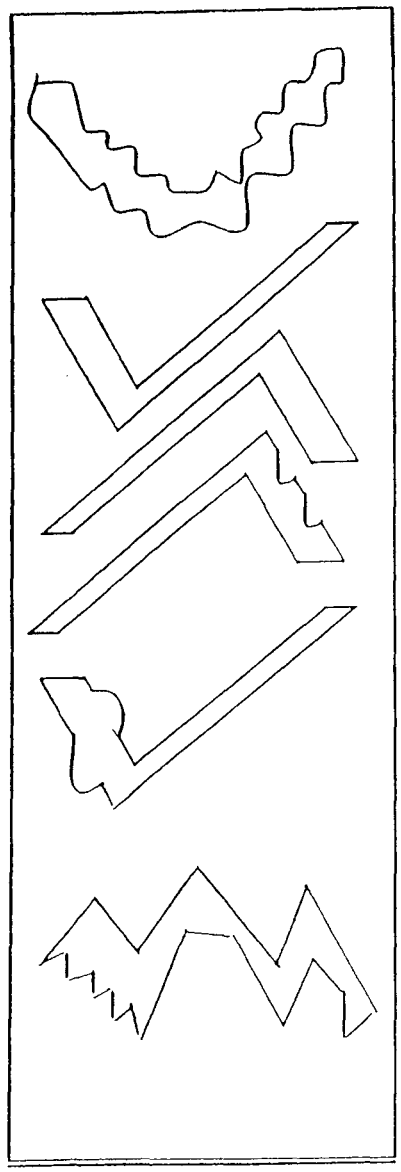
FIGS. 15 and 16 are schematic illustrations of surface features that may be used in the microchannel reactor used with the inventive process.
Figure 16:
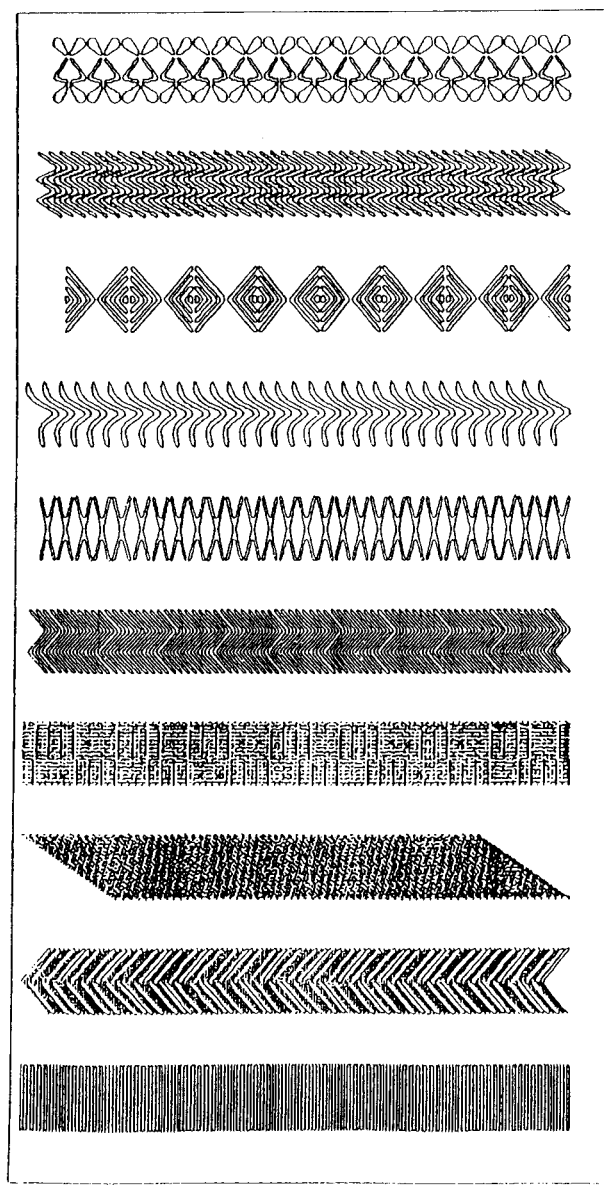
Figure 25:
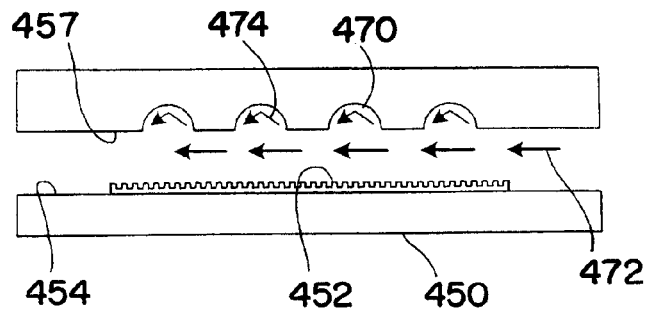

The term "surface feature" refers to a depression in a channel wall and/or internal channel structure (e.g., internal fin) and/or a projection from a channel wall and/or internal channel structure that disrupts flow within the channel. Examples of surface feature designs that may be used are illustrated in FIGS. 15, 16 and 25. The surface features may be in the form of circles, spheres, hemispheres, frustrums, oblongs, squares, rectangles, angled rectangles, checks, chevrons, vanes, airfoils, wavy shapes, and the like. Combinations of two or more of the foregoing may be used. The surface features may contain subfeatures where the major walls of the surface features further contain smaller surface features that may take the form of notches, waves, indents, holes, burrs, checks, scallops, and the like. The surface features may have a depth, a width, and a length. The surface features may be formed on or in one or more of the interior walls of the process microchannels and/or heat exchange channels used in accordance with the inventive process. The surface features may be referred to as passive surface features or passive mixing features. The surface features may be used to disrupt flow (for example, disrupt laminar flow streamlines) and create advective flow at an angle to the bulk flow direction.

The term "waveform" refers to a contiguous piece of thermally conductive material that is transformed from a planar object to a three-dimensional object. The waveform may be used to form one or more microchannels. The waveform may comprise a right angled corrugated insert which may be sandwiched between opposed planar sheets or shims. In this manner one or more microchannels may be defined on three sides by the waveform and on the fourth side by one of the planar sheets or shims. The waveform may be made of any of the thermally conductive materials disclosed herein as being useful for making the microchannel reactor. These may include copper, aluminum, stainless steel, and the like. The thermal conductivity of the waveform may be about 1 W/m-K or higher.

The term "bulk flow direction" refers to the vector through which fluid may is travel in an open path in a channel.

The term "bulk flow region" refers to open areas within a channel (e.g., a process microchannel). A contiguous bulk flow region may allow rapid fluid flow through a channel without significant pressure drop. In one embodiment, the flow in the bulk flow region may be laminar. A bulk flow region may comprise at least about 5% of the internal volume and/or cross-sectional area of a microchannel, and in one embodiment from about 5% to about 100%, and in one embodiment from about 5% to about 99%, and in one embodiment about 5% to about 95%, and in one embodiment from about 5% to about 90%, and in one embodiment from about 30% to about 80% of the internal volume and/or cross-sectional area of the microchannel.

The term "open channel" refers to a channel (e.g., a microchannel) with a gap of at least about 0.01 mm that extends all the way through the channel such that fluid may flow through the channel without encountering a barrier to flow. The gap may extend up to about 10 mm.

The term "cross-sectional area" of a channel (e.g., process microchannel) refers to an area measured perpendicular to the direction of the bulk flow of fluid in the channel and may include all areas within the channel including any surface features that may be present, but does not include the channel walls. For channels that curve along their length, the cross-sectional area may be measured perpendicular to the direction of bulk flow at a selected point along a line that parallels the length and is at the center (by area) of the channel. Dimensions of height and width may be measured from one interior channel wall to the opposite interior channel wall. These dimensions may be average values that account for variations caused by surface features, surface roughness, and the like.

The term "open cross-sectional area" of a channel (e.g., process microchannel) refers to an area open for bulk fluid flow in a channel measured perpendicular to the direction of the bulk flow of fluid flow in the channel. The open cross-sectional area may not include internal obstructions such as surface features and the like which may be present.

The term "superficial velocity" for the velocity of a fluid flowing in a channel refers to the velocity resulting from dividing the volumetric flow rate of the fluid at the inlet temperature and pressure of the channel divided by the cross-sectional area of the channel.

The term "free stream velocity" refers to the velocity of a stream flowing in a channel at a sufficient distance from the sidewall of the channel such that the velocity is at a maximum value. The velocity of a stream flowing in a channel is zero at the sidewall if a no slip boundary condition is applicable, but increases as the distance from the sidewall increases until a constant value is achieved. This constant value is the "free stream velocity."

The term "process fluid" refers to reactants, product, diluent and/or other fluid that enters, flows in and/or flows out of a process microchannel.

The term "reactants" refers to ethylene and/or oxygen or a source of oxygen when used with reference to the inventive process for converting ethylene and oxygen or a source of oxygen to ethylene oxide.

The term "reaction zone" refers to the space within a microchannel wherein a chemical reaction occurs or wherein a chemical conversion of at least one species occurs. The reaction zone may contain one or more catalysts.

The term "graded catalyst" refers to a catalyst with one or more gradients of catalytic activity. The graded catalyst may have a varying concentration or surface area of a catalytically active metal. The graded catalyst may have a varying turnover rate of catalytically active sites. The graded catalyst may have physical properties and/or a form that varies as a function of distance. For example, the graded catalyst may have an active metal concentration that is relatively low at the entrance to a process microchannel and increases to a higher concentration near the exit of the process microchannel, or vice versa; or a lower concentration of catalytically active metal nearer the center (i.e., midpoint) of a process microchannel and a higher concentration nearer a process microchannel wall, or vice versa, etc. The thermal conductivity of a graded catalyst may vary from one location to another within a process microchannel. The surface area of a graded catalyst may be varied by varying size of catalytically active metal sites on a constant surface area support, or by varying the surface area of the support such as by varying support type or particle size. A graded catalyst may have a porous support where the surface area to volume ratio of the support is higher or lower in different parts of the process microchannel followed by the application of the same catalyst coating everywhere. A combination of two or more of the preceding embodiments may be used. The graded catalyst may have a single catalytic component or multiple catalytic components (for example, a bimetallic or trimetallic catalyst). The graded catalyst may change its properties and/or composition gradually as a function of distance from one location to another within a process microchannel. The graded catalyst may comprise rimmed particles that have "eggshell" distributions of catalytically active metal within each particle. The graded catalyst may be graded in the axial direction along the length of a process microchannel or in the lateral direction. The graded catalyst may have different catalyst compositions, different loadings and/or numbers of active catalytic sites that may vary from one position to another position within a process microchannel. The number of catalytically active sites may be changed by altering the porosity of the catalyst structure. This may be accomplished using a washcoating process that deposits varying amounts of catalytic material. An example may be the use of different porous catalyst thicknesses along the process microchannel length, whereby a thicker porous structure may be left where more activity is required. A change in porosity for a fixed or variable porous catalyst thickness may also be used. A first pore size may be used adjacent to an open area or gap for flow and at least one second pore size may be used adjacent to the process microchannel wall.

The term "cubic meter of catalyst" refers to the volume of the catalytically active portion of a catalyst. For a bed of particulate solids the term "cubic meter of catalyst" may refer to the volume of the space in which the active catalyst is loaded.

The term "heat exchange channel" refers to a channel having a heat exchange fluid in it that gives off heat and/or absorbs heat. The heat exchange channel may absorb heat from or give off heat to an adjacent channel (e.g., process microchannel) and/or one or more channels in thermal contact with the heat exchange channel. The heat exchange channel may absorb heat from or give off heat to channels that are adjacent to each other but not adjacent to the heat exchange channel. In one embodiment, one, two, three or more channels may be adjacent to each other and positioned between two heat exchange channels.

The term "heat transfer wall" refers to a common wall between a process microchannel and an adjacent heat exchange channel where heat transfers from one channel to the other through the common wall.

The term "heat exchange fluid" refers to a fluid that may give off heat and/or absorb heat.

The term "heat exchange medium" refers to a substance or device that absorbs heat or gives off heat and may be used to cool or heat another substance or device. The another substance or device may be, for example, a channel that is adjacent to or in thermal contact with the heat exchange medium. An example of a heat exchange medium would be a heat exchange fluid in a heat exchange channel.

The term "conversion of reactant" refers to the reactant mole change between a fluid flowing into a microchannel reactor and a fluid flowing out of the microchannel reactor divided by the moles of reactant in the fluid flowing into the microchannel reactor.

The term "yield" is used herein to refer to the number of moles of product flowing out of a microchannel reactor divided by the number of moles of a reactant flowing into the microchannel reactor.

The term "cycle" is used herein to refer to a single pass of the reactants through a microchannel reactor.

The term "conversion of ethylene" refers to the number of moles of carbon observed in the microchannel reactor exit stream as ethylene oxide and carbon dioxide divided by the total number of moles of carbon exiting the microchannel reactor as ethylene, ethylene oxide and carbon dioxide.

The term "conversion of oxygen" refers to the number of moles of oxygen observed in the microchannel reactor exit stream as ethylene oxide and carbon dioxide divided by the total number of moles of oxygen exiting the microchannel reactor as oxygen, ethylene oxide and carbon dioxide.

The concentration of a reactant "on a whole feed basis" refers to the total amount of the reactant (e.g., oxygen) flowing into a microchannel reactor. This would include reactant flowing into the front entrance of a process microchannel in the microchannel reactor as well as reactant flowing into the process microchannel through openings in its sidewall downstream from the entrance. The downstream addition of a reactant may be referred to as a "staged addition" of the reactant.

The term "selectivity to ethylene oxide" ($S_{EO}$) refers to the extent of production of ethylene oxide from ethylene. Selectivity to ethylene oxide may be calculated for the oxidation of ethylene to ethylene oxide with carbon dioxide as an unwanted side product using the reaction stoichiometry wherein one mole of ethylene consumes one-half mole of oxygen for the formation of ethylene oxide and three moles of oxygen for the formation of carbon dioxide. Mathematically, this may be expressed as:

$$S_{EO} = \frac{6}{5} - \frac{2}{5}\frac{\dot{n}_O X_O}{\dot{n}_E X_E} \text{ where } \frac{\dot{n}_O}{\dot{n}_E}$$

is the ratio of the molar feed rates of oxygen and ethylene i.e., a ratio of their feed concentrations. $X_E$ and $X_O$ denote the conversion of ethylene and the conversion of oxygen, respectively.

The term "catalyst productivity" refers to the cumulative amount of ethylene oxide produced for a catalyst, measured in the amount (e.g., kilotons (kt)) of ethylene oxide produced per cubic meter of catalyst ($kt_{EO}/m^3_{cat}$).

The term "quench" refers to a process by which a chemical reaction is terminated using a rapid reduction in temperature of the reaction mixture, a rapid introduction of a reactant or non-reactant fluid into the reaction mixture, or flowing the reaction mixture through a restricted opening or passageway having a dimension at or below the quench diameter.

The term "quench diameter" refers to the internal dimension (e.g., height, width, diameter) of an opening or passageway for a reaction mixture to flow through below which the reaction terminates.

The term "start-of-run" (SOR) refers to the point in time during a production run at which the process begins to produce ethylene oxide at a rate of at least about 250 kilograms per cubic meter of catalyst per hour ($Kg/m^3_{cat}/hr$). The start-of-run temperature may be in the range from about 150° C. to about 250° C., and in one embodiment in the range from about 150° C. to about 240° C., and in one embodiment in the range from about 150° C. to about 230° C., and in one embodiment in the range from about 150° C. to about 220° C., and in one embodiment in the range from about 150° C. to about 210° C., and in one embodiment in the range from about 150° C. to about 200° C., and in one embodiment in the range from about 150° C. to about 190° C.

The term "end-of-run" (EOR) refers to the point in time when a production run is considered to be no longer economical. In one embodiment, the term end-of-run refers to the point in time during a production run when the average temperature in the reaction zone of a process microchannel exceeds about 265° C. In one embodiment, the term end-of-run refers to the point in time during a production run when in order to maintain a selectivity to ethylene oxide of at least about 80%, and in one embodiment at least about 82%, and in one embodiment at least about 84%; and/or the rate of production of ethylene oxide decreases to a level below about 245 kilograms of ethylene oxide per cubic meter of catalyst, and in one embodiment below about 240 kilograms of ethylene oxide per cubic meter of catalyst, and in one embodiment below about 235 kilograms of ethylene oxide per cubic meter of catalyst, and in one embodiment below about 230 kilograms of ethylene oxide per cubic meter of catalyst, and in one embodiment below about 225 kilograms of ethylene oxide per cubic meter of catalyst, or below about 220 kilograms of ethylene oxide per cubic meter of catalyst.

The term "ton" is used herein to refer to a metric ton (i.e., 1000 kilograms or 2204.6 pounds). The term "kiloton" or "kt" refers to 1000 metric tons.

The inventive process, in one embodiment, may provide the advantages of reducing capital equipment costs, increasing feedstock utilization, reducing reactant recycle, and/or reducing or eliminating the requirement for using diluents or safening agents. In one embodiment, the per pass conversion of the ethylene, oxygen or source of oxygen, or ethylene and oxygen or source of oxygen may be enhanced without loss of selectivity which may result in smaller recycle streams. The inventive process may be conducted with a reactant composition that is relatively close to stoichiometric; this provides the advantage of reduced separation costs, e.g., eliminating or reducing the requirement for a $CO_2$ scrubber. This also provides the potential for integrating novel separation schemes with the process.

The microchannel reactor used with the inventive process, in one embodiment, utilizes an enhanced capacity for heat removal, and as a result there may be little need for diluent gases or excess hydrocarbon to limit temperature excursions. Thus, the process may be run with a reactant composition that is much closer to stoichiometric. This may shrink the recycle stream significantly, resulting in a savings on power and an increase in plant capacity. Catalyst inventory may be to reduced and some separation equipment may be eliminated. In one embodiment, the conversion may be sufficient to eliminate recycle altogether, which would result in an even greater savings and enhanced economics compared to conventional (that is, non-microchannel) processes.

In one embodiment, the overall conversion of ethylene may be about 80%, however the per pass conversion may be slightly more than about 15%. The low per pass yield may create a need for a downstream separation and recycle of ethylene. Increased per pass conversion may reduce the volume of gas to be recycled and ease the separation of the ethylene oxide product stream. A one-pass microchannel process may provide for a system cost advantage, both capital and operating. A once-through process may also permit the use of air as the oxidant rather than purified oxygen, resulting in further savings.

In one embodiment, the conversion of ethylene to ethylene oxide may be accompanied by the formation of carbon dioxide (for example, selectivities of about 80% ethylene oxide and 20% $CO_2$). The activation energy to form ethylene oxide may be lower than that to form carbon dioxide. Thus, a lower temperature operation and reduced temperature excursions may directly reduce the production of carbon dioxide. The higher ethylene oxide selectivity may improve reactant composition or feedstock utilization at a reduced operating cost.

The catalyst life provided by the inventive process may be at least about 2 times longer than with the same catalyst in a conventional tubular non-microchannel reactor due to better temperature control that may be achieved with the inventive process. In one embodiment, the catalyst life may be at least about 2.2, and in one embodiment at least about 2.5, and in one embodiment at least about 2.7, times longer than with the same catalyst in a conventional tubular non-microchannel reactor. Thus, with the inventive process, in one embodiment, the reactor may be operated at least about 2 times longer between catalyst change outs, and/or at least about 2 times, and in one embodiment at least about 3 times, and in one embodiment at least about 4 times, more ethylene oxide may be produced by the same volume of catalyst before it needs to be changed due to loss of activity, selectivity, or both activity and selectivity.

The reactants or process feed may comprise ethylene and oxygen or a source of oxygen. A mixture of the ethylene and oxygen or a source of oxygen may be referred to as a reactant composition. The ethylene may be combined with the oxygen or source of oxygen in the microchannel reactor or upstream of the microchannel reactor. The purity of the reactants may not be critical, although it is desirable to avoid the presence of compounds which may poison the catalyst.

The reactants or process feed may further comprise one or more organic is halides. The organic halide may comprise one or more alkyl and/or alkylene halides, for example, ethyl chloride and/or vinyl chloride, and the like. The organic halides may be used as promoters for the conversion of ethylene and oxygen to ethylene oxide. The alkyl groups may contain from 1 to about 5 carbon atoms, and in one embodiment from 1 to about 3 carbon atoms. The alkylene groups may contain from 2 to about 5 carbon atoms, and in one embodiment from 2 to about 3 carbon atoms. The halides may comprise chloride, bromide and/or iodide. The halide may comprise chloride.

The oxygen or source of oxygen may comprise molecular oxygen, air and/or other oxidants, such as nitrogen oxides (e.g., NO, $N_2O$), which may function as sources of oxygen. The source of oxygen may comprise oxygen enriched air. The source of oxygen may comprise a mixture of oxygen and/or air, and carbon dioxide. Gaseous mixtures containing oxygen, such as mixtures of oxygen and air, or mixtures of oxygen and an inert gas (e.g., helium, argon, etc.) or a diluent gas (e.g., carbon dioxide, water vapor, etc.) may be used.

The reactants or process feed may comprise from about 10% to about 75% by volume ethylene on a whole feed basis, and in one embodiment from about 10% to about 70%, and in one embodiment from about 20% to about 65%, and in one embodiment from about 25% to about 50% by volume ethylene. The reactants or process feed may comprise at least about 5% by volume oxygen or a source of oxygen on a whole feed basis, and in one embodiment from about 5 to about 50% by volume, and in one embodiment from about 8 to about 35% by volume, and in one embodiment from about 10 to about 25% by volume oxygen or a source of oxygen. The mole ratio of ethylene to oxygen or source of oxygen on a whole feed basis may be in the range from about 10:1 to about 0.1:10, and in one embodiment from about 5:1 to about 1.5:1. The reactants or process feed may contain up to about 100 parts per million (ppm) by volume on a whole feed basis of one or more organic halides, and in one embodiment in the range from about 0.3 to about 100 ppm, and in one embodiment in the range from about 0.3 to about 70 ppm, and in one embodiment from about 0.3 to about 50 ppm, and in one embodiment from about 0.3 to about 25 ppm, and in one embodiment from about 1 to about 10 ppm.

Unlike conventional processes for converting ethylene to ethylene oxide which have to take into account the possibility of explosions for mixtures of oxygen and ethylene, the possibility of such explosions with the inventive process is of less concern. Thus, for example, the inventive process may be operated using a reactant composition containing at least about 25% by volume oxygen, and in one embodiment from about 25% to about 50% by volume oxygen, while conventional processes are typically limited to employing oxygen concentrations of about 7-8% by volume. This advantage is believed to be due to the relatively brief catalyst contact times employed in the process microchannels, the added cooling provided by the inventive process, and the dimensions of the process microchannels which make them effective flame arresters preventing the propagation of combustion reactions and flames that would normally lead to explosions and/or detonations. Thus, with the inventive process it is possible to operate in the explosion range, that is, from about 25 to about 50% by volume oxygen, without incurring an explosion.

It may also be possible to conduct the inventive process using an oxygen concentration in the range from about 5% to about 50% by volume, and in one embodiment in the range from about 5% to about 25% by volume, and in one embodiment in the range from about 5% to about 15% by volume, and in one embodiment in the range from about 5% to about 10% by volume. It may be advantageous to use concentrations of oxygen below the explosion range for certain embodiments of the inventive process when the reaction process is used in combination with other unit operations where an oxygen concentration in the explosion range may be undesirable.

The reactants or process feed may include one or more diluent materials. The diluent materials may include nitrogen, helium, methane, natural gas, carbon dioxide, liquid water, steam, argon, and the like. The diluent materials may be mixed with the ethylene, the oxygen or source of oxygen, or a mixture of both the ethylene and the oxygen or source of oxygen. The volume ratio of diluent to ethylene and/or oxygen or source of oxygen may be in the range from zero to about 75% by volume, and in one embodiment in the range from zero to about 50% by volume, and in one embodiment in the range from about 0.1 to about 75% by volume, and in one embodiment in the range from about 1 to about 75% by volume, and in one embodiment in the range from about 5 to about 75% by volume, and in one embodiment in the range from about 10 to about 75% by volume, and in one embodiment in the range from about 20 to about 75% by volume. However, an advantage of at least one embodiment of the invention is that it is possible to conduct the inventive process without the use of such diluents or with a reduced amount of such diluents. Thus, a more efficient and compact process may be provided.

The reactants or process feed may comprise on a whole feed basis from about 5% to about 50% by volume of oxygen, from about 10% to about 75% by volume of ethylene, from about 10% to about 75% by volume of one or more diluent materials, and up to about 100 ppm by volume of one or more organic halides. The reactants or process feed may comprise on a whole feed basis from about 5% to about 25% by volume of oxygen, from about 25% to about 50% by volume of ethylene, from about 25% to about 65% by volume of one or more diluent materials, and up to about 100 ppm by volume of one or more organic halides.

The reactants or process feed may further comprise, in part or in whole, one or more recycle streams from which ethylene oxide, and optionally other components, have been separated out from the product stream. The recycled steam may contain one or more reaction by-products such as carbon dioxide. The reactants or process feed comprising one or more recycle streams may contain up to about 20% by volume carbon dioxide on a whole feed basis, and in one embodiment up to about 10% by volume carbon dioxide, and in one embodiment up to about 5% by volume, and in one embodiment up to about 1% by volume carbon dioxide, and in one embodiment up to about 0.1% by volume carbon dioxide. In one embodiment, the reactants or process feed, whether or not comprising recycled streams, may be characterized by the absence of carbon dioxide.

The local conditions in the microchannel reactor may be controlled via tailoring temperature and/or composition profiles via one or more of the following: heat exchange with heat exchange channels adjacent to the one or more process microchannels in the microchannel reactor; heat exchange with heat exchange channels in thermal contact with the process microchannels; heat exchange with multiple combinations of heat exchange channels strategically placed to correspond to individual reactor sections; addition of one or more reactants and/or diluents using staged addition along the axial length of the process microchannels.

An isothermal reactor profile may be employed. With such a thermal profile, a partial boiling heat exchange fluid may be used.

A tailored temperature profile along the length of the process microchannels may be used.

In order to control the exothermic reaction via heat exchange with a heat exchange medium, for example, heat exchange fluid, the process may employ a heat flux at or near the entrance to the microchannel reactor that is higher than the heat flux near the outlet of the microchannel reactor.

Figure 2:
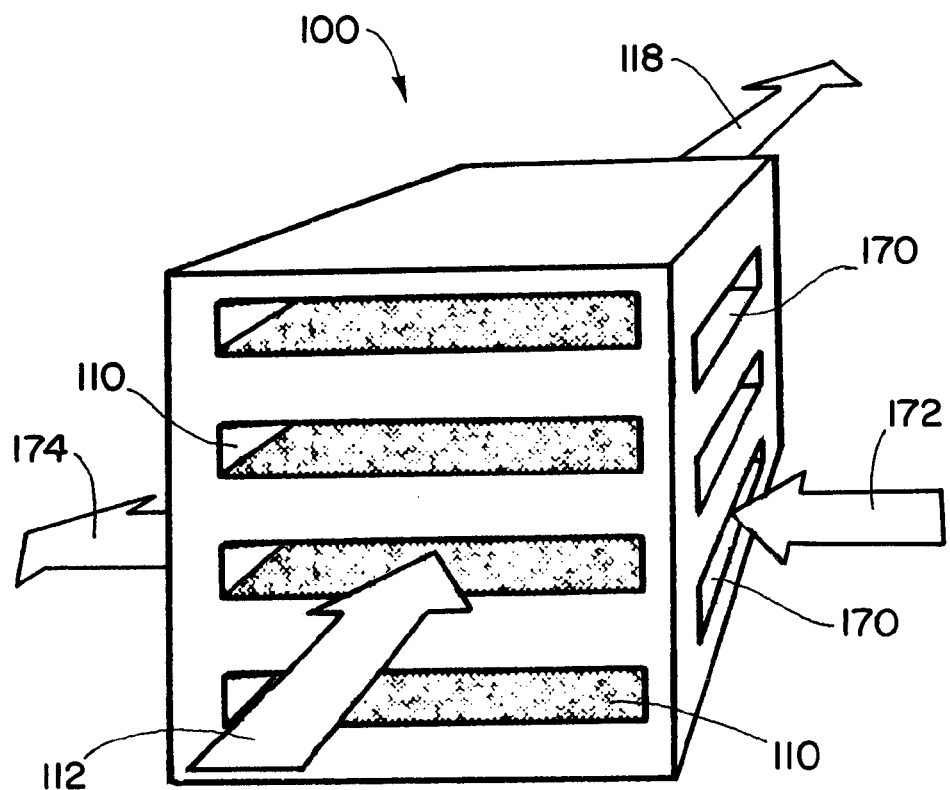
FIG. 2 is a schematic illustration of a microchannel reactor that may be used to conduct the inventive process. This microchannel reactor comprises a plurality of process microchannels and heat exchange channels stacked one above another. Process fluid flows in the process microchannels and heat exchange fluid flows in the heat exchange channels. The process fluid flows in a direction that is cross-current to the flow of the heat exchange fluid.

The microchannel reactor may be constructed as illustrated in FIG. 2. Referring to FIG. 2, microchannel reactor 100 comprises a plurality of ethylene oxide forming process microchannels 110 and heat exchange channels 170 stacked one above the other. The microchannel reactor 100 may be in the form of a cubic block. The cubic block may have a length in the range from about 10 to about 1000 cm, and in one embodiment in the range from about 20 to about 200 cm. The cubic block may have a width in the range from about 10 to about 1000 cm, and in one embodiment in the range from about 20 to about 200 cm. The cubic block may have a height in the range from about 10 to about 1000 cm, and in one embodiment in the range from about 20 to about 200 cm. The reactants may enter the process microchannels 110 as indicated by arrow 112. Product may flow out of the process microchannels as indicated by arrow 118. Heat exchange fluid may enter the heat exchange channels 170 as indicated by arrow 172. Heat exchange fluid may flow out of the heat exchange channels 170 as indicated by arrow 174. The microchannel reactor 100 may have a feed stream header or manifold to provide for the flow of the reactants into the process microchannels 110, a product footer or manifold to provide for the flow of product out of the process microchannels 110, a heat exchange inlet manifold to provide for the flow of heat exchange fluid into the heat exchange channels 170, and a heat exchange outlet manifold to provide for the flow of heat exchange fluid out of the heat exchange channels 170.

The microchannel reactor 100 may contain one or more repeating units. Each repeating unit contains one or more process microchannels and one or more heat exchange channels. Examples of some of the repeating units that may be used are illustrated in FIGS. 9-14 and 26-27. These are discussed below. Each of the process microchannels may contain one or more reaction zones wherein the reactants react to form the desired product. A catalyst in solid form may be present in the one or more reaction zones. The catalyst may comprise a homogeneous is catalyst immobilized on a solid. Each repeating unit may contain one or more heat exchange channels. In one embodiment, each process microchannel may be combined with one or more adjacent reactant stream channels to provide for the staged addition of one of the reactants (e.g., oxygen) into the process microchannel. The process microchannel and the adjacent reactant stream channel may have a common wall with a plurality of openings in the common wall. These openings may be used to provide for the flow of one of the reactants from the adjacent reactant stream channel into the process microchannel. The feed stream header may comprise one or more manifolds for distributing mixtures of the reactants to the process microchannels. Alternatively, the feed stream header may comprise separate manifolds for distributing the reactants separately to the process microchannels and to the adjacent reactant stream channels.

Figure 3A:
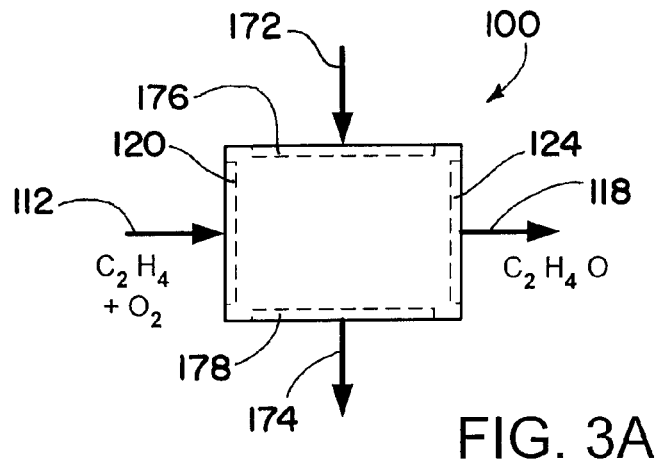
FIGS. 3A and 3B are flow sheets illustrating the inventive process for converting ethylene and oxygen or a source of oxygen to ethylene oxide. The process may be conducted in the microchannel reactor illustrated in FIG. 2. The reaction is exothermic. A heat exchange fluid is used to control temperature. With the process illustrated in FIG. 3A, the ethylene and oxygen or source of oxygen are mixed upstream of the microchannel reactor. With the process illustrated in FIG. 3B, the ethylene and oxygen or source of oxygen are mixed in the microchannel reactor.
Figure 3B:
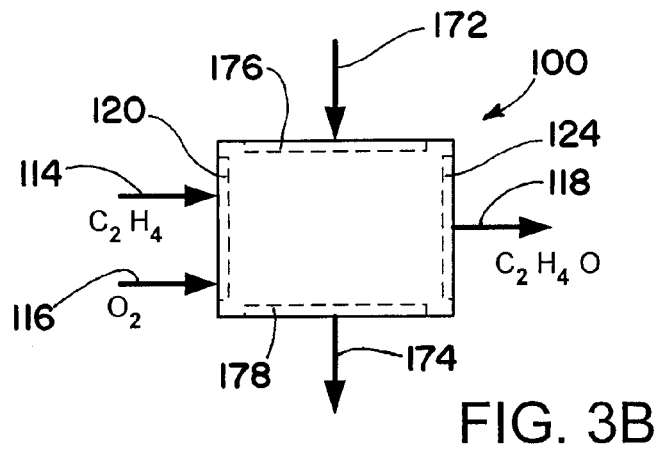

The inventive process for converting ethylene and oxygen to ethylene oxide may be conducted in the microchannel reactor 100 as illustrated in FIGS. 3A and 3B. Referring to FIG. 3A, a process feed stream or reactant composition comprising a mixture of ethylene and oxygen or source of oxygen flows, as indicated by arrow 112, into feed stream header or manifold 120, and from the feed stream header or manifold 120 into the one or more process microchannels 110 in the microchannel reactor 100. In the process microchannels 110, the reactants contact the catalyst and react to form the desired product which comprises ethylene oxide. The product flows out of the process microchannels 110 through product footer or manifold 124. The product flows from the product footer or manifold 124 out of the microchannel reactor 100, as indicated by arrow 118.

Alternatively, referring to FIG. 3B, the microchannel reactor 100 may comprise one or more process microchannels and one or more adjacent reactant stream channels. Each process microchannel and adjacent reactant stream channel may have a common wall with a plurality of openings in the common wall. The ethylene may flow into the header 120, as indicated by arrow 114, and from the header 120 into the one or more process microchannels in the microchannel reactor 100. The oxygen or source of oxygen may flow into the header 120, as indicated by arrow 116, and from the header 120 into the one or more reactant stream channels in the microchannel reactor 100. The oxygen or source of oxygen may then flow from each reactant stream channel through the openings in the common walls between the reactant stream channels and process microchannels into the adjacent process microchannels. Alternatively, the oxygen may flow directly into the one or more process microchannels in the microchannel reactor 100, and the ethylene may flow into each of the one or more reactant stream channels in the microchannel reactor 100 and from there into the adjacent process microchannels. The reactant flowing directly into the process microchannels may be referred to as a first reactant, and the reactant flowing into the adjacent reactant stream channels and then into the process microchannels may be referred to as a second reactant. In the process microchannels the ethylene and oxygen or source of oxygen contact each other and the catalyst and react to form the desired product comprising ethylene oxide. The product flows out of the process microchannels through product footer or manifold 124, and from product footer or manifold 124 out of the microchannel reactor 100, as indicated by arrow 118.

Although an advantage of the inventive process is that a high level of conversion to the desired product can be obtained with one pass through the microchannel reactor, in one embodiment, one or more unreacted reactants may be separated from the ethylene oxide in the product composition using conventional or microchannel techniques and recycled back through the microchannel reactor 100. The unreacted reactants may be recycled through the microchannel reactor 100 any number of times, for example, one, two, three, four times, etc.

The reactants may be preheated prior to entering the microchannel reactor 100. The reactants may be preheated to the average temperature employed in reaction zone of the one or more process microchannels used in the microchannel reactor. The reaction process is exothermic. In order to control the reaction, heat is transferred from the process microchannels to a heat exchange medium. That is, during the inventive process the process microchannels are cooled using a heat exchange medium. The heat exchange medium may comprise a heat exchange fluid in one or more heat exchange channels. The heat channels may be adjacent to and/or in thermal contact with the process microchannels. Referring to FIGS. 3A and 3B, the heat exchange fluid flows into heat exchange manifold 176, as indicated by arrow 172, and from the heat exchange manifold 176 through the heat exchange channels 170 in the microchannel reactor 100. The heat exchange fluid absorbs is heat from the process microchannels, and then flows out of the heat exchange channels into and through the heat exchange manifold 178, and then from the heat exchange manifold 178 out of the microchannel reactor 100, as indicated by arrow 174. Heat transfer between the process fluids and heat exchange fluid may be effected using convective heat transfer. In one embodiment, heat transfer may be enhanced using a heat exchange fluid wherein the heat exchange fluid undergoes an endothermic reaction and/or a full or partial phase change (e.g., partial boiling). Multiple heat exchange zones may be employed along the length of the process microchannels 110 to provide for different temperatures at different locations along the axial lengths of the process microchannels. Also, at the end of the reaction the product may be quenched in order to reduce or eliminate the formation of undesired by-products. Quenching may be effected in the microchannel reactor 100 or downstream of the microchannel reactor.

Figure 4:
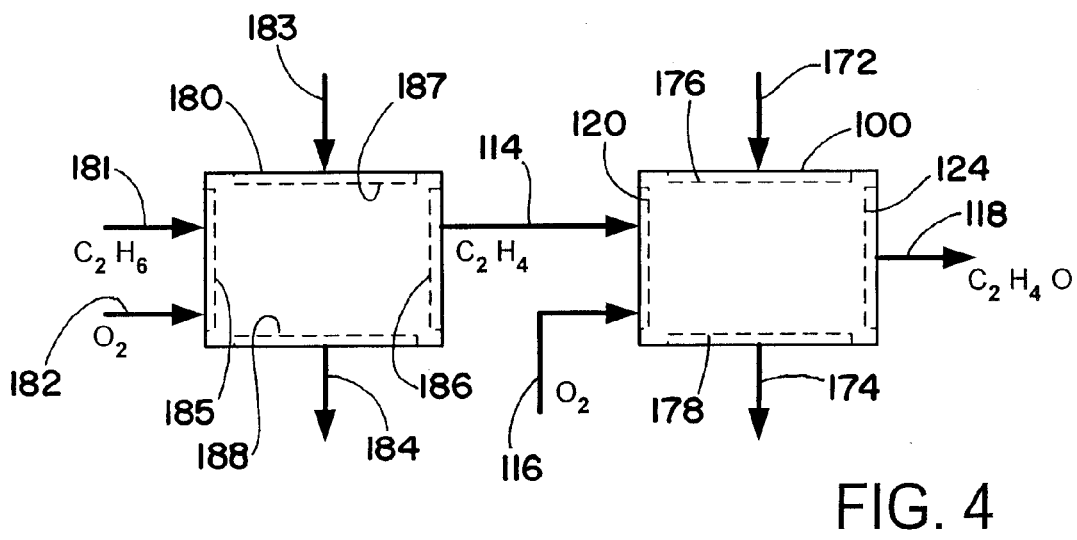
FIG. 4 is a flow sheet for a process that is similar to the process illustrated in FIG. 3B with the exception that the ethylene is formed upstream of the ethylene oxide forming microchannel reactor. The ethylene may be formed in a conventional reactor or an ethylene forming microchannel reactor. The process for forming the ethylene may be an oxidative dehydrogenation (ODH) reaction process. Alternatively, the ethylene forming process may comprise a catalytic dehydrogenation process or a thermal cracking process. In the ODH reaction process, ethane is reacted with oxygen in the presence of an ODH catalyst to form ethylene. The ODH reaction process is exothermic. A heat exchange fluid is used to control temperature.

The ethylene may be formed using oxidative dehydrogenation or thermal cracking. The ethylene may be formed in a reactor positioned upstream of the microchannel reactor used to convert the ethylene to ethylene oxide. This is illustrated in FIG. 4. Referring to FIG. 4, ethylene is formed in reactor 180 upstream of the ethylene oxide forming microchannel reactor 100. The reactor 180 may be a conventional reactor or it may be a microchannel reactor. Ethane and oxygen or a source of oxygen enter the reactor 180, as indicated by arrows 181 and 182, and undergo reaction in the reactor 180 to form ethylene. The ethylene flows out of the reactor 180 as indicated by arrow 114. The ethylene flows into microchannel reactor 100 where it is converted to ethylene oxide as discussed above. The ethylene forming process illustrated in FIG. 4 is an oxidative dehydrogenation (ODH) reaction process. This process is exothermic. The reaction is cooled using a heat exchange fluid which flows through the reactor 180 as indicated by arrows 183 and 184. The reactor 180 may comprise a microchannel reactor similar to the microchannel reactor 100 illustrated in FIG. 2. This microchannel reactor may comprise a plurality of process microchannels and heat exchange channels stacked one above the other. The microchannel reactor 180 may have a feed stream header or manifold 185 to provide for the flow of the reactants into the process microchannels, a product footer or manifold 186 to provide for the flow of product out of the process microchannels, a heat exchange inlet manifold 187 to provide for the flow of heat exchange fluid into the heat exchange channels, and a heat exchange outlet manifold 188 to provide for the flow of heat exchange fluid out of the heat exchange channels. Alternatively, the ethylene forming process may comprise a catalytic dehydrogenation process or a thermal cracking process.

Figure 5:
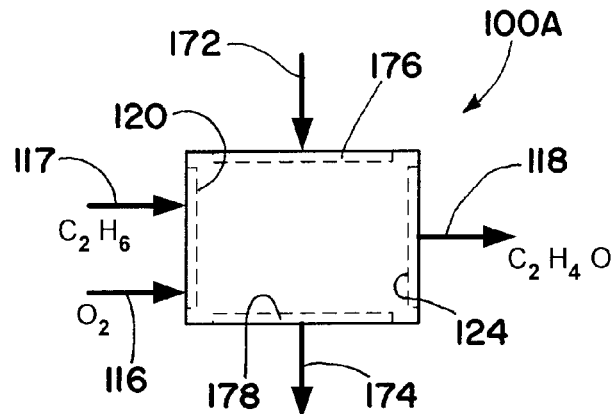
FIG. 5 is a flow sheet of a process for converting ethane to ethylene oxide. The process is similar to the process illustrated in FIG. 4 with the exception that the process for converting ethane to ethylene and the process for converting ethylene to ethylene oxide are conducted in the same microchannel reactor. The microchannel reactor contains one or more process microchannels wherein an ethylene forming catalyst is positioned upstream of an olefin epoxidation catalyst. Ethane and oxygen or a source of oxygen contact the ethylene forming catalyst and react to form ethylene. The ethylene and additional oxygen then contact the olefin epoxidation catalyst and react to form ethylene oxide. A heat exchange fluid is used to control temperature.

In one embodiment, a first portion of the microchannel reactor may be used for ethylene formation using thermal or catalytic cracking, followed by cooling in a second portion of the microchannel reactor, followed by conversion of the ethylene to form ethylene oxide in a third portion of the microchannel reactor. In one embodiment, oxidative dehydrogenation may be used in the microchannel reactor to form ethylene from ethane, followed by cooling, and then mixing the ethylene with oxygen and contacting a catalyst to form the ethylene oxide. This is illustrated in FIG. 5. The process shown in FIG. 5 is similar to the process illustrated in FIG. 4 with the exception that the process for converting ethane to ethylene and the process for converting ethylene to ethylene oxide are both conducted in microchannel reactor 100A. Microchannel reactor 100A is similar to the microchannel reactor 100 illustrated in FIG. 2. This microchannel reactor may comprise a plurality of process microchannels and heat exchange channels stacked one above the other. The microchannel reactor 100A may have a feed stream header or manifold 120 to provide for the flow of the reactants into the process microchannels, and a product footer or manifold 124 to provide for the flow of product out of the process microchannels. The process microchannels contain an ethylene forming catalyst and an olefin epoxidation catalyst, the ethylene forming catalyst being positioned upstream of the olefin epoxidation catalyst. Ethane and oxygen or a source of oxygen contact the ethylene forming catalyst and react to form ethylene. The product ethylene may be cooled. The ethylene and oxygen or source of oxygen may then contact the olefin epoxidation catalyst and react to form ethylene oxide. A heat exchange fluid is used to control temperature. The heat exchange fluid flows into heat exchange manifold 176, as indicated by arrow 172, and from heat exchange to manifold 176 through the heat exchange channels 170 in the microchannel reactor 100. The heat exchange fluid absorbs heat from the process microchannels, and then flows out of the heat exchange channels into and through the heat exchange manifold 178, and from the heat exchange manifold out of the microchannel reactor 100A, as indicated by arrow 174.

Figure 6A:
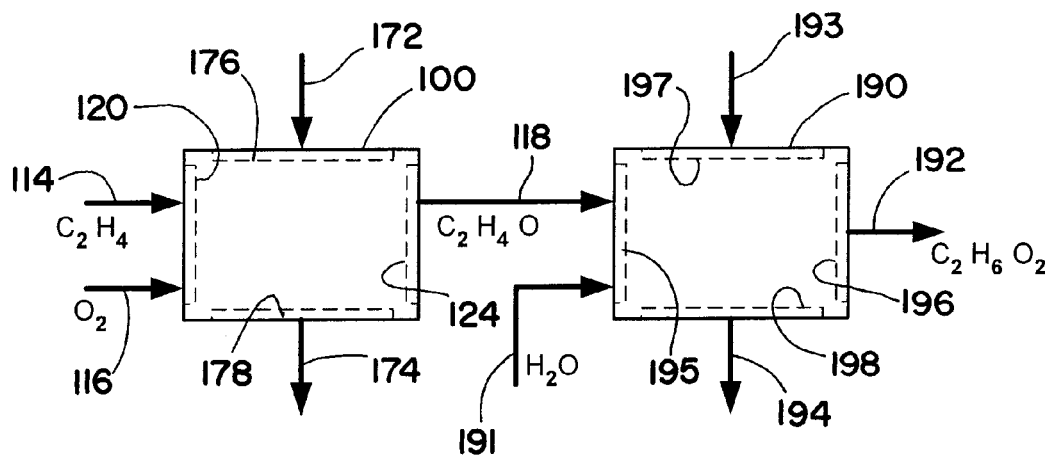
FIGS. 6A and 6B are flow sheets of a process for converting ethylene and oxygen or a source of oxygen to ethylene oxide and then subsequently converting the ethylene oxide to ethylene glycol.
Figure 6B:
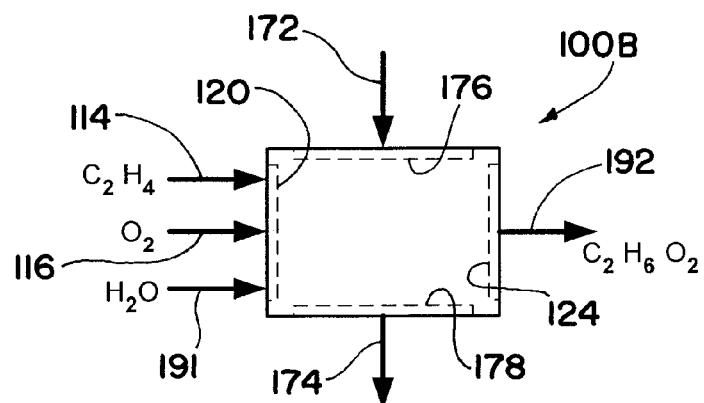

The ethylene oxide that is formed in the microchannel reactor 100 may be converted to ethylene glycol. This is illustrated in FIGS. 6A and 6B. Referring to FIG. 6A, the ethylene oxide formed in microchannel reactor 100 is converted to ethylene glycol by reacting with water in glycol forming reactor 190. The glycol forming reactor 190 is downstream from the ethylene oxide forming microchannel reactor 100. The glycol forming reactor 190 may be a conventional reactor or it may be a microchannel reactor. The microchannel reactor 190 may comprise a plurality of process microchannels and heat exchange channels stacked one above the other. The microchannel reactor 190 may have a feed stream header or manifold 195 to provide for the flow of the reactants into the process microchannels, a product footer or manifold 196 to provide for the flow of product out of the process microchannels, a heat exchange inlet manifold 197 to provide for the flow of heat exchange fluid into the heat exchange channels, and a heat exchange outlet manifold 198 to provide for the flow of heat exchange fluid out of the heat exchange channels. The heat exchange fluid flowing through the reactor may be used to heat or cool the reaction. The conversion to ethylene glycol may be carried out by reacting the ethylene oxide with water in a thermal process and/or in a catalytic process. The catalyst may be an acid catalyst or a basic catalyst. The catalyst may comprise sulfuric acid. The reaction may comprise a liquid phase reaction or a gas phase reaction.

The process shown in FIG. 6B is similar to the process illustrated in FIG. 6A with the exception that the process for converting ethylene to ethylene oxide and the process for converting ethylene oxide to ethylene glycol are both conducted in microchannel reactor 100B. Microchannel reactor 100B is similar to the microchannel reactor 100 illustrated in FIG. 2. This microchannel reactor may comprise a plurality of process microchannels and heat exchange channels stacked one above the other. The microchannel reactor 100B may have a feed stream header or manifold 120 to provide for the flow of the reactants into the process microchannels, and a product footer or manifold 124 to provide for the flow of product out of the process microchannels. The process microchannels may contain an olefin epoxidation catalyst and a glycol forming catalyst, the olefin epoxidation catalyst being positioned upstream of the glycol forming catalyst. Ethylene and oxygen or a source of oxygen contact the olefin epoxidation catalyst and react to form ethylene oxide. The ethylene oxide and water may then contact the glycol forming catalyst and react to form ethylene glycol. The water enters the microchannel reactor, as indicated by arrow 191. The water may be added to the one or more process microchannels downstream of the olefin epoxidation catalyst using staged addition. The ethylene glycol flows out of the microchannel reactor 100B as indicated by arrow 192. A heat exchange fluid is used to control temperature. The heat exchange fluid flows into heat exchange manifold 176, as indicated by arrow 172, and from heat exchange manifold 176 through the heat exchange channels 170 in the microchannel reactor 100B. The heat exchange fluid absorbs heat from the process microchannels, and then flows out of the heat exchange channels into and through the heat exchange manifold 178, and from the heat exchange manifold out of the microchannel reactor 100B, as indicated by arrow 174.

The microchannel reactor may be used in combination with one or more storage vessels, pumps, compressors, valves, microprocessors, flow control devices, and the like, which are not shown in the drawings, but would be apparent to those skilled in the art.

The microchannel reactor 100 may contain a plurality of repeating units, each of which may include one or more ethylene oxide forming process microchannels and one or more heat exchange channels. When staged addition is used with the inventive process, the repeating units may contain one or more reactant stream channels positioned adjacent to each process microchannel. The repeating units that may be used include repeating units 200, 200A, 200B, 200C, 200D, 200E, 200F and 200G illustrated in FIGS. 9-14 and 26-27, respectively. The microchannel reactor 100 may comprise from 1 to about 1000 of the repeating units 200, 200A, 200B, 200C, 200D, 200E, 200F or 200G, and in one embodiment from about 10 to about 500 of such repeating units. The catalyst used in the repeating units 200, 200A, 200B, 200C, 200D, 200E, 200F or 200G may be in any form, including the various catalyst structured forms described below.

Repeating unit 200 is illustrated in FIG. 9. Referring to FIG. 9, process microchannel 210 is positioned adjacent to heat exchange channel 230. The heat exchange channel 230 may be a microchannel. A common wall 232 separates the process microchannel 210 and the heat exchange channel 230. The common wall 232 may be referred to as a heat transfer wall. The process microchannel 210 includes reaction zone 212. A catalyst (not shown in the drawing) is positioned in the reaction zone 212. The reactants or reactant composition (i.e., ethylene and oxygen or source of oxygen) flow into the reaction zone 212, as indicated by arrow 214, contact the catalyst in reaction zone 212, and react to form the desired product. The product comprises ethylene oxide. The product flows out of the process microchannel 210 as indicated by arrow 216. Heat exchange fluid flows in the heat exchange channel 230 in a direction that is cross-current to the flow of reactants and product in the process microchannel 210 (that is, into or out of the page, as illustrated in FIG. 9). The ethylene oxide-forming reaction conducted in the process microchannel 210 is exothermic and the heat exchange fluid provides cooling for the reaction. Alternatively, the heat exchange fluid may flow through the heat exchange channel 230 in a direction that is counter-current to the flow of reactants and product in the process microchannel 210 or co-current to the flow of the reactants and product in the process microchannel 210.

Repeating unit 200A is illustrated in FIG. 10. Referring to FIG. 10, process microchannel 210 is positioned adjacent to reactant stream channel 250. The process microchannel 210 includes reaction zone 212. The process microchannel 210 and reactant stream channel 250 have a common wall 252. The common wall 252 has a plurality of openings 254 that are of sufficient dimension to permit the flow of one of the reactants, that is, either ethylene or oxygen or oxygen source, preferably oxygen or oxygen source, from the reactant stream channel 250 into the process microchannel 210 as indicated by arrows 256. This reactant may be referred to as a staged addition reactant or the second reactant. The openings 254 may be referred to as apertures. The section 258 in the common wall 252 containing the openings 254 may be referred to as an apertured section. Heat exchange channel 230 is positioned adjacent to the process microchannel 210. The heat exchange channel 230 and the process microchannel 210 have a common wall 232. The common wall 232 may be referred to as a heat transfer wall. In operation, the first reactant, which preferably comprises ethylene, flows into the process microchannel 210 as indicated by arrow 217. The second reactant (i.e., the staged addition reactant), which preferably comprises oxygen or an oxygen source, flows into the reactant stream channel 250 as indicated by arrow 218, and from the reactant stream channel 250 through the openings 254 into the process microchannel 210. In the process microchannel 210, the reactants contact the catalyst in the reaction zone 212 and react to form the desired product which comprises ethylene oxide. The reaction is exothermic, and the heat exchange channel 230 provides cooling to control the temperature of the reaction. The heat exchange fluid may flow in the heat exchange channel 230 in a direction that is cross-current relative to the flow of reactants and product in the process microchannel 210. Alternatively, the heat exchange fluid may flow in a direction that is counter-current or co-current to the flow of reactants and product in the process microchannel 210.

Figure 11:
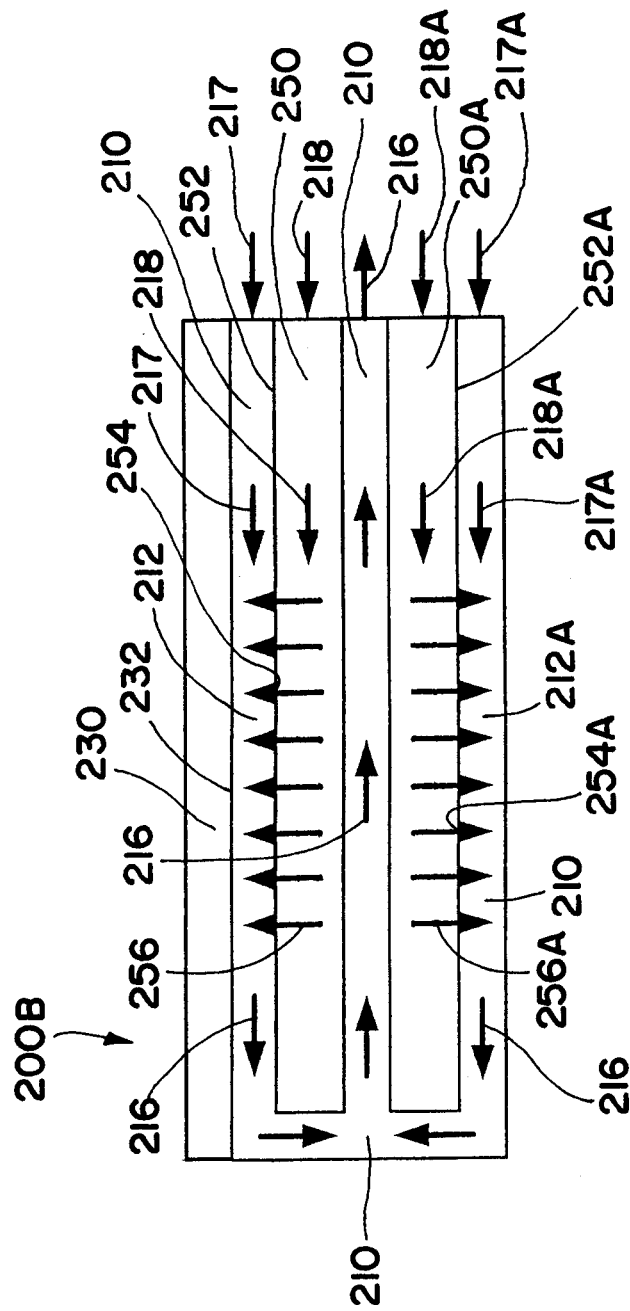

The repeating unit 200B illustrated in FIG. 11 is similar to the repeating unit 200A illustrated in FIG. 10, with the exception that the process microchannel 210 is an E-shaped microchannel which includes two reaction zones. Also, two adjacent reactant stream channels are used. With this embodiment, staged addition of the second reactant is provided for the reaction process. The process microchannel 210 has an E-shape with entrances indicated by arrows 217 and 217A and an outlet indicated by arrow 216. The process microchannel 210 includes reaction zones 212 and 212A. Reactant stream channels 250 and 250A are positioned between the legs of the E-shaped process microchannel 210. The reactant stream channel 250 and process microchannel 210 have a common wall 252 which contains a plurality of openings 254. The reactant stream channel 250A and the process microchannel 210 have a common wall 252A which contains a plurality of openings 254A. The first reactant, which preferably comprises ethylene, enters the process microchannel 210 as indicated by arrows 217 and 217A, and flows into the reaction zones 212 and 212A, respectively. The second reactant, which preferably comprises oxygen or a source of oxygen, enters the reactant stream channels 250 and 250A as indicated by arrows 218 and 218A, respectively. The second reactant flows from the reactant stream channels 250 and 250A to and through openings 254 and 254A into the reaction zones 212 and 212A, contacts the first reactant and the catalyst, and reacts to form the product. The product comprises ethylene oxide. The product flows out of the E-shaped process microchannel 210 as indicated by arrow 216. Heat exchange fluid flows in the heat exchange channel 230 in a direction that is cross-current relative to the flow of reactants and product in the process microchannel 210 and provides cooling for the exothermic reaction. Alternatively, the heat exchange fluid may flow in a direction that is co-current or counter-current relative to the flow of reactants and product in the reaction zones 212 and 212A.

Figure 12:
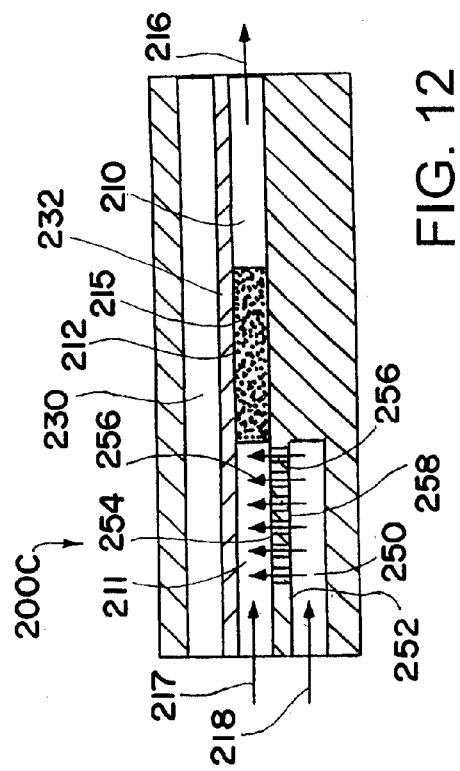

Repeating unit 200C is illustrated in FIG. 12. Referring to FIG. 12, repeating unit 200C comprises process microchannel 210, heat exchange channel 230, reactant stream channel 250, and apertured section 258. A common wall 252 separates process microchannel 210 and reactant stream channel 250. The apertured section 258, which contains openings 254, is positioned in common wall 252. The apertured section 258 extends partially along the axial length of process microchannel 210. The process microchannel 210 has a mixing zone 211, and a reaction zone 212. A catalyst 215 is positioned in the reaction zone 212. The mixing zone 211 is upstream from the reaction zone 212. The first reactant flows into process microchannel 210, as indicated by the arrow 217, and then into the mixing zone 211. The second reactant flows into reactant stream channel 250, as indicated by arrow 218, and from the reactant stream channel 250 through the openings 254 into mixing zone 211, as indicated by arrows 256. The first reactant and the second reactant contact each other in the mixing zone 211 and form a reactant mixture. The reactant mixture flows from the mixing zone 211 into the reaction zone 212, contacts the catalyst 215, and reacts to form the desired product which comprises ethylene oxide. The product flows out of the process microchannel 210, as indicated by arrow 216. Heat exchange fluid flows in heat exchange channel 230 in a direction that is cross-current to the flow of fluid flowing in process microchannel 210. Alternatively, the heat exchange fluid may flow in a direction that is counter-current or co-current to the flow of fluid in the process microchannel 210.

In an alternate embodiment of the repeating unit 200C illustrated in FIG. 12, a supplemental mixing zone may be provided in the process microchannel 210 between the mixing zone 211 and reaction zone 212. The residence time for mixing in the supplemental mixing zone may be defined using the sum of the total of the flow through the openings 254 and the flow of the first reactant in process microchannel 210, at standard conditions of temperature (i.e., 0° C.) and pressure (i.e., atmospheric pressure), and the volume defined by the process microchannel 210 between the end of the mixing zone 211 and the beginning of the reaction zone 212. This residence time for mixing in the supplemental mixing zone may be in the range up to about 500 milliseconds (ms), and in one embodiment from about 0.25 ms to about 500 ms, and in one embodiment from about 0.25 ms to about 250 ms, and in one embodiment from about 0.25 to about 50 ms, and in one embodiment from about 0.25 to about 2.5 ms.

Figure 13:
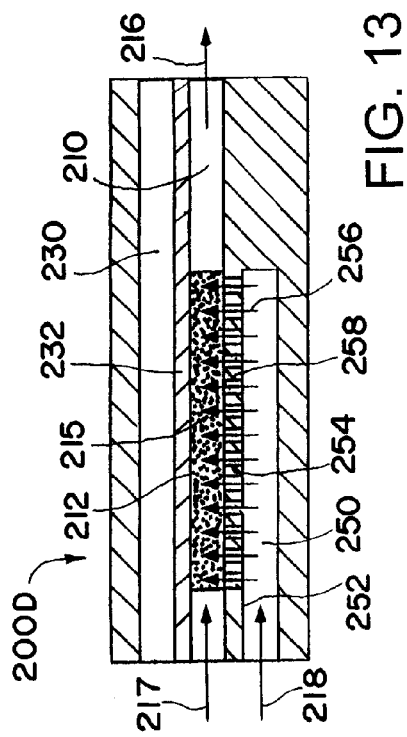

The repeating unit 200D illustrated in FIG. 13 is the same as the repeating unit 200C illustrated in FIG. 12 with the exception that the repeating unit 200D does not contain the separate mixing zone 211. With repeating unit 200D, the second reactant flows through the openings 254 into the reaction zone 212 where it contacts the first reactant and the catalyst 215, and reacts to form the desired product comprising ethylene oxide. The product then flows out of the process microchannel 210, as indicated by arrow 216.

Figure 14:
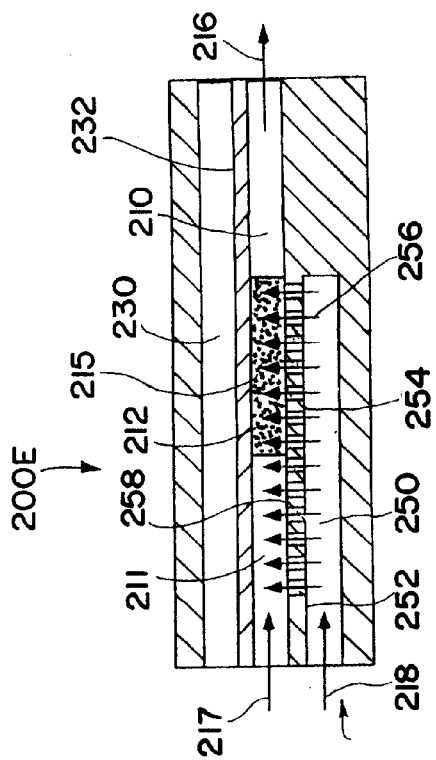

The repeating unit 200E illustrated in FIG. 14 is the same as the repeating unit 200C illustrated in FIG. 12 with the exception that part of the second reactant mixes with the first reactant in the mixing zone 211, and the remainder of the second reactant mixes with the resulting reactant mixture in the reaction zone 212. The amount of the second reactant that mixes with the first reactant in the mixing zone 211 may be from about 1% to about 99% by volume of the second reactant, and in one embodiment from about 5% to about 95% by volume, and in one embodiment from about 10% to about 90% by volume, and in one embodiment from about 20% to about 80% by volume, and in one embodiment from about 30% to about 70% by volume, and in one embodiment from about 40% to about 60% by volume of the second reactant. The remainder of the second reactant mixes with the resulting reactant mixture in the reaction zone 212.

Figure 26:
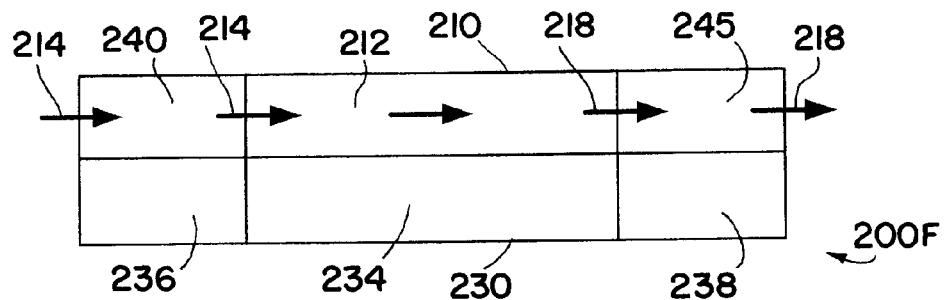
FIGS. 26 and 27 are schematic illustrations of repeating units that may be used in the microchannel reactor used with the inventive process. Each of these repeating units includes a section for preheating the reactants and a section for quenching the product.

The repeating unit 200F illustrated in FIG. 26 is the same as the repeating unit 200 in FIG. 9 with the exception that the process microchannel 210 illustrated in FIG. 26 includes a reaction zone 220, a preheating zone 240 and a quenching zone 245. The preheating zone 240 is upstream of the reaction zone 212. The quenching zone 245 is downstream of the reaction zone 212. The preheating zone 240 is heated by heating section 236. The reaction zone 212 is cooled by cooling section 234. The quenching zone 245 is cooled by cooling section 238. The heating section 236, and the cooling sections 234 and 238 may each comprise heat exchange channels with appropriate heat exchange fluids flowing in the heat exchange channels. The reactants enter the preheating section 240, as indicated by 214, and flow through the preheating section 240 where they are preheated to a desired temperature for entering the reaction zone 212. The reactants flow from the preheating section 240 into the reaction zone 212 where they undergo reaction to form the product. The product flows from the reaction zone 212 through the quenching zone 245 wherein the product is quenched. The product flows from the quenching zone 245 out of the process microchannel 210 as indicated by arrow 218.

Figure 27:
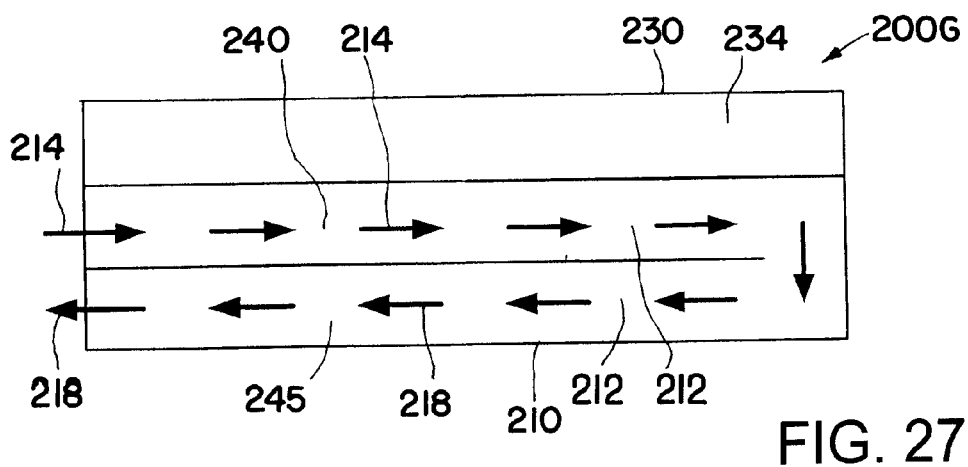

The repeating unit 200G illustrated in FIG. 27 is similar to the repeating unit 200F with the exception that the process mircochannel 210 is in the form of a U laying on its side. Also, the preheating zone 240 and the quenching zone 245 are adjacent to each other and exchange heat with each other. The reaction zone 212 of the process microchannel 210 is cooled by the cooling section 234 of heat exchange channel 230. The reactants enter the process microchannel 210 as indicated by arrow 214, flow through preheating section 240 where they are preheated and then through reaction zone 212 where the reactants undergo reaction to form the product. The product flows from the reaction zone 212 through the quenching zone 245 where the reaction is quenched. The product flows out of the process microchannel 210 as indicated by arrow 218. The relatively cool reactants flowing in the preheating zone 240 are heated by the relatively hot product flowing through the quenching zone 245. As a result, heat transfers from the quenching zone 245 to the preheating zone 240.

The repeating units 200F and 200G provide for quenching the product in the microchannel reactor 100. Alternatively, the product may be quenched downstream of the microchannel reactor 100. The product quenching may involve reducing the temperature of the product by at least about 200° C. within a period of up to about 500 milliseconds (ms). The temperature may be reduced by at least about 150° C., and in one embodiment at least about 100° C., within a time period of up to about 500 ms, and in one embodiment up to about 400 ms, and in one embodiment up to about 300 ms, and in one embodiment up to about 200 ms, and in one embodiment up to about 100 ms, and in one embodiment up to about 50 ms, and in one embodiment up to about 35 ms, and in one embodiment up to about 20 ms, and in one embodiment up to about 15 ms, and in one embodiment up to about 10 ms, and in one embodiment within a time period of up to about 5 ms. In one embodiment, the temperature may be reduced by up to about 200° C. within a time period of about 5 to about 100 ms, and in one embodiment about 10 to about 50 ms. The product may be quenched in the microchannel reactor as illustrated in FIGS. 26 and 27, or it may be quenched in a quenching device that is separate from the microchannel reactor. The quenching device may comprise a microchannel heat exchanger. The quenching device may comprise a heat exchanger that is adjacent to or interleaved with the product stream exiting the microchannel reactor. The quenching device may comprise a mixer capable of rapidly mixing the product with a secondary cooling fluid. The secondary cooling fluid may be a low temperature steam.

Alternatively, the quenching device may comprise a narrow gap or passageway for the process fluids to flow through. The gap or passageway may have a dimension equal to or below the quench diameter for the reaction. In this embodiment, the reaction may terminate as the reactants flow through the gap or passageway as a result of wall collisions. The gap or passageway may have a height or width of up to about 5 mm, and in one embodiment up to about 3 mm, and in one embodiment up to about 1 mm, and in one embodiment up to about 0.5 mm, and in one embodiment up to about 0.1 mm, and in one embodiment up to about 0.05 mm. This quenching device may comprise a microchannel or a plurality of parallel microchannels. This quenching device may comprise part of the process microchannels used with the inventive process downstream of the catalyst contained within the microchannels. The narrow gap or passageway may be used in conjunction with one or more of the other quenching devices (e.g., heat exchangers).

The heat exchange channels and reactant stream channels may be microchannels or they may have dimensions that would characterize them as not being microchannels. For example, these channels may have internal heights or widths up to about 50 mm, and in one embodiment up to about 25 mm, and in one embodiment up to about 15 mm. The process microchannels are microchannels. Each of the channels may have a cross-section having any shape, for example, a square, rectangle, circle, semi-circle, etc. Each microchannel may have an internal height of up to about 10 mm, and in one embodiment up to about 5 mm, and in one embodiment up to about 2 mm, and in one embodiment up to about 2 mm. In one embodiment, the height may be in the range of about 0.05 to about 10 mm, and in one embodiment from about 0.05 to about 5 mm, and in one embodiment from about 0.05 to about 2 mm, and in one embodiment about 0.05 to about 1.5 mm. The width is of each of these microchannels may be of any dimension, for example, up to about 3 meters, and in one embodiment from about 0.01 to about 3 meters, and in one embodiment about 0.1 to about 3 meters. The length of each microchannel may be of any dimension, for example, up to about 10 meters, and in one embodiment about 0.2 to about 10 meters, and in one embodiment from about 0.2 to about 6 meters, and in one embodiment from 0.2 to about 3 meters.

The process microchannels, heat exchange channels and reactant stream channels may have rectangular cross sections and be aligned in side-by-side vertically oriented planes or horizontally oriented stacked planes. These planes may be tilted at an inclined angle from the horizontal. These configurations may be referred to as parallel plate configurations. These channels may be arranged in modularized compact units for scale-up.

The microchannel reactor 100 may be made of any material that provides sufficient strength, dimensional stability and heat transfer characteristics to permit operation of the inventive process. These materials may include aluminum; titanium; nickel; copper; chromium; alloys of any of the foregoing metals; brass; steel; quartz; silicon; or a combination of two or more thereof.

The microchannel reactor 100 may be fabricated using known techniques including wire electrodischarge machining, conventional machining, laser cutting, photochemical machining, electrochemical machining, molding, water jet, stamping, etching (for example, chemical, photochemical or plasma etching) and combinations thereof.

The microchannel reactor 100 may be constructed by forming shims with portions removed that allow flow passage. A stack of shims may be assembled via diffusion bonding, laser welding, diffusion brazing, and similar methods to form an integrated device. The microchannel reactor may be assembled using a combination of shims or laminae and partial sheets or strips. In this method, the channels or void areas may be formed by assembling strips or partial sheets to reduce the amount of material required.

The microchannel reactor 100 may be constructed using waveforms in the form of right angled corrugated inserts. These inserts may be sandwiched between opposing planar sheets or shims. In this manner the microchannels may be defined on three sides by the corrugated insert and on the fourth side by one of the planar sheets. The process microchannels as well as the reactant stream channels and heat exchange channels may be formed in this manner. Microchannel reactors made using waveforms are disclosed in WO 2008/030467.

Figure 7:
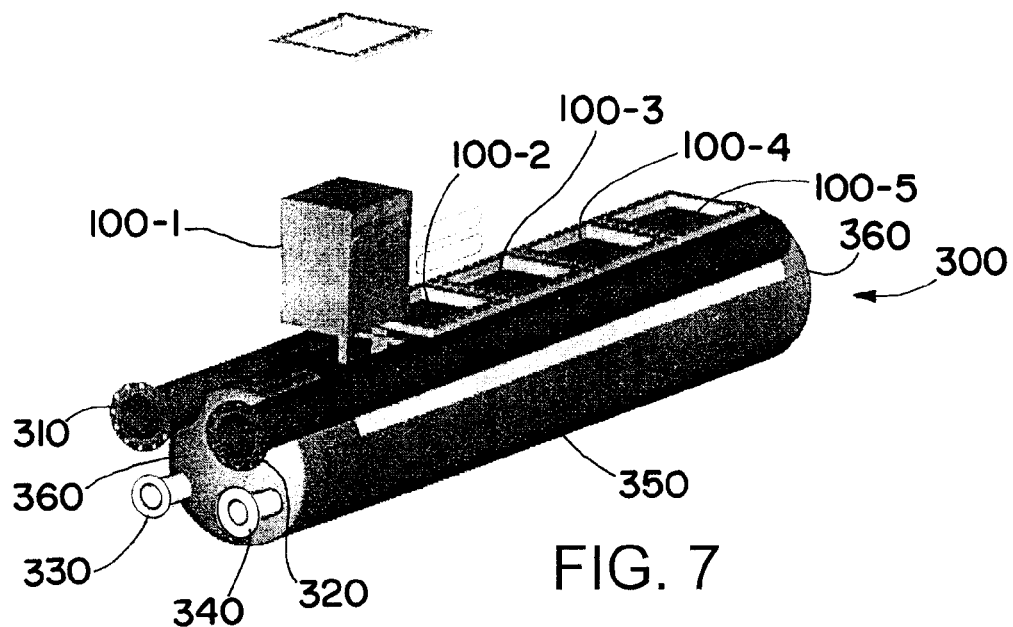
FIGS. 7 and 8 are schematic illustrations of a reaction vessel which may be used for housing a plurality of the microchannel reactors used with the inventive process.
Figure 8:
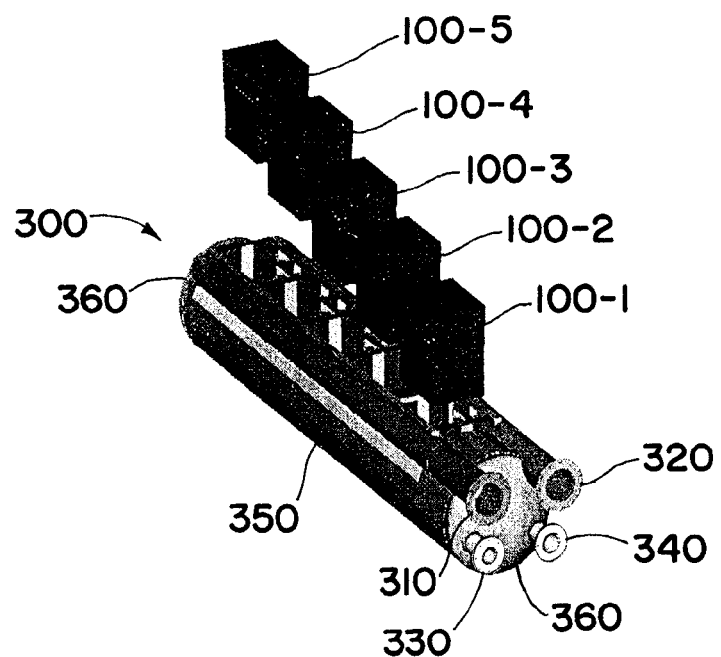

One or more of the microchannel reactors 100 may be housed in housing vessel 300 which is illustrated in FIGS. 7 and 8. Referring to FIGS. 7 and 8, the vessel 300 contains five microchannel reactors 100. These are identified in FIGS. 7 and 8 as microchannel reactors 100-1, 100-2, 100-3, 100-4 and 100-5. Although five microchannel reactors 100 are disclosed in the drawings, it will be understood that the vessel 300 may contain any desired number of microchannel reactors 100. For example, the vessel 300 may contain from about 1 to about 1000 microchannel reactors 100, and in one embodiment from 1 to about 750, and in one embodiment from 1 to about 500, and in one embodiment from 1 to about 250, and in one embodiment from 1 to about 100, and in one embodiment from about 1 to about 50, and in one embodiment from 1 to about 20 microchannel reactors 100. The vessel 300 may be a pressurizable vessel. The vessel 300 includes inlets 310 and 320, and outlets 330 and 340. The inlet 310 is connected to a manifold which is provided for flowing reactants or process feed to the process microchannels in the microchannel reactors 100. The inlet 320 is connected to a manifold which is provided for flowing heat exchange fluid to heat exchange channels in the microchannel reactors 100. The outlet 330 is connected to a manifold which provides for the flow of product from the process microchannels in the microchannel reactors 100. The outlet 340 is connected to a manifold to provide for the flow of the heat exchange fluid out of the heat exchange channels in the microchannel reactors 100.

The housing vessel 300 may be constructed using any suitable material sufficient for operating under the pressures and temperatures required for operating the microchannel reactors 100. For example, the shell 350 and heads 360 of the vessel 300 may be constructed of cast steel. The flanges, couplings and pipes may be constructed of 316 stainless steel. The vessel 300 may have any desired diameter, for example, from about 10 to about 1000 cm, and in one embodiment from about 50 to about 300 cm. The axial length of the vessel 300 may be of any desired value, for example, from about 0.5 to about 50 meters, and in one embodiment from about 1 to about 20 meters.

In the design and operation of the microchannel reactor 100 it may be advantageous to provide a tailored heat exchange profile along the length of the process microchannels in order to optimize the reaction. This may be accomplished by matching the local release of heat given off by the ethylene oxide-forming reaction conducted in the process microchannels with heat removal or cooling provided by heat exchange fluid in heat exchange channels in the microchannel reactor. The extent of the ethylene oxide-forming reaction and the consequent heat release provided by the reaction may be higher in the front or upstream sections of the reaction zones in the process microchannels as compared to the back or downstream sections of the reaction zones. Consequently, the matching cooling requirements may be higher in the upstream section of the reaction zones as compared to the downstream sections of the reaction zones. Tailored heat exchange may be accomplished by providing more heat exchange or cooling channels, and consequently the flow of more heat exchange or cooling fluid, in thermal contact with upstream sections of the reaction zones in the process microchannels as compared to the downstream sections of the reaction zones. Alternatively or additionally, a tailored heat exchange profile may be provided by varying the flow rate of heat exchange fluid in the heat exchange channels. In areas where additional heat exchange or cooling is desired, the flow rate of the heat exchange fluid may be increased as compared to areas where less heat exchange or cooling is required. For example, a higher rate of flow of heat exchange fluid may be advantageous in the heat exchange channels in thermal contact with the upstream sections of the reaction zones in the process microchannels as compared to the heat exchange channels in thermal contact with the downstream sections of the reaction zones. Heat transfer from the process microchannels to the heat exchange channels may be designed for optimum performance by selecting optimum heat exchange channel dimensions and/or the rate of flow of heat exchange fluid per individual or groups of heat exchange channels. Additional design alternatives for tailoring heat exchange may relate to the selection and design of the ethylene oxide-forming catalyst (such as, particle size, catalyst formulation, packing density, use of a graded catalyst, or other chemical or physical characteristics) at specific locations within the process microchannels. These design alternatives may impact both heat release from the process microchannels as well as heat transfer to the heat exchange fluid. Temperature differentials between the process microchannels and the heat exchange channels, which may provide the driving force for heat transfer, may be constant or may vary along the length of the process microchannels.

The process microchannels and/or heat exchange channels may contain one or more surface features in the form of depressions in and/or projections from one or more interior walls or interior structures of the process microchannels and/or heat exchange channels. Examples are shown in FIGS. 15, 16 and 25. The surface features may be used to disrupt the flow of fluid flowing in the channels. These disruptions in flow may enhance mixing and/or heat transfer. The surface features may be in the form of patterned surfaces. The microchannel reactors may be made by laminating a plurality of shims together. One or both major surfaces of the shims may contain surface features. Alternatively, the microchannel reactors may be assembled using some sheets or shims and some strips, or partial sheets to reduce the total amount of metal required to construct the device. In one embodiment, a shim containing surface features may be paired (on opposite sides of a microchannel) with another shim containing surface features. Pairing may create better mixing or heat transfer enhancement as compared to channels with surface features on only one major surface. In one embodiment, the patterning may comprise diagonal recesses that are disposed over substantially the entire width of a microchannel surface. The patterned surface feature area of a wall may occupy part of or the entire length of a microchannel surface. In one embodiment, surface features may be positioned over at least about 10%, and in one embodiment at least about 20%, and in one embodiment at least about 50%, and in one embodiment at least about 80% of the length of a channel surface. Each diagonal recess may comprise one or more angles relative to the flow direction. Successive recessed surface features may comprise similar or alternate angles relative to other recessed surface features.

In embodiments wherein surface features may be positioned on or in more than one microchannel wall, the surface features on or in one wall may have the same (or similar) pattern as found on a second wall, but rotated about the centerline of the main channel mean bulk flow direction. In embodiments wherein surface features may be on or in opposite walls, the surface features on or in one wall may be approximately mirror images of the features on the opposite wall. In embodiments wherein surface features are on or in more than one wall, the surface features on or in one wall may be the same (or similar) pattern as found on a second wall, but rotated about an axis which is orthogonal to the main channel mean bulk flow direction. In other words, the surface features may be flipped 180 degrees relative to the main channel mean bulk flow direction and rotated about the centerline of the main channel mean bulk flow. The surface features on or in opposing or adjacent walls may or may not be aligned directly with one another, but may be repeated continuously along the wall for at least part of the length of the wall. Surface features may be positioned on three or more interior surfaces of a channel. For the case of channel geometries with three or fewer sides, such as triangular, oval, elliptical, circular, and the like, the surface features may cover from about 20% to about 100% of the perimeter of the microchannel.

In one embodiment, a patterned surface may comprise multiple patterns stacked on top of each other. A pattern or array of holes may be placed adjacent to a heat transfer wall and a second pattern, such as a diagonal array of surface features may be stacked on top and adjacent to an open channel for flow. A sheet adjacent to an open gap may have patterning through the thickness of the sheet such that flow may pass through the sheet into an underlying pattern. Flow may occur as a result of advection or diffusion. As an example, a first sheet with an array of through holes may be placed over a heat transfer wall, and a second sheet with an array of diagonal through slots may be positioned on the first sheet. This may create more surface area for adhering a catalyst. In one embodiment, the pattern may be repeated on at least one other wall of the process microchannel. The patterns may be offset on opposing walls. The innermost patterned surfaces (those surfaces bounding a flow channel) may contain a pattern such as a diagonal array. The diagonal arrays may be oriented both "with" the direction of flow or one side oriented with the direction of flow and the opposing side oriented "against" the direction of flow. By varying surface features on opposing walls, different flow fields and degrees of vorticity may be created in the fluid that travels down the center and open gap.

The surface features may be oriented at angles relative to the direction of flow is through the channels. The surface features may be aligned at an angle from about 1° to about 89°, and in one embodiment from about 30° to about 75°, relative to the direction of flow. The angle of orientation may be an oblique angle. The angled surface features may be aligned toward the direction of flow or against the direction of flow. The flow of fluid in contact with the surface features may force some of the fluid into depressions in the surface features, while other fluids may flow above the surface features. Flow within the surface features may conform with the surface feature and be at an angle to the direction of the bulk flow in the channel. As fluid exits the surface features it may exert momentum in the x and y direction for an x,y,z coordinate system wherein the bulk flow is in the z direction. This may result in a churning or rotation in the flow of the fluids. This pattern may be helpful for mixing.

Two or more surface feature regions within the process microchannels may be placed in series such that mixing of the fluids may be accomplished using a first surface feature region, followed by at least one second surface feature region where a different flow pattern may be used.

The surface features may have two or more layers stacked on top of each other or intertwined in a three-dimensional pattern. The pattern in each discrete layer may be the same or different. Flow may rotate or advect in each layer or only in one layer. Sub-layers, which may not be adjacent to the bulk flow path of the channel, may be used to create additional surface area. The flow may rotate in the first level of surface features and diffuse molecularly into the second or more sublayers to promote reaction. Three-dimensional surface features may be made via metal casting, photochemical machining, laser cutting, etching, ablation, or other processes where varying patterns may be broken into discrete planes as if stacked on top of one another. Three-dimensional surface features may be provided adjacent to the bulk flow path within the microchannel where the surface features have different depths, shapes, and/or locations accompanied by sub-features with patterns of varying depths, shapes and/or locations.

An example of a three-dimensional surface feature structure may comprise recessed oblique angles or chevrons at the interface adjacent the bulk flow path of the microchannel. Beneath the chevrons there may be a series of three-dimensional structures that connect to the surface features adjacent to the bulk flow path but are made from structures of assorted shapes, depths, and/or locations. It may be further advantageous to provide sublayer passages that do not directly fall beneath an open surface feature that is adjacent to the bulk flow path within the microchannel but rather connect through one or more tortuous two-dimensional or three-dimensional passages. This approach may be advantageous for creating tailored residence time distributions in the microchannels, where it may be desirable to have a wider versus more narrow residence time distribution.

The length and width of a surface feature may be defined in the same way as the length and width of a channel. The depth may be the distance which the surface feature sinks into or rises above the microchannel surface. The depth of the surface features may correspond to the direction of stacking a stacked and bonded microchannel device with surface features formed on or in the sheet surfaces. The dimensions for the surface features may refer the maximum dimension of a surface feature; for example the depth of a rounded groove may refer to the maximum depth, that is, the depth at the bottom of the groove.

The surface features may have depths that are up to about 5 mm, and in one embodiment up to about 2 mm, and in one embodiment in the range from about 0.01 to about 5 mm, and in one embodiment in the range from about 0.01 to about 2 mm, and in one embodiment in the range from about 0.01 mm to about 1 mm. The width of the surface features may be sufficient to nearly span the microchannel width (for example, herringbone designs), but in one embodiment (such as fill features) may span about 60% or less of the width of the microchannel, and in one embodiment about 50% or less, and in one embodiment about 40% or less, and in one embodiment from about 0.1% to about 60% of the microchannel width, and in one embodiment from about 0.1% to about 50% of the microchannel width, and in one embodiment from about 0.1% to about 40% of the microchannel width. The width of the surface features may be in the range from about 0.05 mm to about 100 cm, and in one embodiment in the range from about 0.5 mm to about 5 cm, and in one embodiment in the range from about 1 to about 2 cm.

Multiple surface features or regions of surface features may be included within a channel, including surface features that recess at different depths into one or more microchannel walls. The spacing between recesses may be in the range from about 0.01 mm to about 10 mm, and in one embodiment in the range from about 0.1 to about 1 mm. The surface features may be present throughout the is entire length of a microchannel or in portions or regions of the channel. The portion or region having surface features may be intermittent so as to promote a desired mixing or unit operation (for example, separation, cooling, etc.) in tailored zones. For example, a one-centimeter section of a channel may have a tightly spaced array of surface features, followed by four centimeters of a flat channel without surface features, followed by a two-centimeter section of loosely spaced surface features. The term "loosely spaced surface features" may be used to refer to surface features with a pitch or feature to feature distance that is more than about five times the width of the surface feature.

The surface features may be positioned in one or more surface feature regions that extend substantially over the entire axial length of a channel. In one embodiment, a channel may have surface features extending over about 50% or less of its axial length, and in one embodiment over about 20% or less of its axial length. In one embodiment, the surface features may extend over about 10% to about 100% of the axial length of the channel, and in one embodiment from about 20% to about 90%, and in one embodiment from about 30% to about 80%, and in one embodiment from about 40% to about 60% of the axial length of a channel.

Each surface feature leg may be at an oblique angle relative to the bulk flow direction. The feature span length or span may be defined as being normal to the feature orientation. As an example, one surface feature may be a diagonal depression at a 45 degree angle relative to a plane orthogonal to the mean direction of bulk flow in the main channel with a 0.38 mm opening or span or feature span length and a feature run length of 5.6 mm. The run length may be the distance from one end to the other end of the surface feature in the longest direction, whereas the span or feature span length may be in the shortest direction (that is not depth). The surface feature depth may be the distance way from the main channel. For surface features with a nonuniform width (span), the span may be the average span averaged over the run length.

A surface feature may comprise a recess or a protrusion based on the projected area at the base of the surface feature or the top of the surface feature. If the area at the top of the surface feature is the same or exceeds the area at the base of the surface feature, then the surface feature may be considered to be recessed. If the area at the base of the surface feature exceeds the area at the top of the surface feature, then it may be considered to be protruded. For this description, the surface features may be described as recessed although it is to be understood that by changing the aspect ratio of the surface feature it may be alternatively defined as a protrusion. For a process microchannel defined by walls that intersect only the tops of the surface features, especially for a flat channel, all surface features may be defined as recessed and it is to be understood that a similar channel could be created by protruding surface features from the base of a channel with a cross section that includes the base of the surface features.

The process microchannels and/or heat exchange channels may have at least about 20%, and in one embodiment at least about 35%, and in one embodiment at least about 50%, and in one embodiment at least about 70%, and in one embodiment at least about 90% of the interior surface of the channel (measured in cross-section perpendicular to length; i.e., perpendicular to the direction of net flow through the channel) that contains surface features. The surface features may cover a continuous stretch of at least about 1 cm, and in one embodiment at least about 5 cm. In the case of an enclosed channel, the percentage of surface feature coverage may be the portion of a cross-section covered with surface features as compared to an enclosed channel that extends uniformly from either the base or the top of the surface feature or a constant value in-between. The latter may be a flat channel. For example, if a channel has patterned top and bottom surfaces that are each 0.9 cm across (wide) and unpatterned side walls that are 0.1 cm high, then 90% of the surface of the channel would contain surface features.

The process microchannel may be enclosed on all sides, and in one embodiment the channel may have a generally square or rectangular cross-section (in the case of rectangular channel, surface feature patterning may be positioned on both major faces). For a generally square or rectangular channel, the channel may be enclosed on only two or three sides and only the two or three walled sides may be used in the above described calculation of percentage surface features. In one embodiment, the surface features may be positioned on cylindrical channels with either constant or varying cross section in the axial direction.

Each of the surface feature patterns may be repeated along one face of the channel, with variable or regular spacing between the surface features in the channel bulk flow direction. Some embodiments may have only a single leg to each surface feature, while other embodiments may have multiple legs (two, three, or more). For a wide-width channel, multiple surface features or columns of repeated surface features may be placed adjacent to one another across the width of the channel. For each of the surface feature patterns, the feature depth, width, span, and spacing may be variable or constant as the pattern is repeated along the bulk flow direction in the main channel. Also, surface feature geometries having an apex connecting two legs at different angles may have alternate embodiments in which the surface feature legs may not be connected at the apex.

An advantage of the inventive process, at least in one embodiment, is that the gap distances between the process microchannels, optional reactant stream channels, and heat exchange channels may be the same whether the process is intended for laboratory or pilot plant scale or for full production scale. As a result, the dispersion of the second reactant into the reaction mixture used in the inventive process may be substantially the same whether the microchannel reactor is built on a laboratory, pilot plant scale or as a full scale plant unit.

The catalyst may be segregated into separate reaction zones in the process microchannels in the direction of flow through the process microchannels. The same or different catalyst or catalyst composition may be used in each reaction zone. In each reaction zone the length of one or more adjacent heat exchange zone(s) may vary in their dimensions. For example, in one embodiment, the length of the one or more adjacent heat exchange zones may be less than about 50% of the length of each reaction zone. Alternatively, the one or more heat exchange zones may have lengths that are more than about 50% of the length of each reaction zone up to about 100% of the length of each reaction zone.

The catalyst may be in the form of a catalyst bed that may be graded in composition or graded with a thermally conductive inert material. The thermally conductive inert material may be interspersed with the active catalyst. Examples of thermally conductive inert materials that may be used include diamond powder, silicon carbide, aluminum, alumina, copper, graphite, and the like. The bed fraction may range from 100% by weight active catalyst to less than 50% by weight active catalyst. In an alternate embodiment the thermally conductive inert material may be deployed at the center or within the catalyst particles. The active catalyst may be deposited on the outside, inside or intermittent within a composite structure that includes the thermally conductive inert. The resulting catalyst composite structure may have an effective thermal conductivity when placed in a process microchannel that is at least about 0.5 W/m/K, and in one embodiment at least about 1 W/m/K, and in one embodiment at least about 2 W/m/K.

In one embodiment, the catalyst may be in the form of a catalyst bed that may be graded only locally within the reactor. For example, a process microchannel may contain a catalyst bed with a first reaction zone and a second reaction zone. The top or bottom (or front or back) of the catalyst bed may be graded in composition whereby a more or less active catalyst is employed in all or part of the first or second reaction zone. The composition that is reduced in one reaction zone may generate less heat per unit volume and thus reduce the hot spot and potential for the production of undesirable by-products. The catalyst may be graded with an inert material in the first and/or second reaction zone, in full or in part. The first reaction zone may contain a first composition of catalyst or inert material, while the second reaction zone may contain a second composition of catalyst or inert material.

In one embodiment, different particle sizes may be used in different axial length regions of the process microchannels to provide for graded catalyst beds. For example, very small particles may be used in a first reaction zone while larger particles may be used in a second reaction zone. The average particle diameters may be less than half the height or gap of the process microchannels. The very small particles may be less than one-fourth of the process microchannel height or gap. Larger particles may cause lower pressure drops per unit length of the process microchannels and may also reduce the catalyst effectiveness. The effective thermal conductivity of the catalyst bed may be lower for larger size particles. Smaller particles may be used in regions where improved heat transfer is sought throughout the catalyst bed or alternatively larger particles may be used to reduce the local rate of heat generation.

In one embodiment, relatively short contact times, high selectivity to the desired product and relatively low rates of deactivation of the catalyst may be achieved by limiting the diffusion path required for the catalyst. This may be achieved when the catalyst is in the form of a thin layer on an engineered support such as a metallic foam or on the wall of the process microchannel. This allows for increased space velocities. In one embodiment, the thin layer of catalyst may be produced using chemical vapor deposition or by a chemical reaction in a solution, for example, electroless plating. This thin layer may have a thickness in the range up to about 5 microns, and in one embodiment from about 0.1 to about 5 microns, and in one embodiment from about 0.5 to about 3 microns, and in one embodiment from about 1 to about 3 microns, and in one embodiment about 2.5 microns. These thin layers may reduce the time the reactants are within the active catalyst structure by reducing the diffusional path. This decreases the time the reactants spend in the active portion of the catalyst. The result may be increased selectivity to the product and reduced unwanted by-products. An advantage of this mode of catalyst deployment is that, unlike conventional catalysts in which the active portion of the catalyst may be bound up in an inert low thermal conductivity binder, the active catalyst film may be in intimate contact with either the engineered structure or the wall of the process microchannel. This may leverage high heat transfer rates attainable in the microchannel reactor and allow for close control of temperature. This may result in the ability to operate at increased temperature (faster kinetics) without promoting the formation of undesired by-products, thus producing higher productivity and yield and prolonging catalyst life.

The microchannel reactor configuration may be tailored to match the reaction kinetics. For example, near the entrance or top of a first reaction zone of the reactor, the microchannel height or gap may be smaller than in a second reaction zone near the exit or bottom of the reactor. Alternatively, the zones may be much smaller than half the reactor length. For example, a first process microchannel height or gap may be used for the first 25%, 50%, 75%, or 90% of the length of the process microchannel, while a larger second height or gap may be used in a second reaction zone downstream from the first reaction zone. Alternatively, different configurations may be used. For example, a larger process microchannel height or gap may be used near the entrance of the process microchannels and a smaller process microchannel height or gap may be used near the reactor exit. In one to embodiment, other gradations in the process microchannel height or gap may be used. For example, a first height or gap may be used near the entrance of the microchannel to provide a first reaction zone, a second height or gap downstream from the first reaction zone may be used to provide a second reaction zone, and a third height or gap may be used to provide a third reaction zone near the exit of the is microchannel. The first and third heights or gaps may be the same or different. The first and third heights or gaps may be larger or smaller than the second height or gap. The third height or gap may be smaller or larger than the second height or gap. The second height or gap may be larger or smaller than the third height or gap.

The openings or apertures 254 may be of sufficient size to permit the flow of the second reactant through the apertured sections. The openings 254 may be referred to as pores. The apertured section 258 may have thicknesses in the range from about 0.01 to about 50 mm, and in one embodiment about 0.05 to about 10 mm, and in one embodiment about 0.1 to about 2 mm. The openings 254 may have average diameters in the range up to about 1000 microns, and in one embodiment up to about 250 microns, and in one embodiment up to about 50 microns, and in one embodiment in the range from about 0.001 to about 50 microns, and in one embodiment from about 0.05 to about 50 microns, and in one embodiment from about 0.1 to about 50 microns. In one embodiment, the openings 254 may have average diameters in the range from about 0.5 to about 10 nanometers (nm), and in one embodiment about 1 to about 10 nm, and in one embodiment about 5 to about 10 nm. The number of openings 254 in the apertured section 258 may be in the range from about 1 to about $5 \times 10^8$ openings per square centimeter, and in one embodiment about 1 to about $1 \times 10^6$ openings per square centimeter. The openings 254 may or may not be isolated from each other. A portion or all of the openings 254 may be in fluid communication with other openings 254 within the apertured section 258; that is, a fluid may flow from one opening to another opening. The ratio of the thickness of the apertured section 258 to the length of the apertured section along the flow path of the fluids flowing through the process microchannels 210 may be in the range from about 0.001 to about 1, and in one embodiment about 0.01 to about 1, and in one embodiment about 0.03 to about 1, and in one embodiment about 0.05 to about 1, and in one embodiment about 0.08 to about 1, and in one embodiment about 0.1 to about 1.

The apertured section 258 may be constructed of any material that provides sufficient strength and dimensional stability to permit the operation of the inventive process. These materials include: steel (e.g., stainless steel, carbon steel, and the like); monel; inconel; aluminum; titanium; nickel; copper; chromium; brass; alloys of any of the foregoing metals; polymers (e.g., thermoset resins); ceramics; glass; composites comprising one or more polymers (e.g., thermoset resins) and fiberglass; quartz; silicon; microporous carbon, including carbon nanotubes or carbon molecular sieves; zeolites; or a combination of two or more thereof. The openings 254 may be formed using known techniques such as laser drilling, microelectro machining system (MEMS), lithography electrodeposition and molding (LIGA), electrical sparkling, or electrochemical or photochemical etching. The openings 254 may be formed using techniques used for making structured plastics, such as extrusion, or membranes, such as aligned carbon nanotube (CNT) membranes. The openings 254 may be formed using techniques such as sintering or compressing metallic powder or particles to form tortuous interconnected capillary channels and the techniques of membrane fabrication. The openings 254 may be reduced in size from the size provided by any of these methods by the application of coatings over the apertures internal side walls to partially fill the apertures. The selective coatings may also form a thin layer exterior to the porous body that provides the smallest pore size adjacent to the continuous flow path. The smallest average pore opening may be in the range from about one nanometer to about several hundred microns depending upon the desired droplet size for the emulsion. The aperatures may be reduced in size by heat treating as well as by methods that form an oxide scale or coating on the internal side walls of the apertures. These techniques may be used to partially occlude the aperatures to reduce the size of the openings for flow.

The apertured section 258 may be made from a metallic or nonmetallic porous material having interconnected channels or pores of an average pore size in the range from about 0.01 to about 200 microns. These pores may function as the openings 254. The porous material may be made from powder or particulates so that the average inter-pore distance is similar to the average pore size. When very small pore sizes are used, the inter-pore distance may also be very small. The porous material may be tailored by oxidization at a high temperature in the range from about 300° C. to about 1000° C. for a duration of about 1 hour to about 20 days, or by coating a thin layer of another material such as alumina by sol coating or nickel using chemical vapor deposition over the surface and the inside of pores to block the smaller pores, decrease pore size of larger pores, and in turn increase the inter-pore distance.

The catalyst used to form the ethylene oxide may comprise any olefin epoxidation catalyst useful for converting ethylene and oxygen or a source of oxygen to ethylene oxide. The catalyst may comprise a metal, metal oxide or mixed metal oxide. The metal may be Ag, Mo, Re, W, V, Nb, Sb, Sn, Pt, Pd, Cs, Zr, Cr, Mg, Mn, Ni, Co, Ce, or a mixture of two or more thereof. The catalyst may comprise Ag, or an oxide thereof. The catalyst may comprise sulfur, or an oxide thereof. These catalysts may also comprise one or more alkali metals or alkaline earth metals or other transition metals, rare earth metals, or lanthanides. The alkali metal may comprise lithium, cesium, or a mixture thereof. Additionally elements such as P and Bi may be present. The catalyst may be supported, and if so, useful support materials include metal oxides (e.g., alumina, titania, zirconia), silica, mesoporous materials, zeolites, refractory materials, or combinations of two or more thereof. The catalyst may be any of the catalysts disclosed in the following patents for use in converting ethylene to ethylene oxide: U.S. Pat. No. 4,908,343; U.S. Pat. No. 5,597,773; U.S. Pat. No. 5,703,253; U.S. Pat. No. 5,705,661; U.S. Pat. No. 6,762,311 B2; and EP 0266015 B1; these patents are incorporated herein by reference.

The olefin epoxidation catalyst may comprise silver and a promoting amount of lithium. The olefin epoxidation catalyst may comprise silver and a promoting amount of cesium. The catalyst may comprise silver and a promoting amount of rhenium. Oxides of one or more of the foregoing may be used. These catalysts may further comprise a support. The support may comprise alumina, for example, alpha-alumina.

The olefin epoxidation catalyst may comprise silver in an amount of up to 50% by weight, and in one embodiment from about 10% to about 50% by weight, and in one embodiment from about 10% to about 30% by weight, and in one embodiment from about 10% to about 25% by weight, and in one embodiment from about 15% to about 25% by weight.

The catalyst may comprise a silver based catalyst such as the silver based catalyst disclosed in EP 0 496 470 B1, which is incorporated herein by reference. This catalyst may comprise silver, one or more alkali metal promoters, one or more rhenium promoters, and optionally one or more rhenium co-promoters selected from sulfur, molybdenum, tungsten, chromium, or a mixture of two or more thereof. The catalyst may be supported on a support. The support may comprise at least about 85% by weight, and in one embodiment at least about 90% by weight of alpha alumina, from about 0.01 to about 6% by weight (measured as the oxide) of an alkaline earth metal in the form of an oxide, from about 0.01 to about 5% by weight (measured as the dioxide) of silicon in the form of an oxide, and from zero to about 10% by weight, and in one embodiment from about 0.1 to about 10% by weight (measured as the dioxide) of zirconium in the form of an oxide. The alkaline earth metal may comprise calcium and/or magnesium.

The catalyst may comprise a silver based catalyst such as the silver based catalyst disclosed in EP 1 292 587 B1, which is incorporated herein by reference. This catalyst may contain a catalytically effective amount of silver, a promoting amount of rhenium or compound thereof, a promoting amount of at least one further metal or compound thereof and optionally a co-promoting amount of a rhenium co-promoter which can be selected from one or more of sulfur, phosphorus, boron, and compounds thereof, on a refractory support. The at least one further metal may comprise one or more alkali metals, alkaline earth metals, molybdenum, tungsten, chromium, titanium, hafnium, zirconium, vanadium, thallium, thorium, tantalum, niobium, gallium and germanium and mixtures thereof. The at least one further metal may comprise lithium, potassium, rubidium, cesium, calcium and/or barium. The at least one further metal may comprise lithium, potassium and/ or cesium. The components of these catalysts may have a concentration, when calculated as the element in grams (g), milligrams (mg) or millimoles (mmol) per kilogram (kg) of the total catalyst, of silver at a concentration in the range from about 10 to about 300 g/kg, rhenium at a concentration in the range from about 0.01 to about 15 mmol/kg, one or more further metals at a concentration in the range from about 10 to about 3000 mg/kg, and one or more optional rhenium co-promoters at a concentration in the range from about 0.1 to about 10 mmol/kg.

Figures 17, 18, 19:
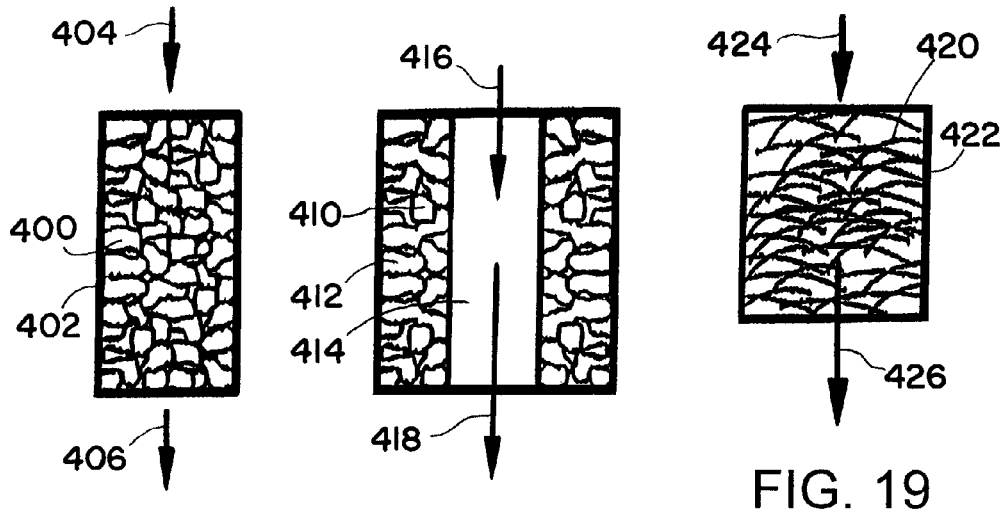

The catalyst used in a microchannel reactor may have any size and geometric configuration that fits within the process microchannels. The catalyst may be in the form of particulate solids (e.g., pellets, powder, fibers, and the like) having a median particle diameter of about 1 to about 1000 μm (microns), and in one embodiment from about 10 to about 500 μm, and in one embodiment from about 25 to about 300 μm, and in one embodiment from about 80 to about 300 μm (i.e. approximately US mesh 50 to 200 range). In one embodiment, the catalyst is in the form of a bed of particulate solids, for example, a fixed bed of particulate solids. This is shown in FIG. 17 wherein a bed of particulate solids 400 is packed in process microchannel 402. Reactants flow into the process microchannel as indicated by arrow 404 and product flows out of the process microchannel as indicated by arrow 406.

The catalyst may be supported on a porous support structure such as a foam, felt, wad or a combination thereof. The term "foam" is used herein to refer to a structure with continuous walls defining pores throughout the structure. The term "felt" is used herein to refer to a structure of fibers with interstitial spaces there between. The term "wad" is used herein to refer to a structure of tangled strands, like steel wool. The catalyst may be supported on a honeycomb structure.

The catalyst may be supported on a flow-by support structure such as a felt with an adjacent gap, a foam with an adjacent gap, a fin structure with gaps, a washcoat on any inserted substrate, or a gauze that is parallel to the flow direction with a corresponding gap for flow. An example of a flow-by structure is illustrated in FIG. 18. In FIG. 18, the catalyst 410 is contained within process microchannel 412. An open passage way 414 permits the flow of fluid through the process microchannel 412 in contact with the catalyst 410 as indicated by arrows 416 and 418.

The catalyst may be supported on a flow-through support structure such as a foam, wad, pellet, powder, or gauze. An example of a flow-through structure is illustrated in FIG. 19. In FIG. 19, the flow-through catalyst 420 is contained within process microchannel 422 and the fluid flows through the catalyst 420 as indicated by arrows 424 and 426.

The support structure for a flow-through catalyst may be formed from a material comprising silica gel, foamed copper, sintered stainless steel fiber, steel wool, alumina, poly(methyl methacrylate), polysulfonate, poly(tetrafluoroethylene), iron, nickel sponge, nylon, polyvinylidene difluoride, polypropylene, polyethylene, polyethylene ethylketone, polyvinyl alcohol, polyvinyl acetate, polyacrylate, polymethylmethacrylate, polystyrene, polyphenylene sulfide, polysulfone, polybutylene, or a combination of two or more thereof. In one embodiment, the support structure may be made of a heat conducting material, such as a metal, to enhance the transfer of heat away from the catalyst.

The catalyst may be directly washcoated on the interior walls of the process microchannels, grown on the walls from solution, or coated in situ on a fin structure or other support structure. The catalyst may be in the form of one or more pieces of porous contiguous material. In one embodiment, the catalyst may be comprised of a contiguous material and has a contiguous porosity such that molecules can diffuse through the catalyst. In this embodiment, the fluids flow through the catalyst rather than around it. In one embodiment, the cross-sectional area of the catalyst occupies about 1 to about 99%, and in one embodiment about 10 to about 95% of the cross-sectional area of the process microchannels. The catalyst may have a surface area, as measured by BET, of greater than about 0.5 m$^2$/g, and in one embodiment greater than about 2 m$^2$/g.

The catalyst may comprise a porous support, an interfacial layer on the porous support, and a catalyst material on the interfacial layer. The interfacial layer may be solution deposited on the support or it may be deposited by chemical vapor deposition or physical vapor deposition. In one embodiment the catalyst has a porous support, a buffer layer, an interfacial layer, and a catalyst material. Any of the foregoing layers may be continuous or discontinuous as in the form of spots or dots, or in the form of a layer with gaps or holes.

The porous support may have a porosity of at least about 5% as measured by mercury porosimetry and an average pore size (sum of pore diameters divided by number of pores) of about 1 to about 1000 μm. The porous support may be a porous ceramic or a metal foam. Other porous supports that may be used include carbides, nitrides, and composite materials. The porous support may have a porosity of about 30% to about 99%, and in one embodiment about 60% to about 98%. The porous support may be in the form of a foam, felt, wad, or a combination thereof. The open cells of the metal foam may range from about 20 pores per inch (ppi) to about 3000 ppi, and in one embodiment about 20 to about 1000 ppi, and in one embodiment about 40 to about 120 ppi. The term "ppi" refers to the largest number of pores per inch (in isotropic materials the direction of the measurement is irrelevant; however, in anisotropic materials, the measurement is done in the direction that maximizes pore number).

The buffer layer, when present, may have a different composition and/or density than both the porous support and the interfacial layers, and in one embodiment has a coefficient of thermal expansion that is intermediate the thermal expansion coefficients of the porous support and the interfacial layer. The buffer layer may be a metal oxide or metal carbide. The buffer layer may be comprised of $Al_2O_3$, $TiO_2$, $SiO_2$, $ZrO_2$, or combination thereof. The $Al_2O_3$ may be α-$Al_2O_3$, γ-$Al_2O_3$ or a combination thereof. α-$Al_2O_3$ provides the advantage of excellent resistance to oxygen diffusion. The buffer layer may be formed of two or more compositionally different sublayers. For example, when the porous support is metal, for example a stainless steel foam, a buffer layer formed of two compositionally different sub-layers may be used. The first sublayer (in contact with the porous support) may be $TiO_2$. The second sublayer may be α-$Al_2O_3$ which is placed upon the $TiO_2$. In one embodiment, the α-$Al_2O_3$ sublayer is a dense layer that provides protection of the underlying metal surface. A less dense, high surface area interfacial layer such as alumina may then be deposited as support for a catalytically active layer.

The porous support may have a thermal coefficient of expansion different from that of the interfacial layer. In such a case a buffer layer may be needed to transition between the two coefficients of thermal expansion. The thermal expansion coefficient of the buffer layer can be tailored by controlling its composition to obtain an expansion coefficient that is compatible with the expansion coefficients of the porous support and interfacial layers. The buffer layer should be free of openings and pin holes to provide superior protection of the underlying support. The buffer layer may be nonporous. The buffer layer may have a thickness that is less than one half of the average pore size of the porous support. The buffer layer may have a thickness of about 0.05 to about 10 μm, and in one embodiment about 0.05 to about 5 μm.

In one embodiment of the invention, adequate adhesion and chemical stability may be obtained without a buffer layer. In this embodiment the buffer layer may be omitted.

The interfacial layer may comprise nitrides, carbides, sulfides, halides, metal oxides, carbon, or a combination thereof. The interfacial layer provides high surface area and/or provides a desirable catalyst-support interaction for supported catalysts. The interfacial layer may be comprised of any material that is conventionally used as a catalyst support. The interfacial layer may be comprised of a metal oxide. Examples of metal oxides that may be used include $Al_2O_3$, $SiO_2$, $ZrO_2$, $TiO_2$, tungsten oxide, magnesium oxide, vanadium oxide, chromium oxide, manganese oxide, iron oxide, nickel oxide, cobalt oxide, copper oxide, zinc oxide, molybdenum oxide, tin oxide, calcium oxide, aluminum oxide, lanthanum series oxide(s), zeolite(s) and combinations thereof. The interfacial layer may serve as a catalytically active layer without any further catalytically active material deposited thereon. Usually, however, the interfacial layer is used in combination with a catalytically active layer. The interfacial layer may also be formed of two or more compositionally different sublayers. The interfacial layer may have a thickness that is less than one half of the average pore size of the porous support. The interfacial layer thickness may range from about 0.5 to about 100 μm, and in one embodiment from about 1 to about 50 μm. The interfacial layer may be either crystalline or amorphous. The interfacial layer may have a BET surface area of at least about 1 m$^2$/g.

The catalyst may be deposited on the interfacial layer. Alternatively, the catalyst material may be simultaneously deposited with the interfacial layer. The catalyst layer may be intimately dispersed on the interfacial layer. That the catalyst layer is "dispersed on" or "deposited on" the interfacial layer includes the conventional understanding that microscopic catalyst particles are dispersed: on the support layer (i.e., interfacial layer) surface, in crevices in the support layer, and in open pores in the support layer.

The catalyst may be in the form of a bed of particulate solids positioned in a reaction zone wherein one or more interior walls of the reaction zone includes additional catalyst washcoated and/or grown thereon. The catalyst in the bed of particulate solids may be the same as the catalyst washcoated and/or grown on the interior walls of the reaction zone, or it may be different.

Figure 20:
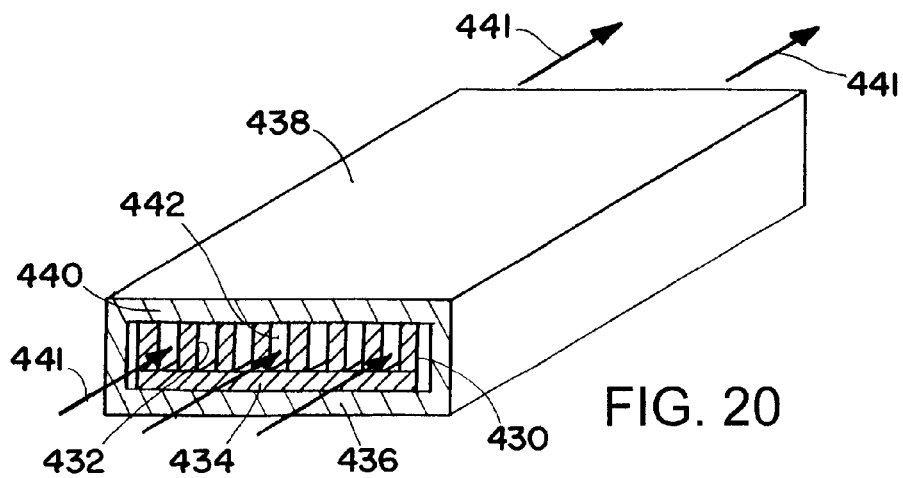
Figures 21, 22:
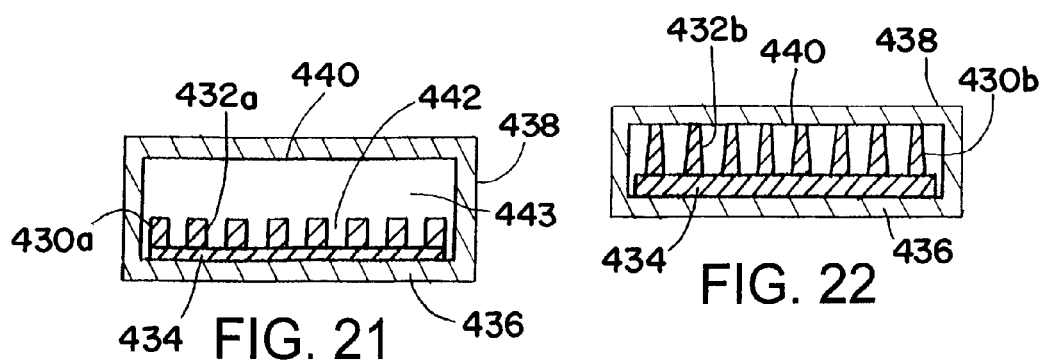

The catalyst may be supported on an assembly of one or more fins or other structures positioned within the process microchannels. Examples are illustrated in FIGS. 20-21. Referring to FIG. 20, fin assembly 430 includes fins 432 which are mounted on fin support 434 which overlies base wall 436 of process microchannel 438. The fins 432 project from the fin support 434 into the interior of the process microchannel 438. The fins 432 extend to and may contact the interior surface of upper wall 440 of process microchannel 438. Fin channels 442 between the fins 432 provide passage ways for fluid to flow through the process microchannel 438 parallel to its length. Each of the fins 432 has an exterior surface on each of its sides, this exterior surface provides a support base for the catalyst. With the inventive process, the reactant composition flows through the fin channels 442, contacts the catalyst supported on the exterior surface of the fins 432, and reacts to form the product. The fin assembly 430a illustrated in FIG. 21 is similar to the fin assembly 430 illustrated in FIG. 20 except that the fins 432a do not extend all the way to the interior surface of the upper wall 440 of the microchannel 438. The fin assembly 430*b* illustrated in FIG. 22 is similar to the fin assembly 430 illustrated in FIG. 20 except that the fins 432*b* in the fin assembly 430*b* have cross sectional shapes in the form of trapezoids. Each of the fins may have a height ranging from about 0.02 mm up to the height of the process microchannel 438, and in one embodiment from about 0.02 to about 10 mm, and in one embodiment from about 0.02 to about 5 mm, and in one embodiment from about 0.02 to about 2 mm. The width of each fin may range from about 0.02 to about 5 mm, and in one embodiment from about 0.02 to about 2 mm and in one embodiment about 0.02 to about 1 mm. The length of each fin may be of any length up to the length of the process microchannel 438, and in one embodiment up to about 10 m, and in one embodiment about 0.5 to about 10 m, and in one embodiment about 0.5 to about 6 m, and in one embodiment about 0.5 to about 3 m. The gap between each of the fins may be of any value and may range from about 0.02 to about 5 mm, and in one embodiment from about 0.02 to about 2 mm, and in one embodiment from about 0.02 to about 1 mm. The number of fins in the process microchannel 438 may range from about 1 to about 50 fins per centimeter of width of the process microchannel 438, and in one embodiment from about 1 to about 30 fins per centimeter, and in one embodiment from about 1 to about 10 fins per centimeter, and in one embodiment from about 1 to about 5 fins per centimeter, and in one embodiment from about 1 to about 3 fins per centimeter. Each of the fins may have a cross-section in the form of a rectangle or square as illustrated in FIG. 20 or 21, or a trapezoid as illustrated in FIG. 22. When viewed along its length, each fin may be straight, tapered or have a serpentine configuration. The fin assembly may be made of any material that provides sufficient strength, dimensional stability and heat transfer characteristics to permit operation for which the process microchannel is intended. These materials include: steel (e.g., stainless steel, carbon steel, and the like); aluminum; titanium; nickel; platinum; rhodium; copper; chromium; alloys of any of the foregoing metals; monel; inconel; brass; polymers (e.g., thermoset resins); ceramics; glass; composites comprising one or more polymers (e.g., thermoset resins) and fiberglass; quartz; silicon; or a combination of two or more thereof. The fin assembly may be made of an $Al_2O_3$ forming material such as an alloy comprising Fe, Cr, Al and Y, or a $Cr_2O_3$ forming material such as an alloy of Ni, Cr and Fe.

The catalyst may be supported by a microgrooved support strip. Examples of these support strips are illustrated in FIGS. 23 and 24. Referring to FIG. 23, process microchannel 450 includes support strip 452 mounted on interior wall 454 of the process microchannel 450. Bulk flow region 456 is defined by the space within the process microchannel 450 between the support strip 452 and the top channel wall 457. Process fluid flows through the process microchannel 450 as indicated by arrows 458 and 460. In flowing through the process microchannel 450, the process fluid flows through the bulk flow region 456 in contact with the catalyst support strip 452. The catalyst may be in the form of microsized particulates positioned in the microgrooves 462. The support strip 452 is a flow-by support strip. However, some of the process fluid may flow in the microgrooves 462 in contact with the catalyst. The flow of the process fluid through the microgrooves 462 may be in the general direction from the front edge 463 and the first side edge 464 toward the second side edge 466 and the back edge 468. The process microchannel illustrated in FIG. 24 is similar to the process microchannel illustrated in FIG. 23 with the exception that the process microchannel 450 illustrated in FIG. 24 contains opposite interior walls 454 and 457 and a catalyst supporting support strip 452 mounted on each of the opposite interior walls. Additional details concerning the construction and use of the microgrooved support strip 452 can be found in US Patent Publication No. U.S. 2007-0225532A1, which is incorporated herein by reference.

Surface features can be used in combination with a supported catalyst to enhance contact between the reactants and the catalyst. This is shown in FIG. 25. Referring to FIG. 25, process microchannel 450 which has support strip 452 mounted on interior wall 454 and surface features 470 formed in the opposite interior wall 457. Process fluid flows through the process microchannel 450 as indicated by arrows 472. The flow of the process fluid is modified as the process fluid flows through surface features 470. The surface features 470 illustrated in FIG. 25 are in the form of hemispherical depressions in the microchannel wall 457. The modification of the flow of the process fluids by the surface features 470 enhances contact between the process fluid and the catalyst supported by the support strip 452.

The catalyst may be positioned in a process microchannel upstream and/or downstream of a bed of inert particulates. The bed of inert particulates upstream of the catalyst may be used to modify the temperature and/or flow characteristics of the reactants entering the catalyst. The bed of inert particulates downstream of the catalyst may be used to modify the temperature and/or flow characteristics of the product flowing out of the catalyst. For example, the catalyst may be in the form of a bed of particulate solids, and a bed of inert particulates may be positioned upstream of the catalytic bed and another bed of inert particulates may be positioned downstream of the catalytic bed. The inert particulates may comprise, for example, silicon carbide, steatite, alumina, doped alumina, or a mixture of two or more thereof. The inert particulates may have a median particulate diameter in the range from about 1 to about 1000 μm, and in one embodiment from about 10 to about 500 μm, and in one embodiment from about 25 to about 300 μm, and in one embodiment from about 80 to about 300 μm (i.e. approx. US mesh 50 to 200 range). The catalyst bed and inert particulate beds may be positioned in a process microchannel. The length of the catalyst bed may be in the range from about 0.5 to about 200 cm, and in one embodiment in the range from about 1.5 to about 60 cm. The ratio of the length of the catalyst bed to the length of the inert bed upstream of the catalyst bed may be in the range from about 2 to about 100, and in one embodiment from about 4 to about 50. The ratio of the length of the catalyst bed to the length of the inert bed downstream of the catalyst bed may be in the range from about 2 to about 100, and in one embodiment from about 4 to about 50.

The catalyst may be regenerated. This may be done by flowing a regenerating fluid through the process microchannels in contact with the catalyst. The regenerating fluid may comprise hydrogen or a diluted hydrogen stream, oxygen or an oxygen containing stream, or a stream containing a halogen containing gas or a mixture of oxygen and a halogen containing gas. Halogen compounds may include metal halides and organic halides. The diluent may comprise nitrogen, argon, helium, methane, ethylene, carbon dioxide, steam, or a mixture of two or more thereof. The regenerating fluid may flow from the header through the process microchannels and to the footer, or in the opposite direction from the footer through the process microchannels to the header. The temperature of the regenerating fluid may be from about 50 to about 400° C., and in one embodiment about 200 to about 350° C. The pressure within the process microchannels during this regeneration step may range from about 1 to about 40 bars, and in one embodiment about 1 to about 20 bars, and in one embodiment about 1 to about 5 bars. The residence time for the regenerating fluid in the process microchannels may range from about 0.01 to about 1000 seconds, and in one embodiment about 0.1 second to about 100 seconds.

The process microchannels may be characterized by having a bulk flow path. The term "bulk flow path" refers to an open path (contiguous bulk flow region) within the process microchannels. A contiguous bulk flow region allows rapid fluid flow through the microchannels without large pressure drops. In one embodiment, the flow of fluid in the bulk flow region is laminar. Bulk flow regions within each process microchannel may have a cross-sectional area of about 0.05 to about 10,000 mm$^2$, and in one embodiment about 0.05 to about 5000 mm$^2$, and in one embodiment about 0.1 to about 2500 mm$^2$. The bulk flow regions may comprise from about 5% to about 95%, and in one embodiment about 30% to about 80% of the cross-section of the process microchannels.

The heat exchange fluid may be any fluid. These include air, steam, liquid water, steam, gaseous nitrogen, other gases including inert gases, carbon monoxide, molten salt, oils such as mineral oil, a gaseous hydrocarbon, a liquid hydrocarbon, heat exchange fluids such as Dowtherm A and Therminol which are available from Dow-Union Carbide, or a mixture of two or more thereof.

The heat exchange fluid may comprise a stream of one or more of the reactants and/or the product. This can provide process cooling for the process microchannels and/or preheat for the reactants and thereby increase the overall thermal efficiency of the process.

The heat exchange channels may comprise process channels wherein an endothermic process is conducted. These heat exchange process channels may be microchannels. Examples of endothermic processes that may be conducted in the heat exchange channels include steam reforming and dehydrogenation reactions. Steam reforming of an alcohol that occurs at a temperature in the range from about 200° C. to about 300° C. is an example of an endothermic process suited for an exothermic reaction such as an ethylene oxide synthesis reaction in the same temperature range. The incorporation of a simultaneous endothermic reaction to provide an improved heat sink may enable a typical heat flux of roughly an order of magnitude above the convective cooling heat flux.

The heat exchange fluid may undergo a partial or full phase change as it flows through the heat exchange channels. This phase change may provide additional heat removal from the process microchannels beyond that provided by convective cooling. For a liquid heat exchange fluid being vaporized, the additional heat being transferred from the process microchannels would result from the latent heat of vaporization required by the heat exchange fluid. An example of such a phase change would be a heat exchange fluid such as oil or water that undergoes partial boiling. In one embodiment, up to about 50% by weight of the heat exchange fluid may be vaporized.

The heat flux for heat exchange in the microchannel reactor may range from about 1 to about 500 watts per square centimeter of surface area of the heat transfer walls (W/cm$^2$) in the microchannel reactor, and in one embodiment from about 1 to about 350 W/cm$^2$, and in one embodiment from about 1 to about 250 W/cm$^2$, and in one embodiment from about 1 to about 100 W/cm$^2$, and in one embodiment from about 1 to about 50 W/cm$^2$, and in one embodiment from about 1 to about 25 W/cm$^2$, and in one embodiment from about 1 to about 10 W/cm$^2$.

The cooling of the process microchannels during the inventive process, in one embodiment, is advantageous for controlling selectivity towards the main or desired product due to the fact that such added cooling reduces or eliminates the formation of undesired by-products from undesired parallel reactions with higher activation energies. As a result of this cooling, in one embodiment, the temperature of the reactants at the entrance to the process microchannels may be within about 20° C., and in one embodiment within about 10° C., and in one embodiment within about 5° C., and in one embodiment within about 3° C., and in one embodiment within about 2° C., and in one embodiment within about 1° C., of the temperature of the product (or mixture of product and unreacted reactants) at the outlet of the process microchannels. In one embodiment, the process microchannels may be operated with an isothermal or substantially isothermal temperature profile.

The contact time of the process fluids with the catalyst within the process microchannels may range from about 50 to about 900 milliseconds (ms), and in one embodiment from about 100 to about 900 ms, and in one embodiment from about 100 to about 500 ms, and in one embodiment from about 100 to about 300 ms, and in one embodiment from about 150 to about 300 ms.

The space velocity (or gas hourly space velocity) for the flow of process fluid through the process microchannels may be in the range from about 1000 to about 50,000 liter of feed per liter of catalyst per hour (hr$^{-1}$). The space velocity may range from about 2500 to about 35,000 hr$^{-1}$, and in one embodiment from about 5000 to about 20,000 hr$^{-1}$.

The selectivity to ethylene oxide may be in the range from about 75 to about 95%, and in one embodiment from about 80 to about 95%, and in one embodiment in the range from about 85 to about 95%, and in one embodiment in the range from about 88 to about 92%.

The production rate or catalyst work rate for the inventive process may be at least about 250 kilograms of ethylene oxide per cubic meter of catalyst per hour (Kg/m$^3_{cat}$/hr), and in one embodiment at least about 300 kilograms of ethylene oxide per cubic meter of catalyst per hour, and in one embodiment at least about 350 kilograms of ethylene oxide per cubic meter of catalyst per hour, and in one embodiment at least about 400 kilograms of ethylene oxide per cubic meter of catalyst per hour. The production rate of ethylene oxide may be in the range from about 250 to about 5000 kilograms per cubic meter of catalyst per hour, and in one embodiment in the range from about 300 to about 5000 kilograms per cubic meter of catalyst per hour, and in one embodiment in the range from about 350 to about 5000 kilograms per cubic meter of catalyst per hour, and in one embodiment in the range from about 400 to about 5000 kilograms per cubic meter of catalyst per hour, and in one embodiment in the range from about 500 to about 5000 kilograms per cubic meter of catalyst per hour.

The catalyst productivity for the inventive process may be at least about 0.5 kiloton of ethylene oxide produced per cubic meter of catalyst (kt$_{EO}$/m$^3_{cat}$), and in one embodiment at least about 1 kiloton of ethylene oxide per cubic meter of catalyst, and in one embodiment at least about 2 kilotons of ethylene oxide per cubic meter of catalyst, and in one embodiment at least about 3 kilotons of ethylene oxide per cubic is meter of catalyst, and in one embodiment at least about 4 kilotons of ethylene oxide per cubic meter of catalyst. The catalyst productivity may be from about 0.5 to 10 kilotons of ethylene oxide per cubic meter of catalyst, and in one embodiment from about 1 to about 10 kilotons of ethylene oxide per cubic meter of catalyst, and in one embodiment from about 1 to about 8 kilotons of ethylene oxide per cubic meter of catalyst, and in one embodiment from about 1 to about 6 kilotons of ethylene oxide per cubic meter of catalyst, and in one embodiment from about 1 to about 4 kilotons of ethylene oxide per cubic meter of catalyst, and in one embodiment from about 2 to about 4 kilotons of ethylene oxide per cubic meter of catalyst.

The production rate or catalyst work rate for the inventive process may be at least about 250 Kg/m$^3_{cat}$/hr and the selectivity to ethylene oxide may be at least about 88%, and in one embodiment from about 88 to about 92%. The catalyst productivity may be at least about 1 kt$_{EO}$/m$^3_{cat}$.

The production rate or catalyst work rate may be at least about 250 Kg/m$^3_{cat}$/hr, the selectivity to ethylene oxide may be at least about 87%, and the catalyst productivity may be at least about 2 kt$_{EO}$/m$^3_{cat}$.

The production rate or catalyst work rate may be at least about 250 Kg/m$^3_{cat}$/hr, the selectivity to ethylene oxide may be at least about 85%, and the catalyst productivity may be at least about 3 kt$_{EO}$/m$^3_{cat}$.

The production rate or catalyst work rate may be at least about 250 Kg/m$^3_{cat}$/hr, the selectivity to ethylene oxide may be at least about 83%, and the catalyst productivity may be at least about 4 kt$_{EO}$/m$^3_{cat}$.

The present invention relates to a process, comprising: reacting ethylene and oxygen or a source of oxygen in the presence of a catalyst in a process microchannel to form a product comprising ethylene oxide at a rate of at least about 250 Kg/m$^3_{cat}$/hr, the selectivity to ethylene oxide being at least about 84%, the catalyst being in a reaction zone in the process microchannel; and maintaining an average temperature in the reaction zone below about 220° C.

The present invention relates to a process, comprising: reacting ethylene and oxygen or a source of oxygen in the presence of a catalyst in a process microchannel to form a product comprising ethylene oxide at a rate of at least about 350 Kg/m$^3_{cat}$/hr, the selectivity to ethylene oxide being at least about 80%, the catalyst being in a reaction zone in the process microchannel; and maintaining an average temperature in the reaction zone below about 220° C.

The present invention relates to a process, comprising: reacting ethylene and oxygen or a source of oxygen in the presence of a catalyst in a process microchannel to form a product comprising ethylene oxide at a rate of at least about 350 Kg/m$^3_{cat}$/hr, the selectivity to ethylene oxide being at least about 84%, the catalyst being in a reaction zone in the process microchannel; and maintaining an average temperature in the reaction zone below about 220° C.

The present invention relates to a process, comprising: reacting ethylene and oxygen or a source of oxygen in the presence of a catalyst in a process microchannel to form a product comprising ethylene oxide at a rate of at least about 250 Kg/m$^3_{cat}$/hr, the selectivity to ethylene oxide being at least about 84%, the catalyst being in a reaction zone in the process microchannel; and maintaining an average temperature in the reaction zone above about 265° C.

The present invention relates to a process, comprising: reacting ethylene and oxygen or a source of oxygen in the presence of a catalyst in a process microchannel to form a product comprising ethylene oxide at a rate of at least about 350 Kg/m$^3_{cat}$/hr, the selectivity to ethylene oxide being at least about 80%, the catalyst being in a reaction zone in the process microchannel; and maintaining an average temperature in the reaction zone above about 265° C.

The present invention relates to a process, comprising: reacting ethylene and oxygen or a source of oxygen in the presence of a catalyst in a process microchannel to form a product comprising ethylene oxide at a rate of at least about 350 Kg/m$^3_{cat}$/hr, the selectivity to ethylene oxide being at least about 84%, the catalyst being in a reaction zone in the process microchannel; and maintaining an average temperature in the reaction zone above about 265° C.

A production run may be started after the catalyst, process microchannel and one or more of the reactants are allowed to undergo a conditioning period of up to about 500 hours, and in one embodiment up to about 400 hours, and in one embodiment up to about 300 hours, and in one embodiment up to about 200 hours. During this conditioning period the catalyst, process microchannel and one or more reactants may be permitted to achieve an equilibrium temperature. The process may be commenced during the conditioning period to allow the production rate to build to a desired level prior to the start of a production run (SOR). The start of a production run may be commenced when an average production rate of at least about 250 kilograms of ethylene oxide per cubic meter of catalyst per hour (Kg/m$^3_{cat}$/hr) is established. The start-of-run temperature (T$_{SOR}$) for a production run may be in the range from about 150° to about 265° C., and in one embodiment in the range from about 150° C. to about 250° C., and in one embodiment in the range from about 150° C. to about 240° C., and in one embodiment in the range from about 150° C. to about 230° C., and in one embodiment in the range from about 150° C. to about 220° C., and in one embodiment in the range from about 150° C. to about 210° C., and in one embodiment in the range from about 150° C. to about 200° C., and in one embodiment in the range from about 150° C. to about 190° C. After the start of the production run, the temperature in the reaction zone may be relatively constant, but allowed to increase gradually to compensate for gradual deactivation of the catalyst. In one embodiment, the average temperature in the reaction zone during a production run may not decrease by more than about 20° C., and in one embodiment not more than about 10° C., and in one embodiment not more than about 5° C., and in one embodiment not more than about 2° C.

The start-up of a production run may involve initially loading the catalyst in a microchannel reactor and drying the catalyst by flowing an inert gas such as N$_2$ through the reactor while maintaining the temperature within the reactor in the range of about 200° C. to about 240° C., and in one embodiment from about 225° C. to about 235° C. The flow of the inert gas may be continued for a period of time in the range from about 0.5 to about 48 hours, and in one embodiment for about 1 to about 24 hours, while the pressure in the reactor is in the range from about 0.8 to about 5 atmospheres (absolute pressure), and in one embodiment in the range from about 1 to about 2 atmospheres. The space velocity may be in the range from about 100 to about 40,000 v/v/hr, and in one embodiment in the range from about 1,000 to about 30,000 v/v/hr. The pressure within the reactor may then be increased to a pressure in the range from about 5 to about 30 atmospheres, and in one embodiment in the range from about 10 to about 25 atmospheres. The flow of the inert gas may then be replaced by the flow of a diluted reactant stream containing ethylene, an organic halide (e.g., ethyl chloride), optionally CO$_2$, and an inert gas such as N$_2$, wherein the concentration of the inert gas is relatively high, for example, in the range from about 50% to about 90% by volume, and in one embodiment in the range from about 60% to about 80% by volume. The concentration of CO$_2$ may be up to about 10% by volume, and in one embodiment in the range from about 1% to about 5% by volume. The flow of the diluted reactant stream may be continued for a period of time in the range from about 0.5 to about 48 hours, and in one embodiment from about 1 to about 24 hours. The space velocity may be in the range from about 100 to about 40,000 v/v/hr, and in one embodiment in the range from about 1,000 to about 30,000 v/v/hr. The flow of oxygen or the source of oxygen may then be commenced, initially at a reduced concentration, wherein the concentration of oxygen or source of oxygen in the diluted reactant stream is increased from zero to a concentration in the range from about 1 to about 15 percent by volume, and in one embodiment to a concentration in the range from about 2 to about 6 percent by volume, step-wise over a period for time in the range from about 0.5 to about 48 hours, and in one embodiment in the range from about 1 to about 24 hours. The inert gas in the diluted reactant stream may then be replaced by methane step-wise over a period of time in the range from about 0.5 to about 24 hours, and in one embodiment in the range from about 1 to about 8 hours. The concentration of oxygen or the source of oxygen may then be increased step-wise to the desired concentration in the range from about 2 to about 50 percent by volume, and in one embodiment in the range from about 7 to about 25 percent by volume, and in one embodiment in the range from about 7 to about 15 percent by volume over a period of time in the range from about 0.5 to about 24 hours, and in one embodiment in the range from about 1 to about 8 hours. The concentration of organic halide in the feed stream may then be increased step-wise to the desired concentration in the range from about 0.1 to about 5 parts per million by volume, and in one embodiment from about 1 to about 4 parts per million by volume, over a period of time in the range from about 1 to about 48 hours, and in one embodiment from about 2 to about 8 hours. The temperature within the reactor may then be increased step-wise to a temperature in the range from about 160 to about 270° C., and in one embodiment from about 180 to about 250° C., over a period of time in the range from about 0.5 to about 48 hours, and in one embodiment in the range from about 1 to about 24 hours. The space velocity may be in the range from about 1,000 to about 40,000 v/v/hr, and in one embodiment in the range from about 2,000 to about 30,000 v/v/hr. The reactor may then be held under these conditions for a period of time in the range from about 0.5 to about 72 hours, and in one embodiment from about 1 to about 24 hours. The concentration level of the methane may then be reduced step-wise to a level in the range from about 5 to about 80 percent by volume, and in one embodiment in the range from about 10 to about 75 percent by volume, over a period of time in the range from about 1 to about 48 hours, and in one embodiment from about 2 to about 24 hours. The space velocity may be in the range from about 1,000 to about 40,000 v/v/hr, and in one embodiment in the range from about 1,000 to about 30,000 v/v/hr. The reactor may then be held under these conditions for a period of time in the range from about 0.5 to about 48 hours, and in one embodiment from about 1 to about 24 hours. The concentration level of $CO_2$ may then be reduced step-wise to a level in the range from about 1 to about 5 percent by volume, and in one embodiment in the range from about 0.1 to about 2 percent by volume, over a period of time in the range from about 0.5 to about 96 hours, and in one embodiment in the range from about 1 to about 48 hours. The reaction conditions may then be adjusted as desired. This start-up procedure may be referred to as a gentle start-up. This start-up procedure, which involves a gradual exposure of the catalyst to the reactants, may be advantageous due to the fact that it prevents the formation of local hot-spots that may cause significant increases in the deactivation rate. Also, the relatively long holds at high temperatures are believed to be advantageous for activating all of the catalyst sites.

The end of a production run (EOR) may occur when a maximum desired temperature ($T_{EOR}$) in the reaction zone is achieved. The end-of-run temperature may be about 265° C., and in one embodiment in the range from about 265° C. to about 270° C., and in one embodiment in the range from about 265° C. to about 280° C.

Alternatively, the end of a production run may occur when the selectivity to ethylene oxide and the rate of production of ethylene oxide decreases below a desired level. The end of a production run may occur when the selectivity to ethylene oxide decreases below about 84%, and in one embodiment below about 82%, and in one embodiment below about 80%; and/or the rate of production of ethylene oxide decreases to a level below about 245 kilograms of ethylene oxide per cubic meter of catalyst, and in one embodiment below about 240 kilograms of ethylene oxide per cubic meter of catalyst, and in one embodiment below about 235 kilograms of ethylene oxide per cubic meter of catalyst, and in one embodiment below about 230 kilograms of ethylene oxide per cubic meter of catalyst, and in one embodiment below about 225 kilograms of ethylene oxide per cubic meter of catalyst, and in one embodiment below about 220 kilograms of ethylene oxide per cubic meter of catalyst.

The average temperature of the process fluids in the process microchannels may be in the range from about 150° C. to about 265° C., and in one embodiment from about 180° C. to about 265° C., and in one embodiment from about 200° C. to about 265° C., and in one embodiment from about 220° C. to about 265° C.

The pressure in the process microchannels may be in the range from about 5 to about 30 bars, and in one embodiment from about 10 to about 20 bars.

The pressure drop for the process fluids as they flow in the process microchannels may range up to about 2 bars per foot of length of the process microchannel (bars/ft), and in one embodiment up to about 1.5 bars/ft, and in one embodiment up to 1 bars/ft, and in one embodiment up to about 0.5 bars/ft.

The flow of the process fluids in the process microchannels may be laminar or in transition, and in one embodiment it is laminar. The Reynolds Number for the flow of process fluids in the process microchannels may be up to about 4000, and in one embodiment up to about 2300, and in one embodiment in the range of about 10 to about 2000, and in one embodiment about 100 to about 1500.

The superficial velocity for the process fluids flowing in the process microchannels may be at least about 0.01 meters per second (m/s), and in one embodiment in the range from about 0.01 to about 5 m/s, and in one embodiment in the range from about 0.01 to about 2 m/s, and in one embodiment in the range from about 0.01 to about 1 m/s, and in one embodiment in the range from about 0.05 to about 0.5 m/s.

The heat exchange fluid in the heat exchange channels may have a temperature in the range from about 100° C. to about 270° C., and in one embodiment from about 120° C. to about 250° C., and in one embodiment from about 140° C. to about 230° C. The difference in temperature between the heat exchange fluid and the process fluids in the process microchannel may be up to about 50° C., and in one embodiment up to about 30° C., and in one embodiment up to about 10° C. The residence time of the heat exchange fluid in the heat exchange channels may range from about 1 to about 1000 ms, and in one embodiment about 1 to about 500 ms, and in one embodiment from 1 to about 100 ms. The pressure drop for the heat exchange fluid as it flows in the heat exchange channels may be up to about 3 bar/ft, and in one embodiment up to about 1 bar/ft. The flow of the heat exchange fluid in the heat exchange channels may be laminar or in transition, and in one embodiment it is laminar. The Reynolds Number for the flow of heat exchange fluid in the heat exchange channels may be up to about 4000, and in one embodiment up to about 2300, and in one embodiment in the range of about 10 to about 2000, and in one embodiment about 10 to about 1500.

The control of heat exchange during the ethylene oxide-forming reaction process may be advantageous for controlling selectivity towards the desired product due to the fact that added cooling may reduce or eliminate the formation of undesired by-products from undesired parallel reactions with higher activation energies.

The pressure within each individual heat exchange channel in the microchannel reactor 100 may be controlled using passive structures (e.g., obstructions), orifices and/or mechanisms upstream of the heat exchange channels or in the channels. By controlling the pressure within each heat exchange channel, the temperature within each heat exchange channel can be controlled. A higher inlet pressure for each heat exchange channel may be used where the passive structures, orifices and/or mechanisms let down the pressure to the desired pressure. By controlling the temperature within each heat exchange channel, the temperature in the process microchannels may be controlled. Thus, for example, each process microchannel may be operated at a desired temperature by employing a specific pressure in the heat exchange channel adjacent to or in thermal contact with the process microchannel. This may provide the advantage of precisely controlled temperatures for each process microchannel. The use of precisely controlled temperatures for each process microchannel provides the advantage of a tailored temperature profile and an overall reduction in the energy requirements for the process.

In a scale up device, for certain applications, it may be required that the mass of the process fluid be distributed uniformly among the microchannels. Such an application may be when the process fluid is required to be cooled down with adjacent heat exchange channels. The uniform mass flow distribution may be obtained by changing the cross-sectional area from one parallel microchannel to another microchannel. The uniformity of mass flow distribution may be defined by Quality Index Factor (Q-factor) as indicated below. A Q-factor of 0% means absolute uniform distribution.

$$Q = \frac{\dot{m}_{max} - \dot{m}_{min}}{\dot{m}_{max}} \times 100$$

A change in the cross-sectional area may result in a difference in shear stress on the wall. In one embodiment, the Q-factor for the microchannel reactor 100 may be less than about 50%, and in one embodiment less than about 20%, and in one embodiment less than about 5%, and in one embodiment less than about 1%.

The free stream velocity for process fluid flowing in the process microchannels may be at least about 0.001 m/s, and in one embodiment at least about 0.01 m/s, and in one embodiment in the range from about 0.001 to about 200 m/s, and in one embodiment in the range from about 0.01 to about 100 m/s, and in one embodiment in the range from about 0.01 to about 200 m/s.

The product formed by the inventive process comprises ethylene oxide. Advantages of the inventive process include: maximization of contact between the ethylene and oxygen or source of oxygen, and the catalyst; and minimization of homogenous gas-phase unselective reactions, such as those which convert the ethylene or ethylene oxide to carbon oxides ($CO$ and $CO_2$). In one embodiment, selectivity to carbon oxides (on a carbon atom basis) may be less than about 0.5 mole of carbon oxides per mole of ethylene oxide.

Advantages of the inventive process may include the potential for process intensification. Conventional processes of the prior art (that is, non-microchannel processes) often operate under conditions of reactant dilution to prevent runaway reactions, while the inventive process may be operated, if desired, under more intense conditions leading to greater throughput. By combining catalytic microchannel processing with heat exchange it is possible to operate at ethylene/oxygen ratios that would conventionally lead to high temperatures and loss of selectivity, but by removing heat rapidly through heat exchange, the temperature in the process microchannels may be maintained relatively low, for example, below about 265° C., and in one embodiment below about 250° C., and in one embodiment below about 240° C., thus maximizing selectivity to the desired ethylene oxide.

Advantages of the inventive process include the enhancement of reaction selectivity due to the dimensions of the microchannel reactor. In reactors of conventional dimension (that is, non-microchannel reactors), reactions propagated homogeneously in the in the gaseous phase make a significant contribution to the overall make-up of the product. These reactions tend to be indiscriminate and often result in the production of undesirable by-products such as $CO$ and $CO_2$ or hydrocarbon pyrolysis products. Significant increases in reaction selectivity to ethylene oxide can be achieved when conducted in a microchannel reactor in accordance with the invention wherein the microchannel reactor has an internal height or width at or near the quench diameter for the reaction in question.

The level of conversion of the ethylene per pass through the microchannel reactor may be up to about 10%, and in one embodiment up to about 20%, and in one embodiment up to about 30%, and in one embodiment up to about 40%, and in one embodiment up to about 50%.

The level of conversion of oxygen per pass through the microchannel reactor may be up to about 10%, and in one embodiment up to about 20%, and in one embodiment up to about 30%, and in one embodiment up to about 40%, and in one embodiment up to about 50% or higher.

The yield of ethylene oxide may be up to about 10% per cycle, and in one embodiment up to about 20%, and in one embodiment up to about 30%, and in one embodiment up to about 40%, and in one embodiment about 50% per cycle. The term "cycle" is used herein to refer to a single pass of the reactants through the microchannel reactor.

In one embodiment, the level of conversion of the ethylene may be up to about 10%, and the level of selectivity to ethylene oxide may be in the range from about 75% to about 95%.

In one embodiment, the level of conversion of the ethylene may be up to about 20%, and the level of selectivity to ethylene oxide may be in the range from about 75% to about 95%.

In one embodiment, the level of conversion of the ethylene may be up to about 30%, and the level of selectivity to ethylene oxide may be in the range from about 75% to about 95%.

In one embodiment, the level of conversion of the ethylene may be up to about 40%, and the level of selectivity to ethylene oxide may be in the range from about 75% to about 95%.

In one embodiment, the process may be conducted in a reactor containing a plurality of heat exchange channels operating in parallel. The total pressure drop for the heat exchange fluid flowing in the heat exchange channels may be up to about 10 bars, and in one embodiment up to about 5 bars, and in one embodiment up to about 2 bars.

EXAMPLES

Figure 28:
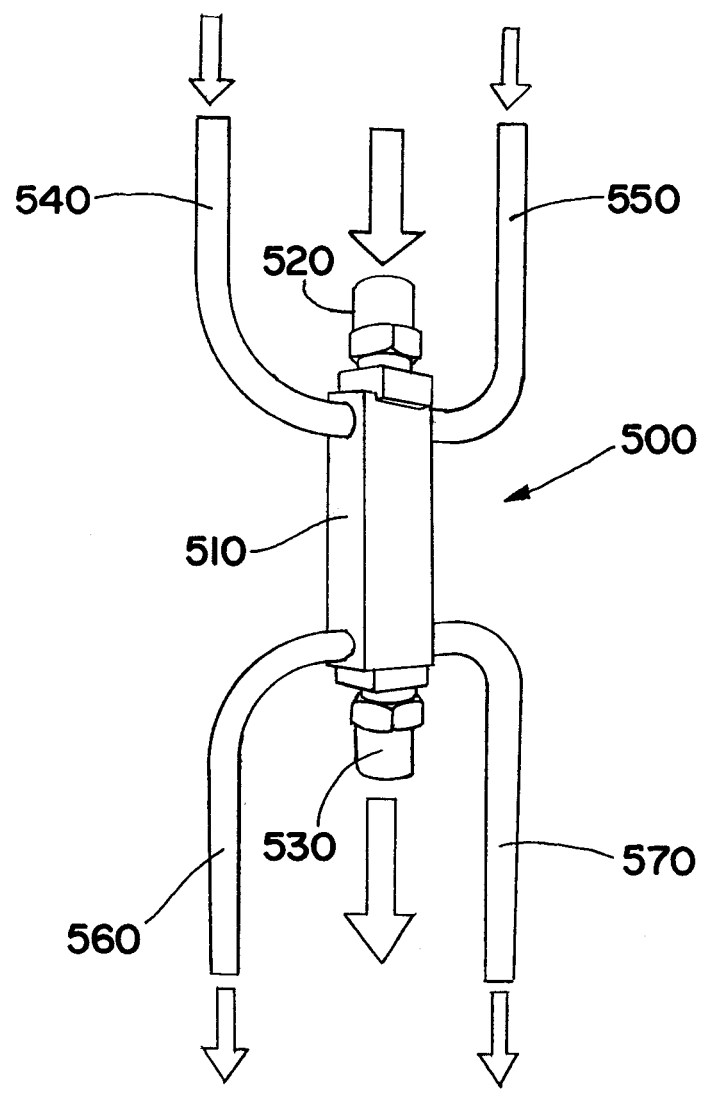
FIG. 28 is a schematic illustration of the microchannel reactor used in the Example.

A process for converting ethylene and oxygen to ethylene oxide is conducted using the microchannel reactor shown in FIG. 28. Referring to FIG. 28, microchannel reactor 500 includes microchannel reactor core 510, reactant inlet 520, product outlet 530, heat exchange fluid inlets 540 and 550, and heat exchange fluid outlets 560 and 570. The microchannel reactor core 510 is made of stainless steel. The microchannel reactor core 510 contains a single process microchannel and two heat exchange channels, the heat exchange channels being positioned on each side of the process microchannel. The process microchannel has a feed inlet and a product outlet.

Ethylene, oxygen, methane, carbon dioxide, nitrogen (tracer), and ethyl chloride are mixed using a set of flow controllers to form a reactant feed stream. There are two separate feed streams which are combined while forming the reactant feed stream. One of the feed streams is an ethylene stream which also contains methane, carbon dioxide and ethyl chloride. The ethyl chloride is introduced using a doped methane stream which contains 20 ppm by volume ethyl chloride. The other feed stream is an oxygen stream which contains nitrogen (tracer). The reactant feed stream enters the microchannel reactor as shown in FIG. 28, and undergoes a reaction to form a product comprising ethylene oxide. The product flows out of the microchannel reactor 500 as shown in FIG. 28. The feed stream entering the microchannel reactor 500 and the product flowing out of the microchannel reactor 500 are analyzed using a Hewlett Packard 5890 series II gas chromatograph.

Figure 30:
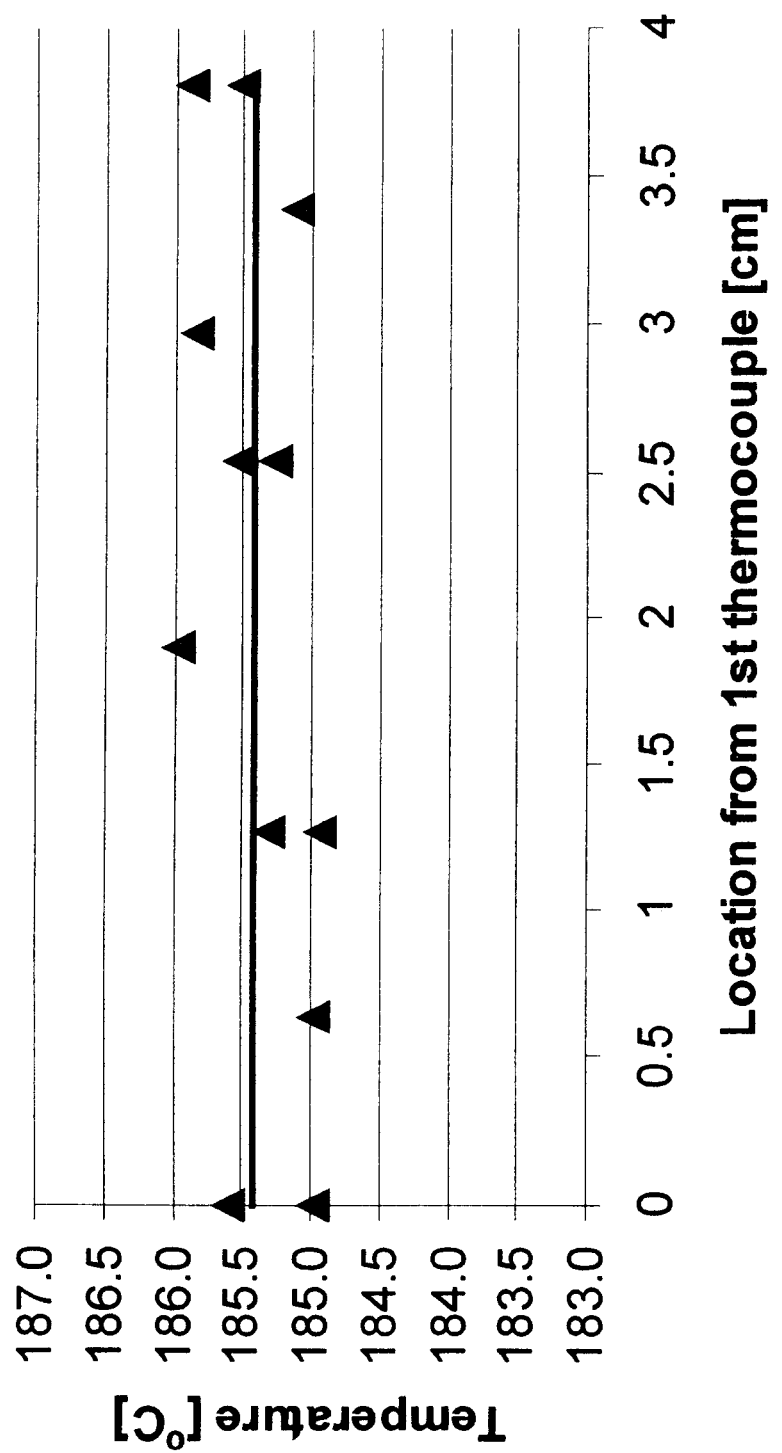
FIG. 30 is a chart showing a thermal profile for the microchannel reactor used in the Example.

The process microchannel has a rectangular cross section with an internal height of 0.025 inch (0.635 mm) or 0.0375 inch (0.95 mm) as indicated below. The process microchannel has an internal width of 0.3 inch (0.76 cm) and a length of 2.75 inch (6.99 cm). The heat exchange channels have rectangular cross sections with internal dimensions of 0.030 inch by 0.3 inch (0.76 mm by 0.76 cm). The heat exchange fluid is Marlotherm SH (a heat transfer oil supplied by Sasol). The heat exchange fluid flows through the heat exchange channels at a rate of 5-7 liters per minute (lpm). The flow of the heat exchange fluid is turbulent and sufficient to provide the process microchannel with a substantially isothermal temperature profile. The microchannel reactor core 510 contains an array of 12 thermocouples for measuring temperature. The temperature measurements for one test run are shown in FIG. 30.

Figure 29:
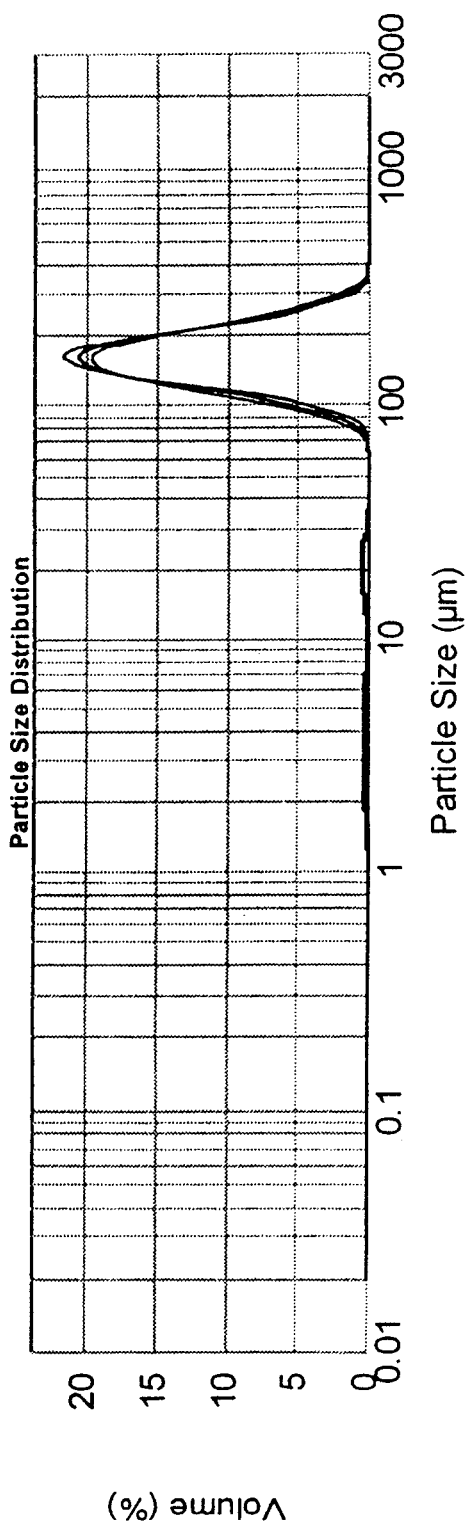
FIG. 29 is a graph showing the particle size distribution of the catalyst used in the Example. The graph shows the results for three samples.

The catalysts are crushed and sieved to a desired particle size in the US 50-120 mesh range. The particle size distribution for three samples of one of the catalysts, in the US 100-120 mesh range, is shown in FIG. 29. The catalysts are in the form of a bed of particulate solids packed in the process microchannel. Additionally, inert particulates are packed in the process microchannel on each side of the catalyst bed. The inert particulates comprise silicon carbide or steatite particulates having an average diameter of about 100 µm. The bed of particulates (i.e., catalyst particulates and inert particulates) is held in place with two stainless steel guard screens positioned on each side of the bed. One of the screens has a US 30 mesh size and the other has a US 200 mesh size.

The reactor is loaded by first placing the stainless steel guard screens in the product outlet of the process microchannel. Inert particulates (e.g., silicon carbide or steatite) are then loaded in the process microchannel, followed by the catalyst particulates, and then a final layer of inert particulates using gravity and/or suction techniques. Mechanical techniques may be used in packing the bed. Stainless steel guard screens are then placed in the feed inlet of the process microchannel.

The loaded reactor is installed in a test stand. The start-up of the process involves first drying the catalyst by flowing dry $N_2$ at atmospheric pressure and a temperature of 220-240° C. through the loaded reactor for about 24 hours at a space velocity of about 4200 $hr^{-1}$. The reactor is then pressurized to the desired operating pressure. The catalyst is activated by flowing a diluted reactant stream containing $N_2$, $C_2H_4$, ethyl chloride, and optionally $CO_2$, through the reactor in contact with the catalyst. The $C_2H_4$ flow is set to the final desired value. Depending on the anticipated catalyst activity, the $CO_2$ level in the diluted reactant stream is set between 0% to 10% and the $N_2$ dilution to a relatively high concentration ranging between 50% to 90% by volume. The concentration of ethyl chloride is set a low value about 2 ppm by volume. Part of the desired oxygen flow is then introduced such that the oxygen concentration in the feed is below 5% by volume. This is followed by replacing the $N_2$ with $CH_4$ step-wise over a period of 1-2 hours. The concentration of ethyl chloride is then increased to the target level. The remainder of the oxygen feed is brought on-line step-wise over a period of 2-4 hours. The reactor temperature is increased by 10 to 20° C. over a period of 0.5 hours. The reactor is maintained under these conditions for a period of 24 hours. The concentration of $CH_4$ is decreased in steps of 1% to the reach target level. At each step the reactor is maintained under the indicated conditions for a period of 1-2 hours. This is followed by a step-wise lowering of the $CO_2$ level to the desired value. The hold time after each step is about 1-2 hours. This completes the start-up procedure. The reaction conditions are then changed to those indicated in the examples below.

Example 1

0.37 g of a high selectivity catalyst and 0.15 g of steatite are loaded in the process microchannel to provide a catalyst bed and two beds of inert particulates. One of the beds of inert particulates is upstream of the catalyst bed and the other bed of inert particulates is downstream of the catalyst bed. The catalyst bed length is 2.14 inches (5.4 cm). The length of the bed of inert particulates upstream of the catalyst bed is 0.31 inch (0.787 cm). The length of the bed of inert particulates downstream of the catalyst bed is 0.30 inch (0.762 cm). The internal height of the process microchannel is 0.0375 inch (0.95 mm). The catalyst contains silver and a promoting amount of rhenium. The catalyst is supported on an alpha-aluminum oxide support. The reactant composition contains:

| | |
|---|---|
| ethylene | 50 mole % |
| oxygen | 25 mole % |
| ethyl chloride | 2.2 parts per million (ppm) by volume |
| nitrogen | 5 mole % |
| methane | balance |

The gas hourly space velocity (GHSV) for the flow of process fluid through the process microchannel is 16,000 $hr^{-1}$. At a pressure of 16 bars (absolute pressure) and a temperature of 185° C., a workrate of 250 kilograms of ethylene oxide per cubic meter of catalyst per hour ($Kg_{EO}/m^3_{cat}/hr$) is obtained with the selectivity to ethylene oxide being 89.5%.

Example 2

0.37 g. of the catalyst used in Example 1 and 0.15 g of steatite are loaded in the process microchannel to provide a catalyst bed and two beds of inert particulates. One of the beds of inert particulates is upstream of the catalyst bed and the other bed of inert particulates is downstream of the catalyst bed. The catalyst bed length is 2.14 inches (5.4 cm). The length of the bed of inert particulates upstream of the catalyst bed is 0.31 inch (0.787 cm). The length of the bed of inert particulates downstream of the catalyst bed is 0.30 inch (0.762 cm). The internal height of the process microchannel is 0.0375 inch (0.95 mm). The catalyst volume is 0.395 ml. The reactant composition contains:

| | |
|---|---|
| ethylene | 50 mole % |
| oxygen | 25 mole % |
| ethyl chloride | 2.2 parts per million (ppm) by volume |
| nitrogen | 5 mole % |
| methane | balance |

The GHSV for the flow of process fluid in the process microchannel is 16,000 hr$^{-1}$. After 3000 hours time-on-stream at a pressure of 16 bars (absolute) and a temperature of 230° C., a workrate of 770 Kg$_{EO}$/m$^3_{cat}$/hr is obtained with a selectivity to ethylene oxide of 90.1%.

Example 3

0.18 g. of a high activity catalyst and 0.27 g of silicon carbide are loaded in the process microchannel to provide a catalyst bed and two beds of inert particulates. One of the beds of inert particulates is upstream of the catalyst bed and the other bed of inert particulates is downstream of the catalyst bed. The catalyst bed length is 1.5 inches (3.8 cm). The length of the bed of inert particulates upstream of the catalyst bed is 0.65 inch (1.651 cm). The length of the bed of inert particulates downstream of the catalyst bed is 0.6 inch (1.524 cm). The process microchannel has an internal height of 0.025 inch (0.635 mm). The catalyst contains silver and a promoting amount of cesium. The catalyst is supported on an alpha-aluminum oxide support. The catalyst volume is 0.184 ml. The reactant composition contains:

| | |
|---|---|
| ethylene | 37.50 mole % |
| oxygen | 12.50 mole % |
| ethyl chloride | 2.7 parts per million (ppm) by volume |
| nitrogen | 5 mole % |
| methane | balance |

The GHSV for the flow of process fluid in the process microchannel is 22,500 hr$^{-1}$. At a pressure of 16 bars (absolute) and a temperature of 248° C., a workrate of 1310 Kg$_{EO}$/m$^3_{cat}$/hr is obtained with a selectivity to ethylene oxide of 88.5%.

Example 4

0.18 g. of the catalyst used in Example 3 and 0.27 g of silicon carbide are loaded in the process microchannel to provide a catalyst bed and two beds of inert particulates. One of the beds of inert particulates is upstream of the catalyst bed and the other bed of inert particulates is downstream of the catalyst bed. The catalyst bed length is 1.5 inches (3.8 cm). The length of the bed of inert particulates upstream of the catalyst bed is 0.65 inch (1.651 cm). The length of the bed of inert particulates downstream of the catalyst bed is 0.6 inch (1.524 cm). The process microchannel has an internal height of 0.025 inch (0.635 mm). The catalyst volume is 0.184 ml. The reactant composition contains:

| | |
|---|---|
| ethylene | 41.70 mole % |
| oxygen | 8.30 mole % |
| ethyl chloride | 2.7 parts per million (ppm) by volume |
| nitrogen | 5 mole % |
| methane | balance |

The GHSV for the flow of process fluid in the process microchannel is 22,500 hr$^{-1}$. At a pressure of 16 bars (absolute) and a temperature of 247° C., a workrate of 940 Kg$_{EO}$/m$^3_{cat}$/hr is obtained with a selectivity to ethylene oxide of 88.5%.

Example 5

0.50 g of a high activity catalyst and 0.16 g of steatite are loaded in the process microchannel to provide a catalyst bed and two beds of inert particulates. One of the beds of inert particulates is upstream of the catalyst bed and the other bed of inert particulates is downstream of the catalyst bed. The catalyst bed length is 2.2 inches (5.6 cm). The length of the bed of inert particulates upstream of the is catalyst bed is 0.25 inch (0.635 cm). The length of the bed of inert particulates downstream of the catalyst bed is 0.3 inch (0.762 cm). The process microchannel has an internal height of 0.0375 inch (0.95 mm). The catalyst contains silver and a promoting amount of cesium. The catalyst is supported in an alpha-aluminum oxide support. The catalyst volume is 0.406 ml. The reactant composition contains:

| | |
|---|---|
| ethylene | 41.70 mole % |
| oxygen | 8.30 mole % |
| ethyl chloride | 2.7 parts per million (ppm) by volume |
| nitrogen | 5 mole % |
| methane | balance |

The GHSV for the flow of process fluid in the process microchannel is 22,500 hr$^{-1}$. At a pressure of 16 bars (absolute) and a temperature of 195° C., a workrate of 235 Kg$_{EO}$/m$^3_{cat}$/hr is obtained with a selectivity to ethylene oxide of 90.3%.

Example 6

0.26 g of an intermediate selectivity catalyst and 0.19 g of silicon carbide are loaded in the process microchannel to provide a catalyst bed and two beds of inert particulates. One of the beds of inert particulates is upstream of the catalyst bed and the other bed of inert particulates is downstream of the catalyst bed. The catalyst bed length is 1.85 inches (4.7 cm). The length of the bed of inert particulates upstream of the catalyst bed is 0.6 inch (1.524 cm). The length of the bed of inert particulates downstream of the catalyst bed is 0.3 inch (0.762 cm). The process microchannel has an internal height of 0.025 inch (0.635 mm). The catalyst contains silver and a promoting amount of rhenium. The catalyst is supported on an alpha-aluminum oxide support. The catalyst volume is 0.227 ml. The reactant composition contains:

| | |
|---|---|
| ethylene | 11 mole % |
| oxygen | 39 mole % |
| ethyl chloride | 2.9 parts per million (ppm) by volume |
| nitrogen | 5 mole % |
| methane | balance |

The GHSV for the flow of process fluid in the process microchannel is 9,000 hr$^{-1}$. At a pressure of 16 bars (absolute) and a temperature of 210° C., a workrate of 180 Kg$_{EO}$/m$^3_{cat}$/hr is obtained with a selectivity to ethylene oxide of 89.5%.

Example 7

0.26 g of the catalyst used in Example 6 and 0.19 g of silicon carbide are loaded in the process microchannel to provide a catalyst bed and two beds of inert particulates. One of the beds of inert particulates is upstream of the catalyst bed and the other bed of inert particulates is downstream of the catalyst bed. The catalyst bed length is 1.85 inches (4.7 cm). The length of the bed of inert particulates upstream of the catalyst bed is 0.6 inch (1.524 cm). The length of the bed of particulate solids downstream of the catalyst bed is 0.3 inch (0.762 cm). The process microchannel has an internal height of 0.025 inch (0.635 mm). The catalyst volume is 0.227 ml. The reactant composition contains:

| | |
|---|---|
| ethylene | 25 mole % |
| oxygen | 25 mole % |
| ethyl chloride | 2.9 parts per million (ppm) by volume |
| nitrogen | 5 mole % |
| methane | balance |

The GHSV for the flow of process fluid in the process microchannel is 9,000 hr$^{-1}$. At a pressure of 16 bars (absolute) and a temperature of 210° C., a workrate of 190 Kg$_{EO}$/m$^3_{cat}$/hr is obtained with a selectivity to ethylene oxide of 91.0%.

Example 8

0.50 g of the catalyst used in Example 5 and 0.16 g of steatite are loaded in the process microchannel to provide a catalyst bed and two beds of inert particulates. One of the beds of inert particulates is upstream of the catalyst bed and the other bed of inert particulates is downstream of the catalyst bed. The catalyst bed length is 2.2 inches (5.6 cm). The length of the bed of inert particulates upstream of the catalyst bed is 0.25 inch (0.635 cm). The length of the bed of inert particulates downstream of the catalyst bed is 0.3 inch (0.762 cm). The process microchannel has an internal height of 0.0375 inch (0.95 mm). The catalyst volume is 0.406 ml. The reactant composition contains:

| | |
|---|---|
| ethylene | 19 mole % |
| oxygen | 10 mole % |
| ethyl chloride | 2.7 parts per million (ppm) by volume |
| nitrogen | 5 mole % |
| methane | balance |

The GHSV for the flow of process fluid in the process microchannel is 22,500 hr$^{-1}$. At a pressure of 16 bars (absolute) and a temperature of 235° C., a workrate of 750 Kg$_{EO}$/m$^3_{cat}$/hr is obtained with a selectivity to ethylene oxide of 89.1%.

Example 9

0.45 g of the catalyst used in Example 5 and 0.15 g of steatite are loaded in the process microchannel to provide a catalyst bed and two beds of inert particulates. One of the beds of inert particulates is upstream of the catalyst bed and the other bed of inert particulates is downstream of the catalyst bed. The catalyst bed length is 2.2 inches (5.6 cm). The length of the bed of inert particulates upstream of the catalyst bed in 0.25 inch (0.635 cm). The length of the bed of inert particulates downstream of the catalyst bed is 0.3 inch (0.762 cm). The process microchannel has an internal height of 0.0375 inch (0.95 mm). The catalyst volume is 0.406 ml. The reactant composition contains:

| | |
|---|---|
| ethylene | 33.9 mole % |
| oxygen | 6.7 mole % |
| ethyl chloride | 2.7 parts per million (ppm) by volume |
| nitrogen | 4.4 mole % |
| carbon dioxide | 4.9 mole % |
| methane | balance |

The GHSV for the flow of process fluid in the process microchannel is 22,500 hr$^{-1}$. At a pressure of 16 bars (absolute) and a temperature of 225° C., a workrate of 245 Kg$_{EO}$/m$^3_{cat}$/hr is obtained with a selectivity to ethylene oxide of 90.5%.

Example 10

0.36 g of the catalyst used in Example 1 and 0.16 g of steatite are loaded in the process microchannel to provide a catalyst bed and two beds of inert particulates. One of the beds of inert particulates is upstream of the catalyst bed and the other bed of inert particulates is downstream of the catalyst bed. The catalyst bed length is 2.2 inches (5.6 cm). The length of the bed of inert particulates upstream of the catalyst bed is 0.25 inch (0.635 cm). The length of the bed of inert particulates downstream of the catalyst bed is 0.3 inch (0.762 cm). The process microchannel has an internal height of 0.0375 inch (0.95 mm). The catalyst volume is 0.406 ml. The reactant composition contains:

| | |
|---|---|
| ethylene | 18.5 mole % |
| oxygen | 9.2 mole % |
| ethyl chloride | 2.2 parts per million (ppm) by volume |
| nitrogen | 4.5 mole % |
| methane | balance |

The GHSV for the flow of process fluid in the process microchannel is 16,000 hr$^{-1}$. At a pressure of 16 bars (absolute) and a temperature of 225° C., a workrate of 245 Kg$_{EO}$/m$^3_{cat}$/hr is obtained with a selectivity to ethylene oxide of 92.5%.

Example 11

0.36 g of the catalyst used in Example 1 and 0.16 g of steatite are loaded in the process microchannel to provide a catalyst bed and two beds of inert particulates. One of the beds of inert particulates is upstream of the catalyst bed and the other bed of inert particulates is downstream of the catalyst bed. The catalyst bed length is 2.2 inches (5.6 cm). The length of the bed of inert particulates upstream of the catalyst bed is 0.25 inch (0.635 cm). The length of the bed of particulate solids downstream of the catalyst bed is 0.3 inch (0.762 cm). The process microchannel has an internal height of 0.0375 inch (0.95 mm). The catalyst volume is 0.406 ml. The reactant composition contains:

| | |
|---|---|
| ethylene | 27.9 mole % |
| oxygen | 9.1 mole % |

| | |
|---|---|
| ethyl chloride | 2.2 parts per million (ppm) by volume |
| nitrogen | 4.5 mole % |
| methane | balance |

The GHSV for the flow of process fluid in the process microchannel is 16,000 hr$^{-1}$. At a pressure of 16 bars (absolute) and a temperature of 225° C., a workrate of 280 Kg$_{EO}$/m$^3_{cat}$/hr is obtained with a selectivity to ethylene oxide of 92.4%.

Example 12

0.36 g of the catalyst used in Example 1 and 0.16 g of steatite are loaded in the process microchannel to provide a catalyst bed and two beds of inert particulates. One of the beds of inert particulates is upstream of the catalyst bed and the other bed of inert particulates is downstream of the catalyst bed. The catalyst bed length is 2.2 inches (5.6 cm). The length of the bed of inert particulates upstream of the catalyst bed is 0.25 inch (0.635 cm). The length of the bed of inert particulates downstream of the catalyst bed is 0.3 inch (0.762 cm). The process microchannel has an internal height of 0.0375 inch (0.95 mm). The catalyst volume is 0.406 ml. The reactant composition contains:

| | |
|---|---|
| ethylene | 44.7 mole % |
| oxygen | 9.1 mole % |
| ethyl chloride | 2.2 parts per million (ppm) by volume |
| nitrogen | 4.3 mole % |
| methane | balance |

The GHSV for the flow of process fluid in the process microchannel is 16,000 hr$^{-1}$. At a pressure of 16 bars (absolute) and a temperature of 225° C., a workrate of 330 Kg$_{EO}$/m$^3_{cat}$/hr is obtained with a selectivity to ethylene oxide of 91.4%.

Example 13

0.36 g of the catalyst from Example 1 and 0.16 g of steatite are loaded in the process microchannel to provide a catalyst bed and two beds of inert particulates. One of the beds of inert particulates is upstream of the catalyst bed and the other bed of inert particulates is downstream of the catalyst bed. The catalyst bed length is 2.2 inches (5.6 cm). The length of the bed of inert particulates upstream of the catalyst bed is 0.25 inch (0.635 cm). The length of the bed of inert particulates downstream of the catalyst bed is 0.3 inch (0.762 cm). The process microchannel has an internal height of 0.0375 inch (0.95 mm). The catalyst volume is 0.406 ml. The reactant composition contains:

| | |
|---|---|
| ethylene | 62.8 mole % |
| oxygen | 9.2 mole % |
| ethyl chloride | 2.2 parts per million (ppm) by volume |
| nitrogen | 4.8 mole % |
| methane | balance |

The GHSV for the flow of process fluid in the process microchannel is 16,000 hr$^{-1}$. At a pressure of 16 bars (absolute) and a temperature of 225° C., a workrate of 350 Kg$_{EO}$/m$^3_{cat}$/hr is obtained with a selectivity to ethylene oxide of 91.2%.

Example 14

Two different runs with the catalyst from Example 5 are carried out. Both runs include a start-up procedure that starts with a feed stream having a high concentration of diluent and $CO_2$. These are gradually lowered to the desired value. One run employs a high temperature hold during the start-up while the other run is does not. A comparison of the performance for each run indicates that the high temperature hold provides for enhanced catalyst activity when compared to the run without the high temperature holds.

| High temperature hold at startup | No | Yes |
|---|---|---|
| Operating Condition | | |
| Temperature [° C.] | 215 | 210 |
| Contact Time [ms] | 554 | 160 |
| $C_2$:$O_2$ ratio in feed | 5 | 5 |
| Dilution in feed | 54% | 50% |
| $CO_2$ in feed | 1% | 1% |
| Performance | | |
| $C_2H_4$ Conversion | 2.7% | 1.4% |
| EO Selectivity | 83.7% | 92.7% |
| Productivity [kgEO/m$^3_{cat}$/hr] | 90 | 235 |

Example 15

Two different runs with the catalyst from Example 3 are carried out. Both runs include a high temperature hold. However, they differ in that one run employs a gentle start-up procedure that starts with high concentration of diluent and a high $CO_2$ content in the feed stream. These are gradually lowered to the desired value. The other run does not employ the gentle start-up using the high concentrations of diluent and $CO_2$. During start-up for the run that does not employ the gentle start-up procedure, a high oxygen conversion (>90%) is observed. A comparison of the performance (at 310 hours on stream) shows that the gentle start-up provides enhanced catalyst activity.

| Gentle Start-up | No | Yes |
|---|---|---|
| Operating Condition | | |
| Temperature [° C.] | 210 | 201 |
| Contact Time [ms] | 160 | 160 |
| $C_2$:$O_2$ ratio in feed | 5 | 5 |
| Dilution in feed | 50% | 50% |
| Performance | | |
| $C_2H_4$ Conversion | 1.5% | 1.6% |
| EO Selectivity | 90.0% | 89.7% |
| Productivity [kgEO/m$^3_{cat}$/hr] | 279 | 236 |

Example 16

Three production runs are conducted using the microchannel reactor illustrated in FIG. 28. For each production run, 0.37 g of the catalyst used in Example 1 and 0.15 g of steatite are used to provide a catalyst bed, and beds of inert particulates upstream and downstream of the catalyst bed. The catalyst bed length is 2.14 inches (5.4 cm). The inert particulate bed upstream of the catalyst bed has a length of 0.31 inch (0.787 cm). The inert particulate bed downstream of the catalyst bed has a length of 0.3 inch (0.762 cm). The catalyst volume is 0.395 ml. The reactant composition contains:

| | |
|---|---|
| ethylene | 50 mole % |
| oxygen | 25 mole % |
| ethyl chloride | 2.2 parts per million (ppm) by volume |
| nitrogen | 5 mole % |
| methane | balance |

The process is conducted under the conditions shown in the table below. For each production run the selectivity to ethylene oxide is 89.5% or higher.

| Workrate ($Kg_{EO}/m^3cat/hr$) | $T_{SOR}$ (° C.) | $T_{EOR}$ (° C.) | Productivity ($kg_{EO}/m^3_{cat}$) | Hours on Stream |
|---|---|---|---|---|
| 0.25 | 185 | 265 | 6261 | 25046 |
| 0.50 | 201 | 265 | 2424 | 4849 |
| 0.75 | 217 | 265 | 702 | 936 |

Example 17

Comparative test runs for converting ethylene to ethylene oxide are conducted using a microchannel reactor and a conventional reactor. The conventional reactor is a single miniplant tubular reactor. For each production run, the end of run temperature ($T_{EOR}$) is 265° C. Comparisons for time on stream are made at the same work rate of 0.25 kilotons of ethylene oxide per cubic meter of catalyst per hour ($kt_{EO}/m^3_{cat}/hr$). The microchannel reactor process is also conducted at 2.68 times the work rate, that is, a work rate of 0.67 $kt_{EO}/m^3_{cat}/hr$. The results are shown in the table below.

| | Conventional reactor | Microchannel reactor | |
|---|---|---|---|
| Work rate [$kt_{EO}/m^3_{cat}/h$] | 0.25 | 0.67 | 0.25 |
| Time-on-stream [h] | 7000 | 3200 | 25000 |
| EO production [$kt_{EO}/m^3_{cat}/h$] | 1.75 | 1.75 | 6.25 |
| Potential | | High capacity | Long catalyst life |

The above results indicate that in a process for converting ethylene to ethylene oxide using a microchannel reactor it is possible to increase the work rate of the catalyst by a factor of about 2.68 (i.e., 0.67÷0.25=2.68) as compared to a conventional reactor and in so doing obtain the same production of ethylene oxide over a period of time (time-on-stream) that is about 45.7% (i.e., 3200÷7000×100%=45.7%) of that required for the conventional reactor. The results also indicate that it is possible to increase catalyst life by a factor of about 3.571 (i.e., 6.25÷1.75=3.571) at the same work rate. The results indicate that it is possible to increase ethylene oxide production by a factor of about 3.571 using the same catalyst and catalyst volume.

While the invention has been explained in relation to various embodiments, it is to be understood that various modifications thereof will become apparent to those skilled in the art upon reading the specification. Therefore, it is to be understood that the invention disclosed herein is intended to cover such modifications as fall within the scope of the appended claims.

The invention claimed is:

1. A process, comprising:
reacting ethylene and oxygen or a source of oxygen in the presence of an olefin epoxidation catalyst in a plurality of process microchannels in a microchannel reactor to form a product comprising ethylene oxide during a production run, the catalyst being in the form of particulate solids, the production run continuing until at least about 2 kilotons of ethylene oxide are produced per cubic meter of catalyst, the selectivity to ethylene oxide being in the range from about 75% to about 95%; and
replacing and/or regenerating the catalyst at the end of the production run;
wherein the microchannel reactor further comprises a plurality of heat exchange channels, the heat exchange channels exchanging heat with the process microchannels.

2. A process, comprising:
reacting ethylene and oxygen or a source of oxygen in the presence of an olefin epoxidation catalyst in a plurality of process microchannels in a microchannel reactor during a production run to form a product comprising ethylene oxide at a rate in the range from about 450 to about 5000 kilograms of ethylene oxide per cubic meter of catalyst per hour, the catalyst being in the form of particulate solids;
wherein the microchannel reactor further comprises a plurality of heat exchange channels, the heat exchange channels exchanging heat with the process microchannels.

3. A process, comprising:
reacting ethylene and oxygen or a source of oxygen in the presence of an olefin epoxidation catalyst in a plurality of process microchannels in a microchannel reactor in a production run to form a product comprising ethylene oxide at a rate of at least about 250 kilograms of ethylene oxide per cubic meter of catalyst per hour, the production run continuing until at least about 2 kilotons of ethylene oxide is produced per cubic meter of catalyst, the catalyst being in the form of particulate solids, the selectivity to ethylene oxide being at least about 80%, the catalyst being in a reaction zone in each of the process microchannels; and
maintaining an average temperature in the reaction zones below about 220° C.;
wherein the microchannel reactor further comprises a plurality of heat exchange channels, the heat exchange channels exchanging heat with the process microchannels.

4. A process, comprising:
reacting ethylene and oxygen or a source of oxygen in the presence of an olefin epoxidation catalyst in a plurality of process microchannels in a microchannel reactor in a production run to form a product comprising ethylene oxide at a rate of at least about 250 kilograms of ethylene oxide per cubic meter of catalyst per hour, the production run continuing until at least about 2 kilotons of ethylene oxide is produced per cubic meter of catalyst, the catalyst being in the form of particulate solids, the selectivity to ethylene oxide being at least about 80%, the catalyst being in a reaction zone in each process microchannel; and
maintaining an average temperature in the reaction zones above about 265° C.;

wherein the microchannel reactor further comprises plurality of heat exchange channels, the heat exchange channels exchanging heat with the process microchannels.

5. A process, comprising:

reacting ethylene and oxygen or a source of oxygen in the presence of an olefin epoxidation catalyst in a plurality of process microchannels in a microchannel reactor to form a product comprising ethylene oxide, the catalyst being in the form of particulate solids, the catalyst being in a reaction zone in each of the process microchannels, the ethylene oxide being produced during a production run, the average temperature in the reaction zones at the start of the production run being at least about 150° C.;

increasing the temperature in the reaction zones during the production run at a sufficient rate to maintain an average production rate of at least about 250 kilograms of ethylene oxide per cubic meter of catalyst per hour, the production run being continued until at least about 2 kilotons of ethylene oxide is produced per cubic meter of catalyst; and replacing and/or regenerating the catalyst at the end of the production run;

wherein the microchannel reactor further comprises a plurality of heat exchange channels, the heat exchange channels exchanging heat with the process microchannels.

6. The process of claim 1 wherein the selectivity to ethylene oxide is in the range from about 85 to about 95%.

7. The process of claim 1 wherein the selectivity to ethylene oxide is in the range from about 80 to about 95%.

8. The process of claim 1 wherein the ethylene oxide is produced at a rate of at least about 250 kilograms of ethylene oxide per cubic meter of catalyst per hour.

9. The process of claim 1 wherein the ethylene oxide is produced at a rate of at least about 300 kilograms of ethylene oxide per cubic meter of catalyst per hour.

10. The process of claim 1 wherein the ethylene oxide is produced at a rate of at least about 400 kilograms of ethylene oxide per cubic meter of catalyst per hour.

11. The process of claim 1 wherein the ethylene oxide is produced at a rate in the range from about 300 to about 5000 kilograms per cubic meter of catalyst per hour.

12. The process of claim 2 wherein the ethylene and oxygen or a source of oxygen are reacted in the presence of the catalyst until at least about 0.5 kilotons of ethylene oxide are produced per cubic meter of catalyst.

13. The process of claim 1 wherein the ethylene and oxygen or a source of oxygen are reacted in the presence of the catalyst until at least about 3 kilotons of ethylene oxide are produced per cubic meter of catalyst.

14. The process of claim 1 wherein the ethylene and oxygen or a source of oxygen are reacted in the presence of the catalyst until from about 2 to 10 kilotons of ethylene oxide are produced per cubic meter of catalyst.

15. The process of claim 1 wherein the ethylene and oxygen or source of oxygen are reacted in the presence of the catalyst to form ethylene oxide during a production run, the rate of production of ethylene oxide at the start of the production run being at least about 250 kilograms of ethylene oxide per cubic meter of catalyst per hour, the production run continuing until: the selectivity to ethylene oxide decreases to a level below about 84%; and/or the rate of production of ethylene oxide decreases to a level below about 245 kilograms of ethylene oxide per cubic meter of catalyst.

16. The process of claim 1 wherein the catalyst is in a reaction zone in each process microchannel, the average temperature in the reaction zones at the start of a production run being in the range from about 150° C. to about 265° C.

17. The process of claim 3 wherein the average temperature in the reaction zones at the start of a production run is in the range from about 150° C. to about 210° C.

18. The process of claim 4 wherein the average temperature in the reaction zones at the start of a production run is in the range from about 150° C. to about 265° C.

19. The process of claim 5 wherein the average temperature in the reaction zones at the start of a production run is in the range from about 150° C. to about 265° C.

20. The process of claim 1 wherein the ethylene is formed upstream of the microchannel reactor by converting ethane to ethylene.

21. The process of claim 1 wherein the ethylene is formed in the microchannel reactor by converting ethane to ethylene.

22. The process of claim 1 wherein part of the microchannel reactor is used for ethylene formation and part of the microchannel reactor is used for ethylene oxide formation, the ethylene being formed by converting ethane to ethylene.

23. The process of claim 1 wherein at least part of the ethylene oxide is converted to ethylene glycol.

24. The process of claim 23 wherein the ethylene glycol is formed downstream of the microchannel reactor.

25. The process of claim 23 wherein the ethylene glycol is formed in the microchannel reactor.

26. The process of claim 1 wherein the process further comprises quenching the product.

27. The process of claim 26 wherein the product is quenched downstream of the microchannel reactor.

28. The process of claim 26 wherein the product is quenched in the microchannel reactor.

29. The process of claim 1 wherein the ethylene and/or oxygen or source of oxygen are combined with at least one diluent material.

30. The process of claim 1 wherein the ethylene and/or oxygen or source of oxygen are combined with at least one organic halide.

31. The process of claim 30 wherein the organic halide comprises ethyl chloride and/or vinyl chloride.

32. The process of claim 1 wherein the process fluids entering the process microchannels comprise on a whole feed basis from about 10% to about 75% by volume ethylene, at least about 5% by volume oxygen or a source of oxygen, and up to about 100 parts per million by volume of an alkyl halide.

33. The process of claim 1 wherein the contact time in the process microchannels is in the range from about 50 to about 900 milliseconds.

34. The process of claim 1 wherein the catalyst is in a reaction zone in each process microchannel, the average temperature in the reaction zones being in the range from about 150° C. to about 265° C.

35. The process of claim 1 wherein the pressure in the process microchannels is in the range from about 5 to about 30 bar.

36. The process of claim 1 wherein the space velocity in the process microchannels is in the range from about 1000 to about 50,000 hr.$^{-1}$.

37. The process of claim 1 wherein the ethylene oxide and oxygen or source of oxygen comprise reactants and the process microchannels have reaction zones, the reactants contacting each other in the reaction zones.

38. The process of claim 1 wherein the ethylene oxide and oxygen or source of oxygen comprise reactants and the process microchannels have mixing zones and a reaction zones, the mixing zones being upstream of the reaction zones, the reactants contacting each other in the mixing zones.

39. The process of claim 1 wherein the ethylene oxide and oxygen or source of oxygen comprise reactants and the process microchannels have mixing zones and reaction zones, the mixing zones being upstream of the reaction zones, part of one reactant contacting the other reactant in the mixing zones to form an intermediate reaction mixture, the intermediate reaction mixture flowing into the reaction zones, and part of the one reactant contacting the intermediate reaction mixture in the reaction zones.

40. The process of claim 1 wherein a heat exchange fluid is in the heat exchange channels, and wherein the heat exchange fluid undergoes a phase change in the heat exchange channels.

41. The process of claim 1 wherein a heat exchange fluid is in the heat exchange channels, and wherein the heat exchange fluid undergoes partial boiling in the heat exchange channels.

42. The process of claim 1 wherein an endothermic chemical reaction is conducted in the heat exchange channels.

43. The process of claim 42 wherein the endothermic chemical reaction comprises a steam reforming reaction or a dehydrogenation reaction.

44. The process of claim 1 wherein a fluid flows in the process microchannels in a first direction, and a heat exchange fluid flows in the heat exchange channels in a second direction, the second direction being cross current relative to the first direction.

45. The process of claim 1 wherein a fluid flows in the process microchannels in a first direction, and a heat exchange fluid flows in the heat exchange channels in a second direction, the second direction being cocurrent or counter-current relative to the first direction.

46. The process of claim 1 wherein a heat exchange fluid is in the heat exchange channels, and wherein the heat exchange fluid comprises air, steam, liquid water, carbon monoxide, carbon dioxide, gaseous nitrogen, liquid nitrogen, gaseous hydrocarbon, liquid hydrocarbon, or a mixture of two or more thereof.

47. The process of claim 1 wherein a heat exchange fluid is in the heat exchange channels, and wherein the heat exchange fluid comprises one or more of the reactants and/or the product.

48. The process of claim 1 wherein tailored heat exchange is provided along the length of the process microchannels to maintain an isothermal temperature profile for the process microchannels.

49. The process of claim 1 wherein the catalyst comprises a graded catalyst.

50. The process of claim 1 wherein the catalyst is in a reaction zone in the process microchannel in the form of a bed of particulate solids, and additional catalyst is washcoated and/or grown on one or more interior walls of the reaction zone.

51. The process of claim 1 wherein the catalyst comprises one or more of Ag, Mo, Re, W, V, Nb, Sb, Sn, Pt, Pd, Cs, Zr, Cr, Mg, Mn, Ni, Co, Ce, an oxide of one or more thereof, or a mixture of two or more thereof.

52. The process of claim 51 wherein the catalyst further comprises a metal, oxide or mixed metal oxide of an alkali or alkaline earth metal, a transition metal, a rare earth metal, a lanthanide, or a mixture of two or more thereof.

53. The process of claim 51 wherein the catalyst further comprises sulfur or an oxide thereof.

54. The process of claim 51 wherein the catalyst further comprises lithium or an oxide thereof.

55. The process of claim 51 wherein the catalyst further comprises a support, the support comprising a metal oxide, silica, mesoporus material, refractory material, or a combination of two or more thereof.

56. The process of claim 1 wherein the catalyst comprises a support, the support comprising alumina.

57. The process of claim 1 wherein the catalyst comprises silver, the amount of silver being in the range up to about 50% by weight of the catalyst.

58. The process of claim 1 wherein the catalyst is supported on a support, the support comprising: at least about 85% by weight of alpha alumina; from about 0.01 to about 6% by weight (measured as the oxide) of an alkaline earth metal in the form of an oxide; from about 0.01 to about 5% by weight (measured as the dioxide) of silicon in the form of an oxide; and from zero to about 10% by weight (measured as the dioxide) of zirconium in the form of an oxide.

59. The process of claim 58 wherein the alkaline earth metal is calcium and/or magnesium.

60. The process of claim 1 wherein the catalyst work rate is at least about 250 kilograms of ethylene oxide per cubic meter of catalyst per hour, the selectivity to ethylene oxide is at least about 88%, and the catalyst productivity is at least about 1 kiloton of ethylene oxide per cubic meter of catalyst.

61. The process of claim 1 wherein the catalyst work rate is at least about 250 kilograms of ethylene oxide per cubic meter of catalyst per hour, the selectivity to ethylene oxide is at least about 87%, and the catalyst productivity is at least about 2 kilotons of ethylene oxide per cubic meter of catalyst.

62. The process of claim 1 wherein the catalyst work rate is at least about 250 kilograms of ethylene oxide per cubic meter of catalyst per hour, the selectivity to ethylene oxide is at least about 85%, and the catalyst productivity is at least about 3 kilotons of ethylene oxide per cubic meter of catalyst.

63. The process of claim 1 wherein the catalyst work rate is at least about 250 kilograms of ethylene oxide per cubic meter of catalyst per hour, the selectivity to ethylene oxide is at least about 83%, and the catalyst productivity is at least about 4 kilotons of ethylene oxide per cubic meter of catalyst.

64. A process, comprising: reacting ethylene and oxygen or a source of oxygen in the presence of an olefin epoxidation catalyst in a plurality of process microchannels in a microchannel reactor during a production run to form a product comprising ethylene oxide at a rate of at least about 250 $Kg/m^3_{cat}$/hr, the production run continuing until at least about 2 kilotons of ethylene oxide are produced per cubic meter of catalyst, the catalyst being in the form of particulate solids, the selectivity to ethylene oxide being at least about 84%, the catalyst being in a reaction zone in each process microchannel; and maintaining an average temperature in the reaction zones below about 220° C.;

wherein the microchannel reactor further comprises a plurality of heat exchange channels, the heat exchange channels exchanging heat with the process microchannels.

65. A process, comprising: reacting ethylene and oxygen or a source of oxygen in the presence of an olefin epoxidation catalyst in a plurality of process microchannels in a microchannel reactor during a production run to form a product comprising ethylene oxide at a rate of at least about 350 $Kg/m^3_{cat}$/hr, the selectivity to ethylene oxide being at least about 80%, the production run continuing until at least about 2 kilotons of ethylene oxide are produced per cubic meter of catalyst, the catalyst being in the form of particulate solids, the catalyst being in a reaction zone in each process microchannel; and maintaining an average temperature in the reaction zones below about 220° C.;

wherein the microchannel reactor further comprises a plurality of heat exchange channels, the heat exchange channels exchanging heat with the process microchannels.

66. A process, comprising reacting ethylene and oxygen or a source of oxygen in the presence of an olefin epoxidation catalyst in a plurality of process microchannels in a microchannel reactor during a production run to form a product comprising ethylene oxide at a rate of at least about 350 $Kg/m^3_{cat}/hr$, the selectivity to ethylene oxide being at least about 84%, the production run continuing until at least about 2 kilotons of ethylene oxide are produced per cubic meter of catalyst, the catalyst being in the form of particulate solids, the catalyst being in a reaction zone in each process microchannel; and maintaining an average temperature in the reaction zones below about 220° C.;

wherein the microchannel reactor further comprises a plurality of heat exchange channels, the heat exchange channels exchanging heat with the process microchannels.

67. A process, comprising reacting ethylene and oxygen or a source of oxygen in the presence of an olefin epoxidation catalyst in a plurality of process microchannels in a microchannel reactor during a production run to form a product comprising ethylene oxide at a rate of at least about 250 $Kg/m^3_{cat}/hr$, the selectivity to ethylene oxide being at least about 84%, the production run continuing until at least about 2 kilotons of ethylene oxide are produced per cubic meter of catalyst, the catalyst being in the form of particulate solids, the catalyst being in a reaction zone in each process microchannel; and maintaining an average temperature in the reaction zones above about 265° C.;

wherein the microchannel reactor further comprises a plurality of heat exchange channels, the heat exchange channels exchanging heat with the process microchannels.

68. A process, comprising reacting ethylene and oxygen or a source of oxygen in the presence of an olefin epoxidation catalyst in a plurality of process microchannels in a microchannel reactor during a production run to form a product comprising ethylene oxide at a rate of at least about 350 $Kg/m^3_{cat}/hr$, the selectivity to ethylene oxide being at least about 80%, the production run continuing until at least about 2 kilotons of ethylene oxide are produced per cubic meter of catalyst, the catalyst being in the form of particulate solids, the catalyst being in a reaction zone in each process microchannel; and maintaining an average temperature in the reaction zones above about 265° C.;

wherein the microchannel reactor further comprises a plurality of heat exchange channels, the heat exchange channels exchanging heat with the process microchannels.

69. A process, comprising reacting ethylene and oxygen or a source of oxygen in the presence of an olefin epoxidation catalyst in a plurality of process microchannels in a microchannel reactor during a production run to form a product comprising ethylene oxide at a rate of at least about 350 $Kg/m^3_{cat}/hr$, the production run continuing until at least about 2 kilotons of ethylene oxide are produced per cubic meter of catalyst, the catalyst being in the form of particulate solids, the selectivity to ethylene oxide being at least about 84%, the catalyst being in a reaction zone in each process microchannel; and maintaining an average temperature in the reaction zones above about 265° C.;

wherein the microchannel reactor further comprises a plurality of heat exchange channels, the heat exchange channels exchanging heat with the process microchannels.

70. The process of claim 1 wherein a bed of inert particulates is positioned in the process microchannel upstream and/or downstream of the catalyst.

\* \* \* \* \*